US008754270B2

(12) United States Patent
Weiner et al.

(10) Patent No.: US 8,754,270 B2
(45) Date of Patent: Jun. 17, 2014

(54) PROCESS FOR VAPOR PHASE HYDROGENATION

(71) Applicant: Celanese International Corporation, Irving, TX (US)

(72) Inventors: Heiko Weiner, Pasadena, TX (US); Radmila Wollrab, Pasadena, TX (US); Victor J. Johnston, Houston, TX (US); John L. Potts, Angleton, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/644,691

(22) Filed: Oct. 4, 2012

(65) Prior Publication Data

US 2013/0072728 A1    Mar. 21, 2013

Related U.S. Application Data

(63) Continuation of application No. 12/588,727, filed on Oct. 26, 2009, now Pat. No. 8,309,772, which is a continuation-in-part of application No. 12/221,141, filed on Jul. 31, 2008, now Pat. No. 7,863,489.

(51) Int. Cl.
*C07C 29/149* (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| | | | |
|---|---|---|---|
| 2,021,698 A | 11/1935 | Perkins | |
| 2,105,540 A | 1/1938 | Lazier | |
| 2,607,807 A | 8/1952 | Ford | |
| 2,744,939 A | 5/1956 | Kennel | |
| 2,882,244 A | 4/1959 | Milton | |
| 3,130,007 A | 4/1964 | Breck | |
| 3,478,112 A | 11/1969 | Karl et al. | |
| 3,702,886 A | 11/1972 | Argauer et al. | |
| 3,729,429 A | 4/1973 | Robson | |
| 3,864,284 A | 2/1975 | Clippinger et al. | |
| 3,990,952 A | 11/1976 | Katzen et al. | |
| 4,065,512 A | 12/1977 | Cares | |
| 4,228,307 A | 10/1980 | Zimmerschied | |
| 4,270,015 A | 5/1981 | Knifton | |
| 4,275,228 A | 6/1981 | Gruffaz et al. | |
| 4,317,918 A | 3/1982 | Takano et al. | |
| 4,328,373 A | 5/1982 | Strojny | |
| 4,337,351 A | 6/1982 | Larkins, Jr. | |
| 4,374,265 A | 2/1983 | Larkins | |
| 4,395,576 A | 7/1983 | Kwantes et al. | |
| 4,398,039 A | 8/1983 | Pesa et al. | |
| 4,399,305 A | 8/1983 | Schreck | |
| 4,421,939 A | 12/1983 | Kiff et al. | |
| 4,443,639 A | 4/1984 | Pesa et al. | |
| 4,465,854 A | 8/1984 | Pond et al. | |
| 4,471,136 A | 9/1984 | Larkins et al. | |
| 4,480,115 A | 10/1984 | McGinnis | |
| 4,517,391 A | 5/1985 | Schuster et al. | |
| 4,521,630 A | 6/1985 | Wattimena et al. | |
| 4,550,185 A | 10/1985 | Mabry et al. | |
| 4,581,473 A | 4/1986 | Polichnowski et al. | |
| 4,613,700 A | 9/1986 | Maki et al. | |
| 4,620,050 A | 10/1986 | Cognion et al. | |
| 4,678,543 A | 7/1987 | Houben et al. | |
| 4,692,218 A | 9/1987 | Houben et al. | |
| 4,696,596 A | 9/1987 | Russell et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,843,170 A | 6/1989 | Isshiki et al. | |
| 4,886,905 A | 12/1989 | Larkins et al. | |
| 4,978,778 A | 12/1990 | Isshiki et al. | |
| 4,985,572 A | 1/1991 | Kitson et al. | |
| 4,990,655 A | 2/1991 | Kitson et al. | |
| 5,008,235 A | 4/1991 | Wegman et al. | |
| 5,061,671 A | 10/1991 | Kitson et al. | |
| 5,124,004 A | 6/1992 | Grethlein et al. | |
| 5,137,861 A | 8/1992 | Shih et al. | |
| 5,149,680 A | 9/1992 | Kitson et al. | |
| 5,155,084 A | 10/1992 | Horn et al. | |
| 5,185,308 A | 2/1993 | Bartley et al. | |
| 5,241,106 A | 8/1993 | Inoue et al. | |
| 5,243,095 A | 9/1993 | Roberts et al. | |
| 5,306,845 A | 4/1994 | Yokohama et al. | |
| 5,350,504 A | 9/1994 | Dessau | |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

T. Yokoyama, et al., "Carboxylic Acids and Derivatives", Fine Chemicals through Heterogenous Catalysis, pp. 370-379, 1981.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

(Continued)

*Primary Examiner* — Elvis O Price

(57) ABSTRACT

A process for selective formation of ethanol from acetic acid includes contacting a feed stream containing acetic acid and hydrogen at an elevated temperature with catalyst comprising platinum and tin on a high surface area silica promoted with calcium metasilicate. Selectivities to ethanol of over 85% are achieved at 280° C. with catalyst life in the hundreds of hours.

6 Claims, 7 Drawing Sheets

(56) References Cited

U.S. PATENT DOCUMENTS

| | | |
|---|---|---|
| 5,426,246 A | 6/1995 | Nagahara et al. |
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Weiguny et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 6,008,384 A | 12/1999 | Bockrath et al. |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,232,352 B1 | 5/2001 | Vidalin et al. |
| 6,232,504 B1 | 5/2001 | Barteau et al. |
| 6,294,703 B1 | 9/2001 | Hara et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,863,489 B2 | 1/2011 | Johnston et al. |
| 7,884,253 B2 | 2/2011 | Stites et al. |
| 7,994,368 B2 | 8/2011 | Johnston et al. |
| 8,071,821 B2 | 12/2011 | Johnston et al. |
| 8,309,772 B2 | 11/2012 | Weiner et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2006/0019360 A1 | 1/2006 | Verser et al. |
| 2006/0102520 A1 | 5/2006 | Lapinski et al. |
| 2006/0106246 A1 | 5/2006 | Warner et al. |
| 2006/0127999 A1 | 6/2006 | Verser et al. |
| 2007/0270511 A1 | 11/2007 | Melnichuk et al. |
| 2008/0207953 A1 | 8/2008 | Houssin et al. |
| 2008/0319236 A1 | 12/2008 | McNeff et al. |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0883171 | 4/2009 | Frye, Jr. et al. |
| 2009/0166172 A1 | 7/2009 | Casey et al. |
| 2009/0221725 A1 | 9/2009 | Chornet et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0029996 A1 | 2/2010 | Danjo et al. |
| 2010/0113843 A1 | 5/2010 | Lee et al. |
| 2010/0121114 A1 | 5/2010 | Johnston et al. |
| 2010/0168493 A1 | 7/2010 | Le Peltier et al. |
| 2010/0196789 A1 | 8/2010 | Fisher et al. |
| 2010/0249479 A1 | 9/2010 | Berg-Slot et al. |
| 2011/0065572 A1 | 3/2011 | Olken et al. |
| 2011/0282109 A1 | 11/2011 | Johnston et al. |
| 2012/0253085 A1 | 10/2012 | Johnston et al. |

FOREIGN PATENT DOCUMENTS

| | | |
|---|---|---|
| CN | 102229520 | 11/2011 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 0407038 | 1/1991 |
| EP | 0990638 | 4/2000 |
| EP | 1262234 | 12/2002 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 83/03409 | 10/1983 |
| WO | WO 2003/040037 | 5/2003 |
| WO | WO 2005/102513 | 11/2005 |
| WO | WO 2009/009322 | 1/2009 |
| WO | WO 2009/009323 | 1/2009 |
| WO | WO 2009/063176 | 5/2009 |
| WO | WO 2009/086839 | 7/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/055285 | 5/2010 |

OTHER PUBLICATIONS

Santori et al.(2000). Hydrogenation of carbonylic compounds on Pt/SiO2 catalysts modified with SnBu4, Studies in Surface Science and Catalysis, 130, 2063-2068.

Rodrigues and Bueno, "Co/SiO2 catalysts for selective hydrogenation of crotonaldehyde: III. Promoting effect of zinc," Applied Catalysis A: General (2004), 257, p. 210-211.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., The formation of ketones and aldehydes from carboxylic acids, structure-activity relationship for two competitive reactions, Journal of Molecular Catalysis A: Chemical 103 Jun. 14, 1995, 175-180.

(56) References Cited

OTHER PUBLICATIONS

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Nitta, et al. "Selective hydrogenation of $\alpha\beta$-unsaturated aldehydes on cobalt—silica catalysts obtained from cobalt chrysotile," Applied Catal. (1989), 56, p. 9-22.

Nefedov and I V Mishin B K, "Synthesis of diethyl ether in presence of zeolite catalysts", Russian Chem. Bull., Springer Anew York LLC, v. 28, Jan. 1, 1979, pp. 183-186.

Liberkova, and Tourounde, "Performance of Pt/SnO2 catalyst in the gas phase hydrogenation of crotonaldehyde," J. Mol. Catal. A: Chemical (2002), 180, p. 221-230.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.

Consonni, et al. "High Performances of Pt/ZnO Catalysts in Selective Hydrogenation of Crotonaldehyde," J. Catal. (1999), 188, p. 165-175.

Ammari, et al. "An emergent catalytic material: Pt/ZnO catalyst for selective hydrogenation of crotonaldehyde," J. Catal. (2004), 221, p. 32-42.

Ammari, et al. "Selective hydrogenation of crotonaldehyde on Pt/ZnCl2/SiO2 catalysts," J. Catal. (2005), 235, p. 1-9.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Brunauer Emmett and Teller, J. Am. Chem. Soc. 60, 309 (1938).

International Search Report and Written Opinion for PCT/US2009/004197 mailed Mar. 24, 2010.

International Search Report and Written Opinion for PCT/US2009/004195 mailed Mar. 26, 2010.

International Search Report and Written Opinion mailed on May 22, 2012 in corresponding International Application No. PCT/US2012/031207.

Minglin Xiang et al., "XPS study of potassium-promoted molybdenum carbides for mixed alcohols synthesis via CO hydrogenation", Journal of Natural Gas Chemistry, vol. 19, 2010, pp. 151-155.

Jingfa D. et al., "Acidic properties of ZSM-5 zeolite and conversion of ethanol to diethyl ether" Applied Catalysis, Amsterdam, NL. vol. 41, Jan. 1, 1988. pp. 13-22, XP 009144884.

International Search Report and Written Opinion mailed on Feb. 28, 2011 in corresponding International Application No. PCT/US2010/054132.

International Written Opinion mailed on Nov. 29, 2011 in corresponding International Application No. PCT/US2010/054132.

International Preliminary Report on Patentability mailed Feb. 1, 2012 in corresponding International Application No. PCT/US2010/054132.

International Search Report and Written Opinion for PCT/US2010/054134 mailed Feb. 28, 2011.

International Search Report and Written Opinion for PCT/US2010/022950 mailed Sep. 7, 2011.

Invitation to Pay Fees and Partial International Search Report for PCT/US2010/022950 mailed Jun. 15, 2010.

International Search Report and Written Opinion for PCT/US2010/022947 mailed Jun. 7, 2010.

International Search Report and Written Opinion for PCT/US2010/022949 mailed Jun. 7, 2010.

International Search Report and Written Opinion for PCT/US2010/022953 mailed Jun. 7, 2010.

Office Action for U.S. Appl. No. 12/699,024 dated Nov. 29, 2012.

Office Action for U.S. Appl. No. 12/698,947 dated Dec. 12, 2012.

Office Action for U.S. Appl. No. 12/698,968 dated Dec. 18, 2012.

PROCESS FOR VAPOR PHASE HYDROGENATION

CROSS REFERENCE TO RELATED APPLICATION

This application is a continuation of Ser. No. 12/588,727, filed Oct. 26, 2009, which is a continuation in part of Ser. No. 12/221,141; filed Jul. 31, 2008, entitled "Direct and Selective Reduction of Ethanol from Acetic Acid Utilizing a Platinum/Tin Catalyst", now U.S. Pat. No. 7,863,489, the priority of which is hereby claimed and the disclosure of which is herein incorporated by reference.

FIELD OF THE INVENTION

The present invention relates generally to a tunable catalyst for the hydrogenation of carboxylic acids, particularly acetic acid and a flexible process of acetic acid dehydrogenation in which the proportion of ethanol relative to ethyl acetate and acetaldehyde may be varied with each catalyst change out to adapt to changing commercial conditions. More specifically, the present invention relates to a catalyst for gas phase hydrogenation of carboxylic acids, particularly acetic acid to produce a variety of products including the corresponding alcohols, esters and aldehydes, especially ethanol. The catalysts exhibit excellent activity and selectivity over the range of products.

BACKGROUND

There is a long felt need for an economically viable process to convert acetic acid to ethanol which may be used in its own right or subsequently converted to ethylene which is an important commodity feedstock as it can be converted to vinyl acetate and/or ethyl acetate or any of a wide variety of other chemical products. For example, ethylene can also be converted to numerous polymer and monomer products. Fluctuating natural gas and crude oil prices contribute to fluctuations in the cost of conventionally produced, petroleum or natural gas-sourced ethylene, making the need for alternative sources of ethylene all the greater when oil prices rise.

Catalytic processes for reduction of alkanoic acids and other carbonyl group containing compounds have been widely studied and a variety of combinations of catalysts, supports and operating conditions have been mentioned in the literature. Reduction of various carboxylic acids over metal oxides is reviewed by T. Yokoyama et al. in "Fine chemicals through heterogeneous catalysis. Carboxylic acids and derivatives." Chapter 8.3.1, summarizes some of the developmental efforts for hydrogenation catalysts for various carboxylic acids. (Yokoyama, T.; Setoyama, T. "Carboxylic acids and derivatives." in: "Fine chemicals through heterogeneous catalysis." 2001, 370-379.)

A series of studies by M. A. Vannice et al. concern conversion of acetic acid over a variety of heterogeneous catalysts (Rachmady W.; Vannice, M. A.; J. Catal. 2002, 207, 317-330.)

Vapor-phase reduction of acetic acid by $H_2$ over both supported and unsupported iron was reported in separate study. (Rachmady, W.; Vannice, M. A. J. Catal. 2002, 208, 158-169.)

Further information on catalyst surface species and organic intermediates is set forth in Rachmady, W.; Vannice, M. A., J. Catal. 2002, 208, 170-179.

Vapor-phase acetic acid hydrogenation was studied further over a family of supported Pt-Fe catalysts in Rachmady, W.; Vannice, M. A. J. Catal. 2002, 209, 87-98 and Rachmady, W.; Vannice, M. A. J. Catal. 2000, 192, 322-334.

Various related publications concerning the selective hydrogenation of unsaturated aldehydes may be found in (Djerboua, F.; Benachour, D.; Touroude, R. Applied Catalysis A: General 2005, 282, 123-133.; Liberkova, K.; Tourounde, R. J. Mol. Catal. 2002, 180, 221-230.; Rodrigues, E. L.; Bueno, J. M. C. Applied Catalysis A: General 2004, 257, 210-211.; Ammari, F.; Lamotte, J.; Touroude, R. J. Catal. 2004, 221, 32-42; Ammari, F.; Milone, C.; Touroude, R. J. Catal. 2005, 235, 1-9.; Consonni, M.; Jokic, D.; Murzin, D. Y.; Touroude, R. J. Catal. 1999, 188, 165-175.; Nitta, Y.; Ueno, K.; Imanaka, T.; Applied Catal. 1989, 56, 9-22.)

Studies reporting activity and selectivity over cobalt, platinum and tin—containing catalysts in the selective hydrogenation of crotonaldehyde to the unsaturated alcohol are found in R. Touroude et al. (Djerboua, F.; Benachour, D.; Touroude, R. Applied Catalysis A: General 2005, 282, 123-133 as well as Liberkova, K.; Tourounde, R.; J. Mol. Catal. 2002, 180, 221-230) as well as K. Lazar et al. (Lazar, K.; Rhodes, W. D.; Borbath, I.; Hegedues, M.; Margitfalvi, 1. L. Hyperfine Interactions 2002, 1391140, 87-96.)

M. Santiago et al. (Santiago, M. A. N.; Sanchez-Castillo, M. A.; Cortright, R. D.; Dumesic, 1. A. J. Catal. 2000, 193, 16-28.) idiscuss microcalorimetric, infrared spectroscopic, and reaction kinetics measurements combined with quantum-chemical calculations.

Catalytic activity in for the acetic acid hydrogenation has also been reported for heterogeneous systems with Rhenium and Ruthenium. (Ryashentseva, M. A.; Minachev, K. M.; Buiychev, B. M.; Ishchenko, V. M. Bull. Acad Sci. USSR 1988, 2436-2439).

U.S. Pat. No. 5,149,680 to Kitson et al. describes a process for the catalytic hydrogenation of carboxylic acids and their anhydrides to alcohols and/or esters utilizing platinum group metal alloy catalysts. U.S. Pat. No. 4,777,303 to Kitson et al. describes a process for the productions of alcohols by the hydrogenation of carboxylic acids. U.S. Pat. No. 4,804,791 to Kitson et al. describes another process for the production of alcohols by the hydrogenation of carboxylic acids. See also U.S. Pat. Nos. 5,061,671; 4,990,655; 4,985,572; and 4,826,795.):

Malinowski et al. (Bull. Soc. Chim. Belg. (1985), 94(2), 93-5,) discuss reaction catalysis of acetic acid on low-valent titanium heterogenized on support materials such as silica ($SiO_2$) or titania ($TiO_2$).

Bimetallic ruthenium-tin/silica catalysts have been prepared by reaction of tetrabutyl tin with ruthenium dioxide supported on silica. (Loessard et al., Studies in Surface Science and Catalysis (1989), Volume Date 1988, 48 (Struct. React. Surf.), 591-600.)

The catalytic reduction of acetic acid has also been studied in, for instance, Hindermann et al., (Hindermann et al., J. Chem. Res., Synopses (1980), (11), 373), dsiclosing catalytic reduction of acetic acid on iron and on alkali-promoted iron.

Existing processes suffer from a variety of issues impeding commercial viability including: (i) catalysts without requisite selectivity to ethanol; (ii) catalysts which are possibly prohibitively expensive and/or nonselective for the formation of ethanol and produces undesirable by-products; (iii) operating temperatures and pressures which are excessive; and/or (iv) insufficient catalyst life.

SUMMARY OF THE INVENTION

We have found that when reducing acetic acid over a platinum tin catalyst dispersed on a modified stabilized silicaceous support including an effective amount of a support modifier selected from the group consisting of: (i) alkaline earth oxides, (ii) alkali metal oxides, (iii) alkaline earth metasilicates, (iv) alkali metal metasilicates, (v) zinc oxide, (vi) zinc metasilicate and (vii) precursors for any of (i)-(vi), and mixtures of any of (i)-(vii) by passing a gaseous stream comprising hydrogen and acetic acid in the vapor phase in a mole ratio of hydrogen to acetic acid of at least about 4:1 at a temperature of between about 125° C. and 350° C., more preferably between about 225 and 300° C., still more preferably between about 250° C. and 300° C. over that catalyst, we can obtain high selectivity in conversion to ethanol when the amounts and oxidation states of the platinum and tin, as well as the ratio of platinum to tin and the modified stabilized silicaceous support are controlled as described herein. In one aspect of the invention, we counteract the effect of Bronsted acid sites present on the surface of the silicaceous support with a support modifier selected as described above. In another aspect, the above described support modifiers are effective to prevent excessive loss of activity and selectivity by the catalyst over periods of up to 168, 336 or even 500 hours at 275° C. in the presence of flowing acetic acid vapor. In another aspect of the invention, the support modifier is effective to suppress production of ethyl acetate resulting in high selectivity to ethanol production when desired accompanied by low selectivity toward conversion of acetic acid to highly undesirable by-products such as alkanes. Preferably, the support modifier is chosen from the group consisting of oxides and metasilicates of sodium, potassium, magnesium, calcium, and zinc as well as precursors therefor and mixtures of any of the foregoing. The most preferred support modifier is calcium metasilicate.

We have found that when reducing acetic acid over a platinum tin catalyst dispersed on an essentially basic calcium metasilicate/silica support by passing a gaseous stream comprising hydrogen and acetic acid in the vapor phase in a mole ratio of hydrogen to acetic acid of at least about 4:1 at a temperature of between about 125° C. and 350° C., more preferably between about 225 and 300° C., still more preferably between about 250° C. and 300° C. over that catalyst, we can obtain high selectivity in conversion to ethanol when the amounts and oxidation states of the platinum and tin, as well as the ratio of platinum to tin and the acidity of the calcium metasilicate/silica support are controlled as described herein. In particular, using preferred catalysts and processes of the present invention at least 80% of the acetic acid converted is converted to ethanol and less than 4% of the acetic acid is converted to compounds other than compounds chosen from the group consisting of ethanol, acetaldehyde, ethyl acetate, ethylene and mixtures thereof. In preferred processes, platinum is present in an amount of 0.5% to 5% of the weight of the catalyst; while tin is present in an amount of from at least 0.5 up to 10% by weight of the catalyst; preferably, the surface area of the support is at least about 100 m$^2$/g, more preferably about 150 m$^2$/g, still more preferably at least about 200 m$^2$/g, most preferably at least about 250 m$^2$/g; the mole ratio of tin to platinum group metal is preferably from about 1:2 to about 2:1, more preferably from about 2:3 to about 3:2; still more preferably from about 5:4 to about 4:5; most preferably from about 9:10 to 10:9. In many cases the support comprises calcium silicate in an amount effective to balance Bronsted acid sites resulting from residual alumina in the silica; typically from about 1% up to about 10% by weight of calcium silicate is sufficient to ensure that the support is essentially neutral or basic in character. In one particularly preferred embodiment, platinum is present in the hydrogenation catalyst in an amount of at least about 0.75%, more preferably 1% by weight; the mole ratio of tin to platinum is from about 5:4 to about 4:5; and the support comprises from at least about 2.5% to about 10% by weight of calcium silicate.

One aspect of many embodiments of the present invention is that space velocities of over about 1000 hr$^{-1}$, 2500 hr$^{-1}$ and even over 5000 hr$^{-1}$ can be used while at least 90% of the acetic acid converted is converted to ethanol and less than 2% of the acetic acid is converted to compounds other than compounds chosen from the group consisting of ethanol, acetaldehyde, ethyl acetate, and ethylene and mixtures thereof. In many embodiments of the present invention, formation of alkanes is low, usually under 2%, often under 1%, and in many cases under 0.5% of the acetic acid passed over the catalyst is converted to alkanes having little value other than as fuel or synthesis gas.

In another aspect of this invention, alkanoic acids are hydrogenated by passing a gaseous stream comprising hydrogen and the alkanoic acid in the vapor phase in a mole ratio of hydrogen to alkanoic acid of at least about 2:1 at a temperature of between about 125° C. and 350° C. over a hydrogenation catalyst comprising: a platinum group metal chosen from the group consisting of platinum, palladium and mixtures thereof on a silicaceous support chosen from the group consisting of silica, calcium metasilicate and calcium metasilicate promoted silica; and a promoter chosen the group consisting of tin, rhenium and mixtures thereof, the silicaceous support being optionally promoted with a promoter chosen from the group consisting of: a promoter chosen from the group consisting of alkali metals; alkaline earth elements and zinc in an amount of 1 to 5% by weight of the catalyst; a redox promoter chosen from the group consisting of: $WO_3$; $MoO_3$; $Fe_2O_3$ and $Cr_2O_3$ in an amount of 1 to 50% by weight of the catalyst; and an acidic modifier chosen from the group consisting of $TiO_2$; $ZrO_2$; $Nb_2O_5$; $Ta_2O_5$; and $Al_2O_3$ in an amount of 1 to 50% by weight of the catalyst wherein the acidity of the support is controlled such that less than 4, preferably less than 2 and most preferably less than about 1% of the alkanoic acid is converted to an alkane. In many cases, at least one of platinum and palladium is present in an amount of 0.25% to 5% of the weight of the catalyst; the combined amount of platinum and palladium present is at least 0.5% by weight of catalyst; and the combined amount of rhenium and tin present is at least 0.5 to 10% by weight. As with the catalysts comprising platinum and tin on a basic silica support, in this process, the amounts and oxidation states of the platinum group metals, the rhenium and tin promoters, as well as the mole ratio of platinum group metal to combined moles of rhenium and tin present; and the acidity of the silicaceous support are controlled such that at least 80% of the acetic acid converted is converted to a compound chosen from the group consisting of an alkanol and alkyl acetate while less than 4% of the alkanoic acid is converted to compounds other than compounds chosen from the group consisting of the corresponding alkanols, alkyl acetates and mixtures thereof. Preferably, at least one of platinum and palladium is present in an amount of 0.5% to 5% of the weight of the catalyst; the combined amount of platinum and palladium present is at least 0.75% to 5% of the weight of the catalyst. Preferably, the alkanoic acid is acetic acid and the combined amount of tin and rhenium present is at least 1.0% by weight of catalyst while the amounts and oxidation states of the platinum group metals, the rhenium and tin promoters, as well as the ratio of platinum group metal to rhenium and tin promoters; and acidity of the silicaceous support are controlled such that at least 80% of the acetic acid converted is converted to ethanol or ethyl acetate and less than 4% of the acetic acid is converted to compounds other than compounds chosen from the group consisting of ethanol, acetaldehyde, ethyl acetate, ethylene and mixtures thereof. Preferably, the combined weight of rhenium and tin present is from about 1 to 10% by weight of the catalyst while the mole ratio of platinum group metal to moles of rhenium and tin combined is from about 1:2 to about 2:1.

In another aspect, this invention relates to a process for hydrogenation of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of metallic components dispersed on an oxidic support, said hydrogenation catalyst having the composition:

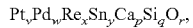
$Pt_vPd_wRe_xSn_yCa_pSi_qO_r,$ wherein the ratio of v:y is between 3:2 and 2:3; and/or the ratio of w:x is between 1:3 and 1:5, p and q are selected such that p:q is from 1:20 to 1:200 with r being selected to satisfy valence requirements and v and w being selected such that $$0.005 \leq \frac{(3.25v + 1.75w)}{q} \leq 0.05.$$

In this aspect, the process conditions and values of v, w, x, y, p, q, and r are preferably chosen such that at least 90% of the acetic acid converted is converted to a compound chosen from the group consisting of ethanol and ethyl acetate while less than 4% of the acetic acid is converted to alkanes. In many embodiments of the present invention, p is selected, in view of any minor impurities present, to ensure that the surface of the support is essentially free of active Bronsted acid sites.

Still another aspect of this invention relates to a process for production of ethanol by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of metallic components dispersed on an oxidic support, said hydrogenation catalyst having the composition:

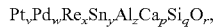
$Pt_vPd_wRe_xSn_yAl_zCa_pSi_qO_r,$ wherein v and y are between 3:2 and 2:3; w and x are between 1:3 and 1:5, wherein p and z and the relative locations of aluminum and calcium atoms present are controlled such that Bronsted acid sites present upon the surface thereof are balanced by calcium silicate; p and q are selected such that p:q is from 1:20 to 1:200 with r being selected to satisfy valence requirements and v and w are selected such that $$0.005 \leq \frac{(3.25v + 1.75w)}{q} \leq 0.05.$$

Preferably, in this aspect, the hydrogenation catalyst has a surface area of at least about 100 m²/g and z and p≥z. In many embodiments of the present invention, p is selected, in view of any minor impurities present, to also ensure that the surface of the support is essentially free of active Bronsted acid sites which seem to facilitate conversion of ethanol into ethyl acetate.

Another aspect of this invention relates to a process for production of ethanol and ethyl acetate by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst comprising: a platinum group metal chosen from the group consisting of platinum, and mixtures of platinum and palladium on a silicaceous support chosen from the group consisting of silica, and silica promoted with up to about 7.5 calcium metasilicate, the amount of platinum group metal present being at least about 2.0%, the amount of platinum present being at least about 1.5%; and a metallic promoter chosen from the group consisting from the group consisting of rhenium and tin an amount of between about 1% and 2% by weight of the catalyst, the mole ratio of platinum to metallic promoter being between about 3:1 and 1:2; the silicaceous support being optionally promoted with a second promoter chosen from the group consisting of: a donor promoter chosen from the group consisting of alkali metals; alkaline earth elements and zinc in an amount of 1 to 5% by weight of the catalyst; a redox promoter chosen from the group consisting of: $WO_3$; $MoO_3$; $Fe_2O_3$ and $Cr_2O_3$ in an amount of 1 to 50% by weight of the catalyst; an acidic modifier chosen from the group consisting of $TiO_2$; $ZrO_2$; $Nb_2O_5$; $Ta_2O_5$; and $Al_2O_3$ in an amount of 1 to 50% by weight of the catalyst; and combinations thereof.

In preferred aspects of this invention, the mole ratio of metallic promoter to platinum group metal is from about 2:3 to about 3:2, more preferably about 5:4 to about 4:5 and most preferably from about 9:10 to about 10:9 while the surface area of the silicaceous support is at least about 200 m²/g and the amount of sodium silicate is sufficient to render the surface of the support essentially basic. In some cases, the use of calcium silicate can be controlled such that the mole number of Bronsted Acid sites present on the surface thereof is no more than the mole number of Bronsted Acid sites present on the surface of Saint-Gobain N or Pro SS61138 silica: in other cases, the silica used may be a high purity pyrogenic silica having a low content of alumina or other impurities. In many cases, such silicas will comprise over 99% silica, more preferably over 99.5% silica, most preferably over 99.7% silica. In many embodiments of the present invention, either by control of the purity of the silica or by balancing Bronsted acid sites present on the surface of the support with calcium silicate or one of the other suitable stabilizer modifiers discussed herein, the available mole number of Bronsted Acid sites present on the surface thereof is no more than the mole number of Bronsted Acid sites present on the surface of Saint-Gobain N or Pro SS61138 silica, preferably less than half, more preferably less than 25% and still more preferably less than 10% of the mole number of Bronsted Acid sites present on the surface of Saint-Gobain N or Pro SS61138 silica. The number of acid sites present on the surface of the support may be determined using pyridine titration following procedures described in:

(1) F. Delannay, Ed., "Characterization of Heterogeneous Catalysts"; Chapter III: Measurement of Acidity of Surfaces, p. 370-404; Marcel Dekker, Inc., N.Y. 1984.
(2) C. R. Brundle, C. A. Evans, Jr., S. Wilson, L. E. Fitzpatrick, Eds., "Encyclopedia of Materials Characterization"; Chapter 12.4: Physical and Chemical Adsorption Measurements of Solid Surface Areas, p. 736-744; Butterworth-Heinemann, Mass. 1992.
(3) G. A. Olah, G. K. Sura Prakask, Eds, "Superacids"; John Wiley & Sons, N.Y. 1985.

Throughout this specification and claims, unless the context indicates otherwise, when measuring the acidity of a surface or the number of acid sites thereupon, the technique described in F. Delannay, Ed., "Characterization of Heterogeneous Catalysts"; Chapter III: Measurement of Acidity of Surfaces, p. 370-404; Marcel Dekker, Inc., N.Y. 1984 should be used.

In the more preferred case, the surface area of the silicaceous support is at least about 250 m$^2$/g and the mole number of available Bronsted Acid sites present on the surface thereof is no more than one half the mole number of Bronsted Acid sites present on the surface of Saint-Gobain N or Pro HSA SS61138 silica and the hydrogenation will be conducted at a temperature of between about 250° C. and 300° C.

As will be appreciated by one of skill in the art reviewing the discussion herein, catalyst supports other than silicaceous supports described above may be used in some embodiments provided that the components are selected such that the catalyst system is suitably active, selective and robust under the process conditions employed. Suitable supports may include stable metal oxide-based supports or ceramic-based supports as well as molecular sieves, including zeolites. So also, in some embodiments, carbon supports may be used as described in the aforementioned U.S. Pat. No. 5,149,680 to Kitson et al. at Col. 2, line 64-col 4, line 22, the disclosure of which is incorporated herein by reference.

In cases where mixtures of ethanol and ethyl acetate are to be produced simultaneously, in many embodiments of the present invention, the hydrogenation catalyst may comprise: palladium on a silicaceous support chosen from the group consisting of silica, and silica promoted with up to about 7.5 calcium metasilicate, the amount of palladium present being at least about 1.5%; while the metallic promoter is rhenium in an amount of between about 1% and 10% by weight of the catalyst, the mole ratio of rhenium to palladium being between about 4:1 and 1:4, preferably 2:1 and 1:3.

In cases where it is desired to produce primarily ethanol, the catalyst, in many embodiments of the present invention, may consist essentially of platinum on a silicaceous support consisting essentially of silica promoted with from about 3 up to about 7.5% calcium silicate, the amount of platinum present being at least about 1.0%, and a tin promoter in an amount of between about 1% and 5% by weight of the catalyst, the mole ratio of platinum to tin in many embodiments of the present invention being between about 9:10 and 10:9. In some cases, minor amounts of another platinum group metal may be included, most often palladium in the catalytic metal of the formulation. In many embodiments of the present invention, the amount of platinum group metal present is at least about 2.0%, the amount of platinum present being at least about 1.5%, preferably between 2.5 and 3.5 weight percent platinum and the tin promoter is present in an amount of between about 2% and 5% by weight of the catalyst, while the process is conducted at a temperature of between about 250° C. and 300° C. at a GHSV of at least about 1000 hr$^{-1}$ at a pressure of at least 2 atm. The ratio of tin to platinum is preferably between 2:3 and 3:2, more preferably between 4:5 and 5:4 and most preferably between 9:10 and 10:9. In yet other embodiments in which it is desired to produce primarily ethanol, the catalyst may comprise platinum on a silicaceous support consisting essentially of silica promoted with from about 3 up to about 7.5% calcium silicate, the amount of platinum present being at least about 1.0%, and a tin promoter in an amount of between about 1% and 5% by weight of the catalyst, the mole ratio of platinum to tin in many embodiments of the present invention being between about 9:10 and 10:9.

Another aspect of the invention relates to a particulate catalyst for hydrogenation of alkanoic acids to the corresponding alkanol, comprising: a platinum group metal chosen from the group consisting of platinum, palladium and mixtures thereof on a silicaceous support chosen from the group consisting of silica, and silica promoted with from about 3.0 up to about 7.5 calcium metasilicate, the surface area of the silicaceous support being at least about 150 m$^2$/g; and a tin promoter in an amount of between about 1% and 3% by weight of the catalyst, the mole ratio of platinum to tin being between about 4:3 and 3:4; the composition and structure of the silicaceous support being chosen such that the surface thereof is essentially basic.

Another aspect of this invention relates to a particulate hydrogenation catalyst consisting essentially of: a silicaceous support having dispersed thereupon a platinum group metal chosen the group consisting of platinum, palladium, and mixtures thereof with a promoter chosen from the group consisting of tin, cobalt and rhenium, the silicaceous support having a surface area of at least about 175 m$^2$/g and being chosen from the group consisting of silica, calcium metasilicate and calcium metasilicate promoted silica having calcium metasilicate being disposed on the surface thereof, the surface of the silicaceous support being essentially free of Bronsted acid sites due to alumina unbalanced by calcium. In those variants best suited for production of ethanol and ethyl acetate simultaneously, the total weight of platinum group metals present is between 0.5% and 2%, the amount of palladium present is at least 0.5%, the promoter is rhenium, the weight ratio of rhenium to palladium being between 10:1 and 2:1, and the amount of calcium meta-silicate is between 3 and 90%.

In those aspects best suited for production of ethanol at high selectivity, the total weight of platinum group metals present is between 0.5 and 2%, the amount of platinum present is at least 0.5%, the promoter is cobalt, the weight ratio of cobalt to platinum being between 20:1 and 3:1, and the amount of calcium silicate is between 3 and 90%, while for production of ethanol with a catalyst having extended life, the hydrogenation catalyst comprises between 2.5 and 3.5 weight percent platinum, between 3 weight % and 5 weight % tin dispersed on high surface area pyrogenically derived silica having a surface area of at least 200 m$^2$ per gram, said high surface area silica being promoted with an effective amount of calcium metasilicate to ensure that the surface thereof is essentially free of Bronsted acid sites unbalanced by calcium metasilicate, the molar ratio of platinum to tin being between 4:5 and 5:4.

In another catalyst of the present invention, the total weight of platinum group metal present is between 0.5 and 2%, the amount of palladium present is at least 0.5%, the promoter is cobalt, the weight ratio of cobalt to palladium being between 20:1 and 3:1, and the amount of calcium silicate is between 3 and 90%.

Still another catalyst of the present invention is a hydrogenation catalyst comprising: between 0.5 and 2.5 weight percent palladium, between 2 weight % and 7 weight % rhenium, the weight ratio of rhenium to palladium being at least 1.5:1.0, the rhenium and palladium being dispersed on a silicaceous support, said silicaceous support comprising at least 80% calcium metasilicate.

We have found that surprisingly high activity and life combined with excellent selectivity for hydrogenation of acetic acid to ethanol are obtained from catalysts chosen the group consisting of:
(i) catalysts combining a platinum group metal chosen the group consisting of platinum, palladium, and mixtures thereof with tin or rhenium on a silicaceous support chosen from the group consisting of silica, calcium metasilicate and calcium metasilicate promoted silica;

(ii) catalysts combining palladium and rhenium supported on a silicaceous support comprising chosen from the group consisting of silica, calcium metasilicate and calcium metasilicate promoted silica, the silicaceous support being optionally promoted with 1% to 5% of a promoter chosen group consisting of: alkali metals; alkaline earth elements and zinc, promoter being preferably added to the catalyst formulation in the form of the respective nitrates or acetates, of the these promoters, particularly preferred are potassium, cesium, calcium, magnesium and zinc;

(iii) platinum promoted with cobalt on a high surface area silicaceous support chosen from the group consisting of silica, calcium metasilicate and calcium metasilicate promoted silica; and (iv) palladium promoted with cobalt on a high surface area silicaceous support chosen from the group consisting of silica, calcium metasilicate and calcium metasilicate promoted silica.

Another aspect of the present invention concerns a process for hydrogenating alkanoic acids comprising passing a gaseous stream comprising hydrogen and an alkanoic acid in the vapor phase in a mole ratio of hydrogen to alkanoic acid of at least about 2:1 at a temperature of between about 125° C. and 350° C. over a hydrogenation catalyst comprising:

a. a platinum group metal chosen from the group consisting of platinum, palladium and mixtures thereof on a silicaceous support chosen from the group consisting of silica, calcium metasilicate and calcium metasilicate promoted silica; and b. a promoter chosen the group consisting of tin and rhenium, c. the silicaceous support being optionally promoted with a promoter chosen from the group consisting of:
   i. a promoter chosen from the group consisting of alkali metals; alkaline earth elements and zinc in an amount of 1 to 5% by weight of the catalyst;
   ii. a redox promoter chosen from the group consisting of: $WO_3$; $MoO_3$; $Fe_2O_3$ and $Cr_2O_3$ in an amount of 1 to 50% by weight of the catalyst; and
   iii. an acidic modifier chosen from the group consisting of $TiO_2$; $ZrO_2$; $Nb_2O_5$; $Ta_2O_5$; and $Al_2O_3$ in an amount of 1 to 50% by weight of the catalyst.

Preferably, the alkanoic acid is acetic acid, and platinum, if present, is present in an amount of 0.5% to 5% of the weight of the catalyst; palladium, if present, is present in an amount of 0.25% to 5% of the weight of the catalyst; the combined amount of platinum and palladium present is at least 0.5% by weight of catalyst; and tin is present in an amount of at least 0.5 to 5% with the ratio of platinum to tin being as previously described.

In another aspect of the invention, the surface area of the silicaceous support is at least about 150 $m^2/g$, more preferably at least about 200 $m^2/g'$ and most preferably at least about 250 $m^2/g$. In more preferred embodiments, the silicaceous support comprises up to about 7.5% calcium metasilicate. In other embodiments the silicaceous support comprises up to about 90% calcium metasilicate. In all embodiments, control of the acidity of the support can be quite beneficial, particularly when substantially pure ethanol is to be produced. In the case where silica alone is used as the support, it is quite beneficial to ensure that the amount of alumina, which is a common contaminant for silica, is low, preferably under 1%; more preferably under 0.5%; most preferably under 0.3% by weight. In this regard, so-called pyrogenic silica is greatly preferred as it commonly is available in purities exceeding 99.7%. In this application, when we mention high purity silica, we are referring to silica wherein acidic contaminants such as alumina are present at levels of less than 0.3% by weight. In the cases where calcium metasilicate promoted silica is used, it is not normally necessary to be quite as strict about the purity of the silica used as the support although alumina is undesirable and will not normally be added intentionally.

In more preferred embodiments of the present invention, platinum, if present, is present in an amount of 1% to 5% of the weight of the catalyst; palladium, if present, is present in an amount of 0.5% to 5% of the weight of the catalyst; and the combined amount of platinum and palladium present is at least 1% by weight of the catalyst.

In another preferred embodiment of the present invention where the support is essentially pure high surface area silica, preferably pyrogenically formed silica, tin is present in amount of 1% to 3% by weight of the catalyst and, more preferably, the mole ratio of tin to platinum group metal is from about 1:2 to about 2:1; still more preferably the mole ratio of tin to platinum is from about 2:3 to about 3:2; while most preferably the mole ratio of tin to platinum is from about 5:4 to about 4:5. In cases where the support also comprises a minor amount of $CaSiO_3$ or other stabilizer modifiers in the range of from about 2% to about 10%, larger amount of acidic impurities can be tolerated so long as they are counter-balanced by an appropriate amount of an essentially basic stabilizer modifier.

In another aspect of the present invention, the process is preferably carried out at a temperature of between about 225° C. and 300° C., more preferably between 250° C. and 300° C. wherein said hydrogenation catalyst comprises: a platinum group metal chosen from the group consisting of platinum, and mixtures of platinum and palladium on a silicaceous support chosen from the group consisting of silica, and silica promoted with up to about 7.5 calcium metasilicate, the amount of platinum group metal present being at least about 2.0%, the amount of platinum present being at least about 1.5%; and a tin promoter in an amount of between about 1% and 2% by weight of the catalyst, the mole ratio of platinum to tin being between about 3:1 and 1:2, the silicaceous support being optionally promoted with a promoter chosen from the group consisting of: a promoter chosen from the group consisting of alkali metals; alkaline earth elements and zinc in an amount of 1 to 5% by weight of the catalyst; a redox promoter chosen from the group consisting of: $WO_3$; $MoO_3$; $Fe_2O_3$ and $Cr_2O_3$ in an amount of 1 to 50% by weight of the catalyst; and an acidic modifier chosen from the group consisting of $TiO_2$; $ZrO_2$; $Nb_2O_5$; $Ta_2O_5$; and $Al_2O_3$ in an amount of 1 to 50% by weight of the catalyst.

In a particularly preferred process of the present invention for hydrogenating alkanoic acids, the catalyst comprises: a platinum group metal chosen from the group consisting of platinum, palladium and mixtures thereof on a silicaceous support chosen from the group consisting of high surface area high purity silica, and high surface area silica promoted with up to about 7.5 calcium metasilicate, the amount of platinum group metal present being at least about 2.0%, the amount of platinum present being at least about 1.5%; and the amount of tin promoter is between about 1% and 5% by weight of the catalyst, the mole ratio of platinum to tin being between about 3:2 and 2:3. Preferably, the high purity silica is pyrogenically generated, then tableted or pelleted into a form dense enough for use in a fixed bed catalyst. However, even in the case of high purity silica, presence of a stabilizer modifier, particularly calcium silicate, appears to extend, or stabilize, the activity and selectivity of the catalyst for prolonged periods extending into weeks, and even months, of commercially viable operation in the presence of acetic acid vapor at temperatures around 275° C. at space velocities of 2500 $hr^{-1}$ and higher. In particular, it is possible to achieve such a degree of stability that catalyst activity will decline by less than 10% over periods of a week (168 hours) or two (336 hours) or even over 500 hours. Accordingly, it can be appreciated that the catalysts of the present invention are fully capable of being used in commercial scale industrial applications for hydrogenation of acetic acid, particularly in production of high purity ethanol as well as mixtures of ethyl acetate and ethanol.

Another aspect of the invention relates to hydrogenation catalysts based on group VIII metals (Fe, Co, Ni, Ru, Rh, Pd, Ir, Pt and Os) or other transition metals (notably Ti, Zn, Cr, Mo and W) on oxidic supports incorporating basic non-volatile stabilizer-modifiers on the surface of or into the support itself in the form of oxides and metasilicates of alkaline earth metals, alkali metals, zinc, scandium, yttrium, precursors for the oxides and metasilicates, as well as mixtures thereof in amounts sufficient to: counteract acidic sites present on the surface thereof; impart resistance to shape change (primarily due to inter alia sintering, grain growth, grain boundary migration, migration of defects and dislocations, plastic deformation and/or other temperature induced changes in microstructure) at temperatures encountered in hydrogenation of acetic acid; or both.

In another embodiment of the process of the present invention, the catalyst is chosen from:
(i) catalysts combining a platinum group metal chosen the group consisting of platinum, palladium, and mixtures thereof with tin or rhenium on a siliceous support chosen from the group consisting of silica, calcium metasilicate and silica stabilized with and modified by calcium metasilicate;
(ii) catalysts combining palladium and rhenium supported on a siliceous support comprising chosen from the group consisting of, calcium metasilicate and calcium metasilicate promoted silica, the siliceous support being optionally promoted with one to 5% of a promoter chosen group consisting of: alkali metals; alkaline earth elements and zinc;
(iii) platinum promoted with cobalt on a siliceous support chosen from the group consisting of silica, calcium metasilicate and calcium metasilicate promoted silica; and
(iv) palladium promoted with cobalt on a siliceous support chosen from the group consisting of silica, calcium metasilicate and calcium metasilicate promoted silica.

In general, the siliceous support incorporates a promoter chosen from the group consisting of: stabilizer-modifiers comprising oxides and metasilicate of alkali metals; alkaline earth elements and zinc and precursors therefor in an amount of 1 to 5% by weight of the catalyst; a redox promoter chosen from the group consisting of: $WO_3$; $MoO_3$; $Fe_2O_3$ and $Cr_2O_3$ in an amount of 1 to 50% by weight of the catalyst; and an acidic modifier chosen from the group consisting of $TiO_2$; $ZrO_2$; $Nb_2O_5$; $Ta_2O_5$; and $Al_2O_3$ in an amount of 1 to 50% by weight of the catalyst, the presence of an acidic modifier favoring production of ethyl acetate in combination with ethanol.

Another aspect of the invention relates to a particulate catalyst for hydrogenation of alkanoic acids to the corresponding alkanol, comprising: a platinum group metal chosen from the group consisting of platinum, palladium and mixtures thereof on a siliceous support chosen from the group consisting of silica, silica promoted with up to about 7.5 calcium metasilicate and mixtures thereof, the surface area of the siliceous support being at least about 150 $m^2/g$; and a tin promoter in an amount of between about 1% and 2% by weight of the catalyst, the mole ratio of platinum to tin being between about 3:2 and 3:2, the siliceous support being optionally promoted with a promoter chosen from the group consisting of: an promoter chosen from the group consisting of alkali metals; alkaline earth elements and zinc in an amount of 1 to 5% by weight of the catalyst; a redox promoter chosen from the group consisting of: $WO_3$; $MoO_3$; $Fe_2O_3$ and $Cr_2O_3$ in an amount of 1 to 50% by weight of the catalyst; and an acidic modifier chosen from the group consisting of $TiO_2$; $ZrO_2$; $Nb_2O_5$; $Ta_2O_5$; and $Al_2O_3$ in an amount of 1 to 50% by weight of the catalyst.

An alternative embodiment of the present invention relates to a particulate hydrogenation catalyst consisting essentially of: a siliceous support having dispersed thereupon a platinum group metal chosen the group consisting of platinum, palladium, and mixtures thereof with a promoter chosen from the group consisting of tin, cobalt and rhenium, the siliceous support having a surface area of at least about 175 $m^2/g$ and being chosen from the group consisting of silica, calcium metasilicate and calcium metasilicate promoted silica; the siliceous support being optionally promoted with: 1% to 5% of a promoter chosen group consisting of alkali metals; alkaline earth elements and zinc in an amount of 1 to 5% by weight of the catalyst; a redox promoter chosen from the group consisting of: $WO_3$; $MoO_3$; $Fe_2O_3$ and $Cr_2O_3$ in an amount of 1 to 50% by weight of the catalyst; and an acidic modifier chosen from the group consisting of $TiO_2$; $ZrO_2$; $Nb_2O_5$; $Ta_2O_5$; and $Al_2O_3$ in an amount of 1 to 50% by weight of the catalyst. In one more preferred embodiment of the present invention, the total weight of platinum group metals present is between 2 and 4%, the amount of platinum present is at least 2%, the promoter is tin, the mole ratio of platinum to tin being between 2:3 and 3:2, and the amount of calcium metasilicate is between 3 and 7%. In another more preferred embodiment of the present invention, the total weight of platinum group metals present is between 0.5% and 2%, the amount of palladium present is at least 0.5%, the promoter is rhenium, the weight ratio of rhenium to palladium being between 10:1 and 2:1, and the amount of calcium metasilicate is between 3 and 90%. In a third more preferred embodiment of the present invention, the total weight of platinum group metals present is between 0.5 and 2%, the amount of platinum present is at least 0.5%, the promoter is cobalt, the weight ratio of cobalt to platinum being between 20:1 and 3:1, and the amount of calcium silicate is between 3 and 90%. In a fourth more preferred embodiment of the present invention, the total weight of platinum group metals present is between 0.5 and 2%, the amount of palladium present is at least 0.5%, the promoter is cobalt, with the weight ratio of cobalt to palladium being between 20:1 and 3:1, and the amount of calcium silicate between 3 and 90%.

BRIEF DESCRIPTION OF DRAWINGS

The invention is described in detail below with reference to the appended drawings, wherein like numerals designate similar parts. In the drawings.

DETAILED DESCRIPTION OF THE INVENTION

Even though market conditions constantly fluctuate, for large scale operations, the selectivities, activities and catalyst life reported in the literature for catalytic hydrogenation of acetic acid to ethanol imply economics generally unfavorable to those needed to compete with other methods of ethanol production. One estimate of productivity needed for commercial viability has concluded that selectivity for ethanol in excess of about 50% with a productivity of about 200 g of ethanol per kg of catalyst per hour would be needed. The catalysts of the present invention far exceed those requirements.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range as well as any sub-range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Figure 1:
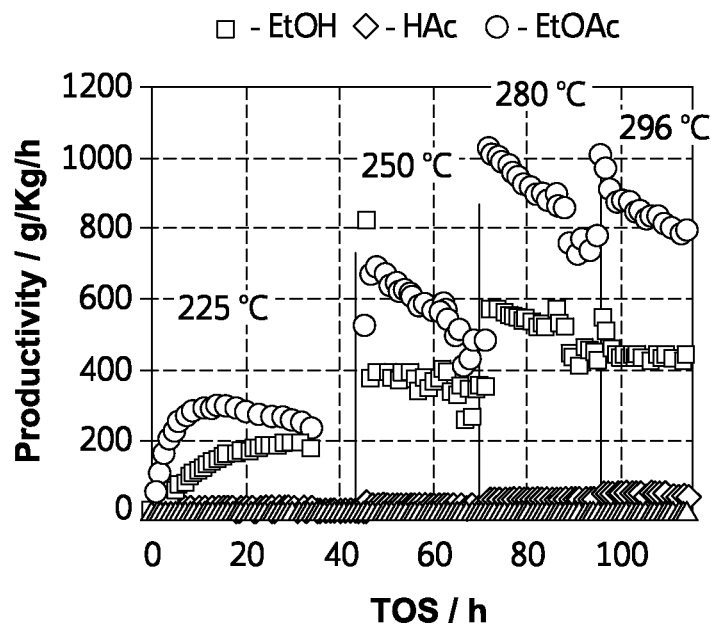
FIGS. 1 and 2 illustrate the selectivity and productivity performance of catalysts of the present invention.
Figure 2:
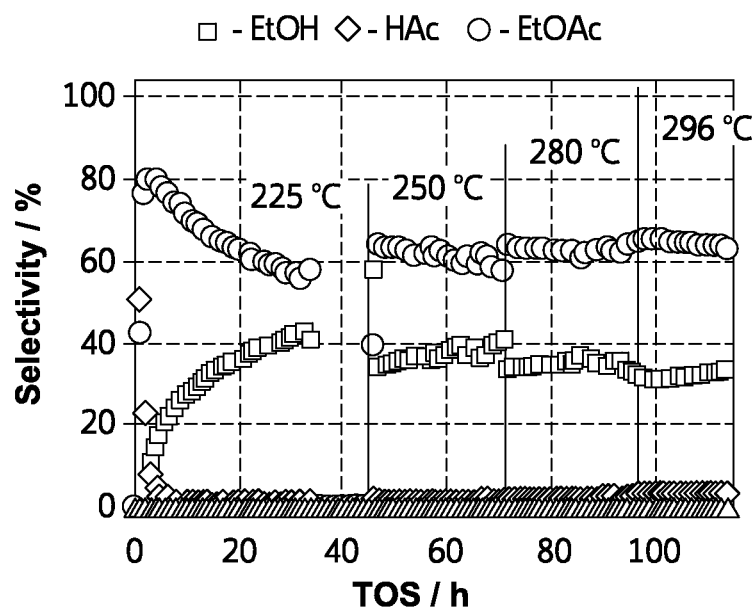

FIGS. 1 and 2 illustrate the selectivity and productivity performance of catalysts of the present invention, graphically presenting the greatly improved selectivity and productivity attainable with these catalysts at a variety of operation temperatures. Notably, at 280° C. and 296° C., the selectivity for ethanol is about 60%. In evaluating this, it is important to recall that ethyl acetate is also a commodity of considerable economic importance and value so that, even if the primary goal is production of ethanol, any acetic acid converted to ethyl acetate retains considerable value, whereas any alkanes produced as by-products are generally much lower in value than the feedstock. In FIG. 1, productivity in terms of grams of ethanol produced per kilogram of catalyst per hour onstream are represented as a function of time (in hours) by squares, while productivity of ethyl acetate is represented by circles, and the productivity of acetaldehyde is represented by diamonds. Significantly during this run, the operating temperature was increased as indicated during the run to demonstrate the effect of operating temperature upon productivity and selectivity. In FIG. 2, the selectivity for ethanol as hereinafter defined is represented by circles as a function of time onstream while the selectivity for ethyl acetate as hereinafter defined is represented by squares and the selectivity for acetaldehyde by diamonds.

Figure 3A:
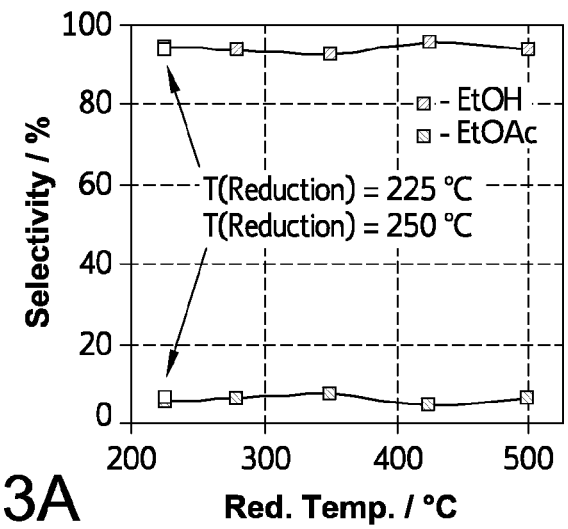
FIGS. 3A-3C illustrate the relative temperature insensitivity of the selectivity and productivity of catalysts of the present invention along with the variation in properties obtained when acetic acid is hydrogenated at 225° C. over catalyst activated at 225° C.
Figure 3B:
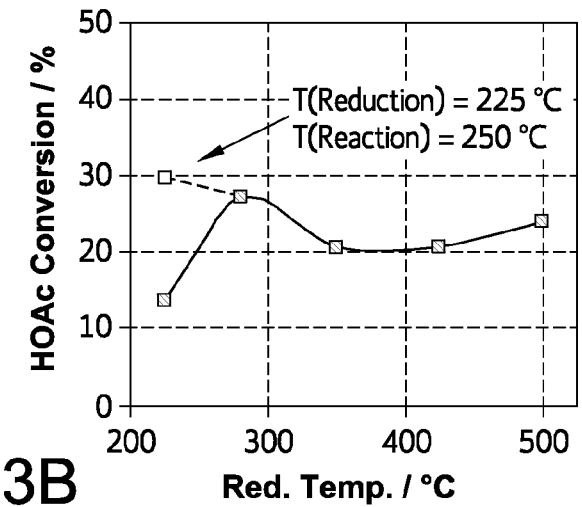
Figure 3C:
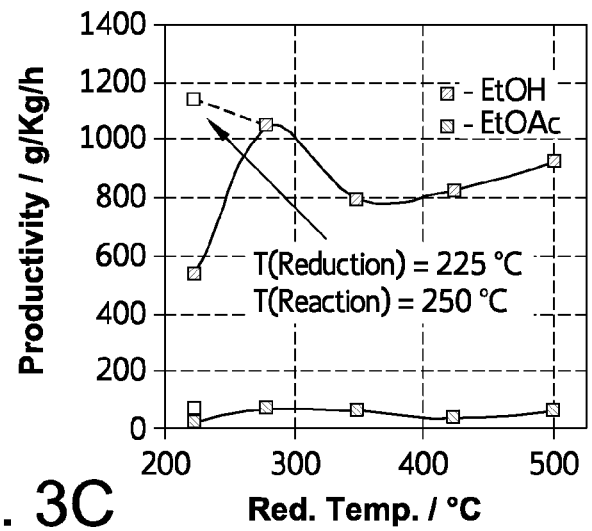

FIGS. 3A-3C illustrate the relative temperature insensitivity of the selectivity of catalysts of the present invention to the temperature at which the metal precursors are reduced. This characteristic is significant to commercial viability as it is possible to conduct the reaction in a vessel which is not specially configured to maintain uniform temperature throughout, typically these vessels are referred to as "adiabatic reactors" as there is little provision made for accommodating the temperature changes accompanying the reaction process although it is common to "dilute" the catalyst with quartz chips or other inert particles to moderate the reaction. FIG. 3A, reports the results of an experiment in which catalyst was reduced at the temperatures indicated in ° C. and hydrogen and acetic acid thereafter hydrogenated over that catalyst at 250° C. The upper line indicates the selectivity of that particular catalyst for ethanol while the lower line represents the selectivity for ethyl acetate. In FIG. 3B, the productivity results for that experiment are presented in which the upper line reports the productivity of ethanol and the lower line the productivity of ethyl acetate. In FIG. 3C, the conversion (as hereinafter defined) results for that experiment are presented as a function of reduction temperature. In addition, acetic acid was also hydrogenated at a temperature of 225° C. over the catalyst reduced or activated at 225° C. Points on FIGS. 3B and 3C are also included present results of that experiment in which acetic acid was hydrogenated at 225° C. over the catalyst reduced at 225° C. It can be appreciated that hydrogenation over this catalyst at a temperature of 225° C. results in decreased selectivity to ethanol and decreased conversion.

Figure 4A:
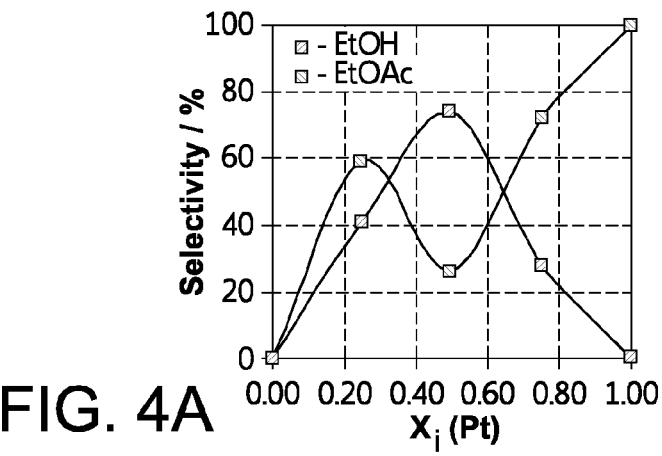
FIGS. 4A-4C illustrate the variations in selectivity, conversion and productivity incumbent upon changes in the ratio of platinum to tin the preferred platinum tin catalysts of the present invention.
Figure 4B:
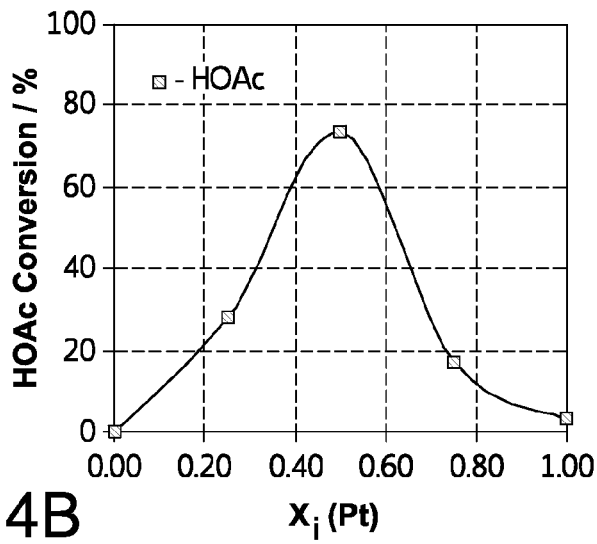
Figure 4C:
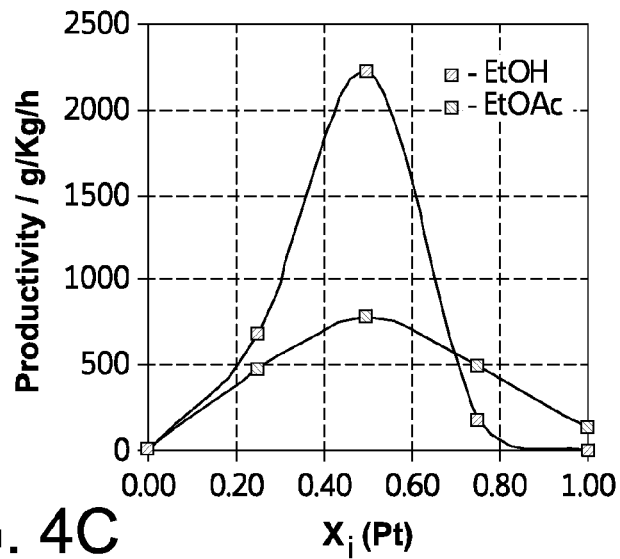

FIGS. 4A-4C illustrate the variations in selectivity, conversion and productivity incumbent upon changes in the ratio of platinum to tin in the preferred platinum tin catalysts of the present invention in correlation with the mol fraction of Pt in $SiO_2$—$Pt_xSn_{(1-x)}$($\Sigma$[Pt]+[Sn]=1.20 mmol) in the catalytic hydrogenation of acetic acid using 2.5 ml solid catalyst (14/30 mesh, diluted 1:1 (v/v, with quartz chips, 14/30 mesh); at an operating pressure p=200 psig (14 bar); feed rates of acetic acid, hydrogen and nitrogen diluents of 0.09 g/min HOAc; 160 sccm/min $H_2$; and 60 sccm/min $N_2$ respectively; the overall space velocity, GHSV, being 6570 $h^{-1}$ over 12 h of reaction time. It can be appreciated that, in this experiment, selectivity to production of ethanol is maximized at a mole ratio of about 1 to 1 for those catalysts supported on essentially pure high surface area silica. (Throughout this specification, lower case script "l" is used for liter to avoid the ambiguity resulting from the similarity or even identity of the symbols used for the numeral one and the lower case twelfth letter of the Roman alphabet in many typefaces.) On each of FIGS. 4A-4C, $X_i$(Pt) on the horizontal access axis represents the mass fraction of platinum in the catalyst ranging between zero and one while selectivity, conversion and productivity are as indicated previously with FIG. 4A representing the selectivity of the catalyst toward ethanol and ethyl acetate, with the selectivity for ethanol peaking at a mass fraction of 50% where, as shown in FIG. 4B, the conversion of acetic acid also peaks as does the productivity of ethanol as shown in FIG. 4C.

Figure 5A:
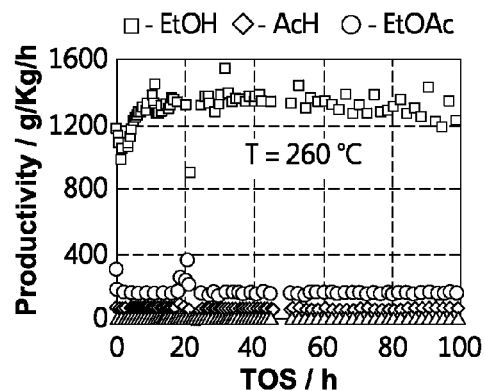
FIGS. 5A and 5B illustrate the selectivity of the most preferred catalysts the present invention supported on high surface area silica for ethanol production as well as the high productivity obtained therewith.

FIGS. 5A and B illustrate the selectivity and productivity of the most preferred catalysts the present invention supported on high surface area silica for ethanol production as well as the high productivity obtained therewith. In FIG. 5A, productivity in grams per kilogram of catalyst per hour onstream are indicated on the vertical axis wherein productivity for ethanol is represented by squares, productivity of ethyl acetate is represented by circles and productivity of acetaldehyde is represented by diamonds. Similarly in FIG. 5B, selectivity as hereinafter defined is presented on the vertical axis as a function of time onstream in hours on the horizontal axis with selectivity to ethyl acetate again being in represented by circles, selectivity to ethanol being represented by squares and selectivity to acetaldehyde being represented by diamonds.

Figure 6A:
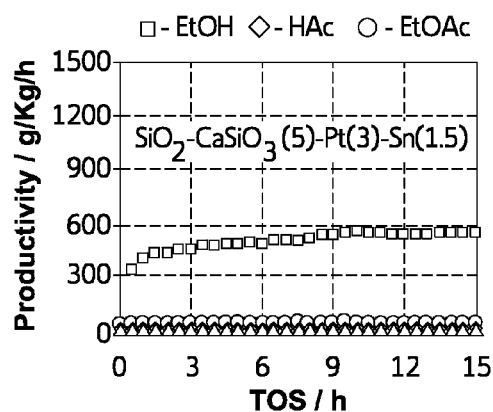
FIGS. 6A and 6B, and FIGS. 7A and 7B illustrate the excellent selectivity obtained at low temperature using the most preferred catalysts the present invention based on calcium metasilicate promoted high surface area silica. It can be appreciated that the selectivity for ethanol is high.
Figure 6B:
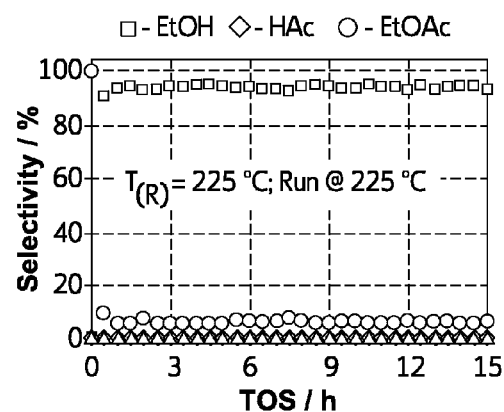
Figure 7A:
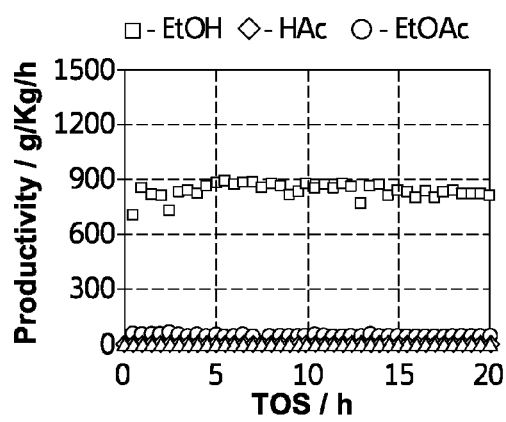

FIGS. 6 A and B, and FIGS. 7A and B illustrate the selectivity obtained at low temperature using a preferred catalyst the present invention based on calcium metasilicate promoted high surface area silica using the same format as FIGS. 5A and B. It can be appreciated that the selectivity for ethanol is over 90% throughout the run.

FIGS. 8-12 are discussed in connection with the relevant examples.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning, "%" and like terms referring to weight percent unless otherwise indicated. In general, when the composition of a support is being discussed, the percentages in the composition include the oxygen as well as the ions or metals attached thereto, while when weights of catalytic metals are discussed, the weight of oxygen attached thereto is ignored. Thus, in a support comprising 95% silica and 5% alumina, this composition is based on alumina having a formula weight of 101.94 and silica having a formula weight of 60.09. However, when we refer to a catalyst as having 2% platinum and 3% tin, the weight of any oxygen which may be attached thereto is ignored.

"Conversion" is expressed as a mole percentage based on acetic acid in the feed.

AcOH conversion (%) =
$$100 * \frac{mmol \text{ AcOH in (feed stream)} - mmol \text{ AcOH out } (GC)}{mmol \text{ AcOH in (feed stream)}}$$

"Selectivity" is expressed as a mole percent based on converted acetic acid. For example, if the conversion is 50 mole % and 50 mole % of the converted acetic acid is converted to ethanol, we refer to the ethanol selectivity as 50%. Ethanol selectivity is calculated from gas chromatography (GC) data as follows:

Selectivity to EtOH (%) =
$$100 * \frac{mmol \text{ EtOH out } (GC)}{\frac{\text{Total } mmol \text{ } C \text{ out } (GC)}{2} - mmol \text{ AcOH out } (GC)}$$

Without intending to be bound by theory, it is believed the conversion of acetic acid to ethanol in accordance with the invention involves one or more of the following reactions:

Hydrogenation of Acetic Acid to Ethanol.

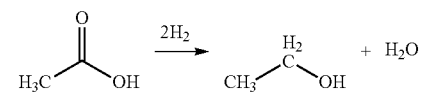

Hydrogenation of Acetic Acid to Ethyl Acetate

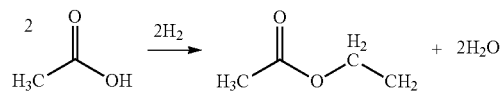

Cracking of Ethyl Acetate to Ethylene and Acetic Acid

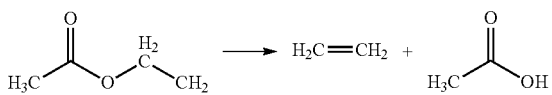

Dehydration of Ethanol to Ethylene

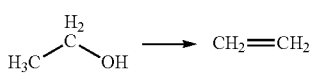

Selective catalysts for catalytic hydrogenation of acetic acid to ethanol are those chosen the group consisting of:
  (i) catalysts combining a platinum group metal chosen the group consisting of platinum, palladium, and mixtures thereof with tin or rhenium on silicaceous supports chosen from the group consisting of silica, calcium metasilicate, or silica promoted with calcium metasilicate;
  (ii) catalysts combining palladium and rhenium supported on a silicaceous support as described above optionally promoted with one to 5% of a first promoter chosen group consisting of: alkali metals; alkaline earth elements and zinc, promoter being preferably added to the catalyst formulation in the form of the respective nitrates or acetates, of the these promoters, particularly preferred are potassium, cesium, calcium, magnesium and zinc;
  (iii) platinum promoted with cobalt on a silicaceous support; and
  (iv) palladium promoted with cobalt on a silicaceous support.

The process of the invention may be practiced in a variety of configurations using a fixed bed reactor or a fluidized bed reactor as one of skill in the art will readily appreciate. In many embodiments of the present invention, an "adiabatic" reactor can be used, i.e., there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchange inbetween. It is considered significant that acetic acid reduction processes using the catalysts of the present invention may be carried out in adiabatic reactors as this reactor configuration is typically far less capital intensive than tube and shell configurations.

Various catalyst supports known in the art can be used to support acetic acid hydrogenation catalysts. Examples of such supports include without any limitation, iron oxide, silica, alumina, titania, zirconia, magnesium oxide, calcium silicate, carbon, graphite and mixtures thereof. We prefer use of a silicaceous support chosen from the group consisting of silica, calcium metasilicate and silica promoted with calcium silicate for the present invention, with pyrogenic silica having an $SiO_2$ content of at least 99.7% being especially desirable when pelletized into a form dense enough for use in fixed bed reactors. We have found that high purity, high surface area silica, especially grade HSA SS 61138 from Saint-Gobain N or Pro, optionally promoted with calcium metasilicate is unexpectedly superior to other supports for the catalysts of the present invention. It is preferred that silica used as a support in the present invention have a surface area of at least 100 $m^2/g$, more preferably at least 150 $m^2/g$, more preferably at least 200 $m^2/g$ and most preferably about 250 $m^2/g$. Throughout this specification, the term "high surface area silica" should be understood to signify silica having a surface area of at least 250 $m^2/g$. The activity/stability of the silicaceous support may be modified by inclusion of minor amounts other constituents as described hereinbelow. Any convenient particle shape including pellets, extrudates, spheres, spray dried, rings, pentarings, trilobes and quadrilobes may be used, although for this application we generally prefer to use cylindrical pellets.

to the small pores may also be contributing to the acid-catalyzed formation of diethylether by ethanol dehydration. The addition of a basic modifier to any of the supports studied resulted generally in an increase of the selectivity towards ethanol, accompanied by a significant reduction of the acetic acid conversion. The highest selectivity for ethanol with 92% was found for $SiO_2$—$CaSiO_3$(5)-Pt(3)-Sn(1.8), Table A, entry 2, and even pure $TiO_2$, promoted with $CaSiO_3$ produced ethanol with a selectivity of about 20%. A comparison between $SiO_2$—$TiO_2$ and $TiO_2$—$CaSiO_3$ suggests that the site density of the acidic (Lewis) sites may also be of importance, and further optimization of the acidic properties of the catalyst supports can most likely be achieved by careful variation of basic and acidic promoters combined with specific methods of preparation.

TABLE A

Summary of catalyst activity data for catalyst support modifiers in the gas-phase hydrogenation of acetic acid. Reaction Conditions: 2.5 ml solid catalyst (14/30 mesh, diluted 1:1 (v/v, with quartz chips, 14/30 mesh); p = 200 psig (14 bar); 0.09 g/min HOAc; 160 sccm/min $H_2$; 60 sccm/min $N_2$; GHSV = 6570 $h^{-1}$; 12 h of reaction time.

| Entry No. | Catalyst[1] | Product Selectivity (%)[2] | | | HOAc[3] Conv. (%) |
|---|---|---|---|---|---|
| | | AcH | EtOH | EtOAc | |
| 1 | $SiO_2$—$Pt_xSn_{1-x}$; x = 0.50 | — | 74 | 26 | 73 |
| 2 | $SiO_2$—$CaSiO_3$(5)-Pt(3)-Sn(1.8) | 2 | 92 | 6 | 24 |
| 3 | $SiO_2$—$WO_3$(10)-Pt(3)-Sn(1.8) | — | 77 | 23 | 17 |
| 4 | $SiO_2$—$TiO_2$(10)-Pt(3)-Sn(1.8) | — | 47 | 53 | 73 |
| 5 | $TiO_2$—$CaSiO_3$(5)-Pt(3)-n(1.8) | — | 22 | 78 | 38 |
| 6 | KA160-Pt(3)-Sn(1.8) | 1 | 47 | 52 | 61 |
| 7 | KA160-$CaSiO_3$(8)-Pt(3)-Sn(1.8) | 1 | 84 | 15 | 43 |
| 8 | (H-ZSM-5)-Pt(3)-Sn(1.8)[4] | — | — | 4 | 78[4] |
| 9 | $SiO_2$—$Re_xPd_{1-x}$; x = 0.75 | — | — | 56 | 44 | 9 |
| 10 | $SiO_2$—$CaSiO_3$(5)-Re(4.5)-Pd(1) | — | 83 | 17 | 8 |

[1]The preparation of the individual catalysts is described in detail herein. The numbers in parentheses represent the amount of the actual component (metal, metal oxide) in wt %.
[2]Product selectivity (wt %) was calculated by from authentic sample calibrated GC analyses.
[3]The acetic acid conversion (%) was calculated by: [HOAc] Conversion, % = {[HOAc] (Feed, mmol/min) − [HOAc] (Effluent, mmol/min)/[HOAc] (Feed, mmol/min)} * 100.
[4]The main product obtained with this catalyst is diethyl ether, EtOEt, with a selectivity of 96%, and a productivity of 2646 g/kg/h.

Influence of the Catalyst Suppport.

Aside from the choice of metal precursor (i.e., halogen, $Cl^-$ vs. halogen-free, $NO_3^-$) and preparation conditions, the resulting metal-support interactions strongly depend on structure and properties of the underlying support.

The effects of basic and acidic modifiers was studied for a variety of silica-supported Pt—Sn materials. The molar ratio between Pt and Sn was maintained at 1:1 for all materials, and the total metal loading was also kept constant unless stated otherwise. Notably, the catalysts prepared on acidic supports, such as $SiO_2$, $SiO_2$—$TiO_2$, KA160 (i.e., $SiO_2$—$Al_2O_3$), and H-ZSM5 give rise to high conversions in acetic acid, but lower selectivity towards ethanol. Interestingly, the H-ZSM5 catalyst actually produces diethylether as the main product, most likely formed by dehydration from ethanol. Both the catalysts based on $SiO_2$—$TiO_2$ and KA160 (i.e., $SiO_2$—$Al_2O_3$) give high conversions and similar selectivities for EtOH and EtOAc with EtOAc being the main product in both cases. It appears, that the presence of Lewis acidity in the underlying catalyst support may be beneficial for higher conversions of acetic acid. While the acidity in $SiO_2$—$TiO_2$ is mainly based on Lewis acidity, the KA160 (silica-alumina) material also has strongly acidic Bronsted sites which can catalyze the formation of EtOAc from residual acetic acid and EtOH. The catalyst based on H-ZSM5 has even more strongly acidic, zeolytic Bronsted sites, and the shape selectivity due A significant shift in selectivity towards ethanol was observed comparing KA160 ($SiO_2$-5% $Al_2O_3$) with the KA160-$CaSiO_3$—promoted catalyst. Although at 84%, the selectivity with this catalyst is still lower than that observed for the $SiO_2$—$CaSiO_3$—based material, conversion of acetic acid remains at 43%, almost double of that seen for $SiO_2$—$CaSiO_3$ (5)-Pt(3)-Sn(1.8), see Table A, entries 2, 6 and 7. In addition to the "acidic modifier" properties, all $CaSiO_3$—promoted materials appear to show improved longer-term stability (albeit at lower conversions). Specifically, the $SiO_2$—$CaSiO_3$ (5)-Pt(3)-Sn(1.8) catalyst exhibited less than 10% activity decrease over more than 220 hrs of reaction time under various reaction conditions. The two Re—Pd catalysts, prepared on $SiO_2$ and $SiO_2$—$CaSiO_3$ also show similar trends with respect to selectivity. Althoug the conversion remained below 10% for both materials, a significant shift in selectivity towards ethanol was observed for the $CaSiO_3$—promoted material, Table A, entries 9 and 10. Additional information on productivities is provided in Table 4.

Accordingly, without being bound by theory, modification and stabilization of oxidic supports for acetic acid hydrogenation catalysts by incorporation of non-volatile stabilizer-modifiers having either the effect of: counteracting acid sites present upon the surface thereof; or the effect of thermally stabilizing the surface makes it possible to achieve desirable improvements in selectivity to ethanol, prolonged catalyst life; or both. In general, modifiers based on oxides in their most stable valence state will have low vapor pressure and thus are rather non-volatile. Accordingly, it is preferred that hydrogenation catalysts based on group VIII metals (Fe, Co, Ni, Ru, Rh, Pd, Ir, Pt and Os) or other transition metals (notably Ti, Zn, Cr, Mo and W) on oxidic supports incorporate basic non-volatile stabilizer-modifiers on the surface of or into the support itself in the form of oxides and metasilicates of alkaline earth metals, alkali metals, zinc, scandium, yttrium, precursors for the oxides and metasilicates, and mixtures thereof in amounts sufficient to counteract acidic sites present on the surface thereof, impart resistance to shape change (primarily due to inter alia sintering, grain growth, grain boundary migration, migration of defects and dislocations, plastic deformation and/or other temperature induced changes in microstructure) at temperatures encountered in hydrogenation of acetic acid; or both.

The amount of metal loading on support is not extremely critical in this invention and can vary in the range of about 0.3 weight percent to about 10 weight percent. A metal loading of about 0.5 weight percent to about 6 weight percent based on the weight of the catalyst is particularly preferred. Due to extreme costliness, platinum group metals are typically used in rather carefully controlled amounts, often less than 10% by weight of the entire catalytic composition. As little as 0.25-5% platinum, when combined with the other catalytic elements as described herein, can provide excellent selectivity, life and activity. Typically, we prefer using between 0.5-5%, more preferably 1-3% platinum in the platinum containing catalysts of the present invention. In the case of platinum tin catalysts, we prefer to use from 0.10 to 5% tin, more preferably 0.25 to 3% tin, still more preferably 0.5 to 2.5% tin and most preferably a combination of about 3% platinum and about 1.5% tin corresponding rather closely to a 1:1 molar ratio of platinum to tin when supported on high surface area silica/calcium metasilicate or lesser proportionate amounts based on lower weight percentage of platinum. For this catalyst, we prefer to use a silicaceous support chosen from the group consisting of high purity high surface area silica as described above, calcium metasilicate and high surface area silica promoted with calcium metasilicate. Accordingly, it can be appreciated that the amount of calcium metasilicate can vary widely ranging from 0 up to 100% by weight. As the calcium metasilicate tends to have lower surface area, we prefer to include at least about 10% high surface area silica in our supports for this catalyst, more preferably as our support, we prefer to use approximately 95% high surface area silica, SS61138 High Surface Area (HSA) Silica Catalyst Carrier from Saint-Gobain N or Pro having a surface area of 250 $m^2/g$; a median pore diameter of 12 nm; a total pore volume of 1.0 $cm^3/g$ as measured by mercury intrusion porosimetry and a packing density of about 22 $lbs/ft^3$.

Catalysts of the present invention are particulate catalysts in the sense that, rather than being impregnated in a wash coat onto a monolithic carrier similar to automotive catalysts and diesel soot trap devices, our catalysts are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. Spheres, spray dried microspheres, rings, penta-rings and multi-lobal shapes are all usable. Typically, the shapes are chosen empirically based upon perceived ability to contact the vapor phase with the catalytic agents effectively.

A highly suitable platinum tin catalyst comprises about 3% platinum, 1.5% tin by weight supported on a high surface area silica having a surface area of about 250 $m^2/g$ promoted with from about 0.5% to 7.5% calcium metasilicate. We have already achieved catalyst life in the hundreds of hours of time on stream at 280° C. with this composition. In many cases, it will be possible to partially substitute palladium for platinum in the above mentioned compositions.

Catalyst similar to those described in the preceding paragraph but containing lesser amounts of the extremely costly platinum promoted with rather large amounts of cobalt provide good initial catalytic activities but tend not to exhibit as prolonged catalyst lives as the platinum tin catalysts described above. The hierarchy of preference for silicaceous support for this catalyst is essentially the same as that for the platinum tin catalysts. Preferred catalysts of this class include from 0.25 to 5% platinum, more preferably 0.3 to 3% platinum, most preferably 0.5 to 1.5% platinum combined with from about 1% to about 20% cobalt, more preferably from about 2% to about 15% cobalt and more preferably from about 8 to 12% cobalt. Even though these catalysts are not so durable as the platinum tin catalysts described above, in many cases, this will be largely offset by the greatly decreased amount of platinum required, the lower cost of cobalt as compared to the platinum group metals and the excellent initial selectivity. It is, of course, well understood that in many cases, it is possible to compensate for lack of activity by appropriate recycle streams or use of larger reactors, but it is more difficult to compensate for poor selectivity.

Catalysts based on palladium promoted with rhenium or cobalt provide excellent catalytic activity with somewhat lower selectivity, this loss of selectivity being aggravated at reaction temperatures above 280° C. resulting in the formation of increased amounts of acetaldehyde, carbon dioxide and even hydrocarbons. The cobalt containing catalysts typically exhibit slightly better selectivity than the corresponding rhenium catalyst; but, while both provide surprisingly long-lived catalytic activity, neither provides catalyst life which is as outstanding as of that of the most preferred platinum/tin catalysts on high purity alumina stabilized with and modified by calcium metasilicate. Again this catalyst may be supported on the silicaceous supports stabilized with and modified by the oxides and metasilicates of Group I, Group II and zinc described above as well as the precursors therefor and mixtures thereof. Highly suitable precursors include the acetates and nitrates of zinc, the alkali metals and the alkaline earth metals which may optionally be incorporated into the silicaceous support in the amount of about 1 to 5% based on the weight of the metal excluding the acetate and/or nitrate moieties.

In other embodiments of the present invention, the catalysts described above may be modified by incorporating modifiers chosen from the group consisting of redox-active modifiers; acidic modifiers and mixtures thereof into the silicaceous support thereby changing the relative selectivity between ethanol, ethyl acetate and acetaldehyde. Suitable redox-active modifiers include $WO_3$; $MoO_3$; $Fe_2O_3$ and $Cr_2O_3$ while acidic modifiers include $TiO_2$; $ZrO_2$; $Nb_2O_5$; $Ta_2O_5$; and $Al_2O_3$. By judicious incorporation of these modifiers into the silicaceous support, the activity of the catalyst may be tuned to produce more desirable distributions of relative amounts of the products the catalytic hydrogenation to accord with fluctuations in markets and the demands for the various products. Typically, these materials will be included in the silicaceous support in amounts ranging from about 1 to 50% by weight thereof.

The metal impregnation can be carried out using any of the known methods in the art. Typically, before impregnation, the supports are dried at 120° C. and shaped to particles having size distribution in the range of about 0.2 to 0.4 mm. Optionally, the supports may be pressed, crushed and sieved to a desired size distribution. Any of the known methods to shape the support materials into desired size distribution can be employed. In a preferred method of preparing the catalyst, a platinum group metal component such as a suitable compound and/or complex of the platinum group metals can be utilized to achieve dispersion of the catalytic component on the support, e.g., support particles. Water soluble compounds or water dispersible compounds or complexes of platinum group metals can be utilized to impregnate or deposit the catalytic metal compounds onto support particles. The platinum group metal component decomposes upon heating and/or the application of vacuum. In some cases, the completion of removal of the liquid may not take place until the catalyst is placed into use and subjected to the high temperatures encountered during operation. Generally, both from the point of view of economics and environmental aspects, aqueous solutions of soluble compounds of the platinum group metals are preferred. For example, suitable compounds are chloroplatinic acid, amine solubilized platinum hydroxide, palladium nitrate or palladium chloride, sodium palladium chloride, sodium platinum chloride and the like, although we prefer to avoid use of halogens when ethanol is the desired product. During the calcination step, or at least during the initial phase of use of the catalyst, such compounds are converted into a catalytically active form of the platinum group metal or a catalytically active oxide thereof. In general however, we prefer to use platinum group metal precursors which are chloride free as we have found that catalysts prepared from $Pt(NH_3)_4(NO_4)_2$ seem to exhibit increased selectivity to ethanol.

Inasmuch as the catalysts of the present invention are bimetallic, is generally considered that, in such cases, one metal acts as a promoter metal and the other metal is the main metal. For instance, in the case of the platinum tin catalyst, platinum might be considered to be the main metal for preparing hydrogenation catalysts of this invention, while tin would be considered a promoter metal. However, it should be noted that sometimes such distinctions can be deceptive particularly in this case wherein the selectivity of platinum tin catalyst for ethanol, the desired product, approaches zero both in the absence of tin and in the absence of platinum. For convenience, we prefer to refer to the platinum group metal or metals as the primary catalyst and the other metals as the promoters. This should not be taken as an indication of the underlying mechanism of the catalytic activity.

Bimetallic catalysts are often impregnated in two steps. First, the "promoter" metal is added, followed by "main" metal. Each impregnation step is followed by drying and calcination. Bimetallic catalysts may also be prepared by co-impregnation. In the case of promoted bimetallic catalysts as described above, a sequential impregnation may be used, starting with the addition of the "promoter metal followed by a second impregnation step involving co-impregnation of the two principal metals, i.e., Pt and Sn. For example, PtSn/$CaSiO_3$ on $SiO_2$ may be prepared by a first impregnation of $CaSiO_3$ onto the $SiO_2$, followed by the co-impregnation with dilute admixtures of chloroplatinic acid, amine solubilized platinum hydroxide, palladium nitrate or palladium chloride, sodium palladium chloride, sodium platinum chloride, $Pt(NH_3)_4(NO_4)_2$ and the like. Again, each impregnation is followed by drying and calcinations. In most cases, the impregnation may be carried out using metal nitrate solutions. However, various other soluble salts which upon calcination releases metal ions can also be used. Examples of other suitable metal salts for impregnation include, metal acids, such as perrhenic acid solution, metal oxalate, and the like. In those cases where substantially pure ethanol is to be produced, it is generally preferable to avoid the use of halogenated precursors for the platinum group metals, using the nitrogenous amine and/or nitrate based precursors instead.

The reaction may be carried out in the vapor state under a wide variety of conditions. Preferably, the reaction is carried out in the vapor phase. Reaction temperatures may be employed, for example in the range of about 125° C. to 350° C., more commonly from about 200° C. to about 325° C., preferably from about 225° C. to about 300° C. and most preferably from about 250° C. to about 300° C. The pressure is generally uncritical to the reaction and subatmospheric, atmospheric or superatmospheric pressures may be employed. In most cases, however, the pressure of the reaction will be in the range of about 1 to 30 atmospheres absolute. In another aspect of the process of this invention, the hydrogenation typically can be carried out at a pressure just sufficient to overcome the pressure drop across the catalytic bed at the gross hourly space velocity ("GHSV") selected, although there is no bar to the use of higher pressures, it being understood that considerable pressure drop through the reactor bed may be experienced at the space velocities of 5000 $hr^{-1}$ and 6,500 $hr^{-1}$ easily usable with the catalysts of the present invention.

Although the reaction consumes two moles of hydrogen per mole of acetic acid to produce a mole of ethanol, the actual molar ratio of hydrogen to acetic acid in the feed stream may be varied between wide limits, e.g. from about 100:1 to 1:100. It is preferred however that such ratio be in the range of about 1:20 to 1:2. Most preferably, the molar ratio of hydrogen to acetic acid is about 5:1.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas fluctuate becoming either more or less expensive, methods for producing acetic acid and intermediates such as methanol and carbon monoxide from alternate carbon sources have drawn increasing interest. Particularly, when petroleum is relatively expensive compared to natural gas, it may become advantageous to produce acetic acid from synthesis gas ("syn gas") that derived from any suitable carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas.

The syn gas is converted to methanol which may be carbonylated to acetic acid. The method likewise produces hydrogen which may be used in connection with this invention as noted above. See also, U.S. Pat. No. 5,821,111 Grady et al., which discloses a process for converting waste biomass through gasification into synthesis gas as well as U.S. Pat. No. 6,685,754 Kindig et al., the disclosures of which are incorporated herein by reference.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 of Scates et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material such as glass wool to regulate the pressure drop of the reactant stream through the catalyst bed and the contact time of the reactant compounds with the catalyst particles.

The following examples describe the procedures used for the preparation of various catalysts employed in the process of this invention. Throughout these Preparations and Examples, where a lower case or minuscule script "l" is used, it is used to avoid ambiguity between the lower case letter "l", the numeral "1" and the upper case or majuscule letter "I" inherent in many fonts and/or typefaces and, since the meaning of language flows from common usage, should be understood to indicate "liters" or "litres" despite the lack of any international sanction therefor.

Catalyst Preparations (General).

The catalyst supports were dried at 120° C. overnight under circulating air prior to use. All commercial supports (i.e., $SiO_2$, $ZrO_2$) were used as a 14/30 mesh, or in its original shape (1/16 inch or 1/8 inch pellets) unless mentioned otherwise. Powdered materials (i.e., $CaSiO_3$) were pelletized, crushed and sieved after the metals had been added. The individual catalyst preparations are described in detail in the following Section.

Catalyst Preparation A

Preparation of 0.5 wt % Platinum and 5 wt % Tin on High Purity Low Surface Area Silica Powdered and meshed high surface area silica NPSG SS61138 (100 g) of uniform particle size distribution of about 0.2 mm was dried at 120° C. in an oven under nitrogen atmosphere overnight and then cooled to room temperature. To this was added a solution of platinum nitrate (Chempur) (0.82 g) in distilled water (8 ml) and a solution of tin oxalate (Alfa Aesar) (8.7 g) in dilute nitric acid (1N, 43.5 ml). The resulting slurry was dried in an oven gradually heated to 110° C. (>2 hours, 10° C./min.). The impregnated catalyst mixture was then calcined at 500° C. (6 hours, 1° C./min).

Catalyst Preparation B

Preparation of 1 wt. % Platinum and 1 wt. % Tin on High Surface Area Silica

The procedures of Catalyst Prep A was substantially repeated except for utilizing a solution of platinum nitrate (Chempur) (1.64 g) in distilled water (16 ml) and a solution of tin oxalate (Alfa Aesar) (1.74 g) in dilute nitric acid (1N, 8.5 ml).

Catalyst Preparation C

Preparation of 1 wt. % Platinum and 1 wt. % Tin on Calcium Meta-Silicate

The procedures of Catalyst Prep B was substantially repeated except for utilizing a solution of platinum nitrate (Chempur) (1.64 g) in distilled water (16 ml) and a solution of tin oxalate (Alfa Aesar) (1.74 g) in dilute nitric acid (1N, 8.5 ml), and utilizing calcium meta-silicate as a catalyst support.

Catalyst Preparation D

Preparation of 0.5 wt. % Platinum, 0.5 wt. % Tin and 0.2 wt. % Cobalt on High Surface Area Silica Powdered and meshed high surface area silica (100 g) of uniform particle size distribution of about 0.2 mm was dried at 120° C. in an oven under nitrogen atmosphere overnight and then cooled to room temperature. To this was added a solution of platinum nitrate (Chempur) (0.82 g) in distilled water (8 ml) and a solution of tin oxalate (Alfa Aesar) (0.87 g) in dilute nitric acid (1N, 4.5 ml). The resulting slurry was dried in an oven gradually heated to 110° C. (>2 hours, 10° C./min.). The impregnated catalyst mixture was then calcined at 500° C. (6 hours, 1° C./min). To this calcined and cooled material was added a solution of cobalt nitrate hexahydrate (0.99 g) in distilled water (2 ml). The resulting slurry was dried in an oven gradually heated to 110° C. (>2 hours, 10° C./min.). The impregnated catalyst mixture was then calcined at 500° C. (6 hours, 1° C./min).

Catalyst Preparation E

Preparation of 0.5 wt. % Tin on High Purity Low Surface Area Silica.

Powdered and meshed high purity low surface area silica (100 g) of uniform particle size distribution of about 0.2 mm was dried at 120° C. in an oven under nitrogen atmosphere overnight and then cooled to room temperature. To this was added a solution of tin oxalate (Alfa Aesar) (1.74 g) in dilute nitric acid (1N, 8.5 ml). The resulting slurry was dried in an oven gradually heated to 110° C. (>2 hours, 10° C./min.). The impregnated catalyst mixture was then calcined at 500° C. (6 hours, 1° C./min).

Catalyst Preparation F

Preparation of 2 wt. % Platinum and 2 wt. % Tin on High Surface Area Silica

Powdered and meshed high surface area silica NPSG SS61138 (100 g) of uniform particle size distribution of about 0.2 mm was dried at 120° C. in a circulating air oven atmosphere overnight and then cooled to room temperature. To this was added a solution of nitrate hexahydrate Chempur). The resulting slurry was dried in an oven gradually heated to 110° C. (>2 hours, 10° C./min.) then calcined. To this was added a solution of platinum nitrate (Chempur) in distilled water and a solution of tin oxalate (Alfa Aesar) in dilute nitric acid. The resulting slurry was dried in an oven gradually heated to 110° C. (>2 hours, 10° C./min.). The impregnated catalyst mixture was then calcined at 500° C. (6 hours, 1° C./min).

Catalyst Preparation G
Preparation of 1 wt % Platinum and 1 wt % Tin on High Surface Area Silica Promoted with 5% ZnO The procedure of Catalyst Prep F was substantially repeated except that: a solution of zinc nitrate hexahydrate was added to high surface area silica as described in Catalyst Preparation F. The resulting slurry was dried in an oven gradually heated to 110° C. (>2 hours, 10° C./min.) then calcined. Thereafter, a solution of platinum nitrate (Chempur) in distilled water and a solution of tin oxalate (Alfa Aesar) (1.74 g) in dilute nitric acid (1N, 8.5 ml) was thereafter added to the zinc promoted high surface area silica.

Catalyst Preparation H.
Preparation of 1 wt % Platinum and 1 wt % Zn on High Surface Area Silica Promoted with 5% $SnO_2$ The procedure of Catalyst Prep G was substantially repeated except that: a solution of tin acetate $(Sn(OAc)_2)$ was added to a high surface area silica instead of the zinc nitrate hexahydrate; and a solution of platinum nitrate, $Pt(NH_3)_4(NO_3)_2$ (Aldrich) in distilled water and a solution of tin oxalate (Alfa Aesar) in dilute nitric acid.

Catalyst Preparation I
Preparation of 1.5 wt % Platinum, 0.5 wt % Tin on Calcium Metasilicate The procedure of Catalyst Prep C above was repeated utilizing a solution of platinum nitrate (Chempur) in distilled water and a solution of tin oxalate (Alfa Aesar) in dilute nitric acid.

Catalyst Preparation J
Preparation of 1.5 wt % Platinum, 10 wt % Cobalt on High Surface Area Silica The procedure of Catalyst Prep H. above was repeated utilizing a solution of platinum nitrate (Chempur) in distilled water and, instead of the stannous octoate, a solution of cobalt (II) nitrate hexahydrate (1.74 g). The compositions of the catalysts prepared as well as summaries of the compositions of other catalyst prepared by analogous procedures and tested herein are indicated in Table 1.

Catalyst Preparations K-O
$SiO_2$—$Pt_xSn_{1-x}$ (0<x<1). Five materials were prepared varying the mol fraction of Pt while maintaining a total metal amount (Pt+Sn) of 1.20 mmol. The following preparation describes the procedure for Catalyst Preparation K, $SiO_2$—$Pt_{0.5}Sn_{0.5}$ (i.e., x=0.5; equimolar ratio of both metals). The remaining preparations (i.e., x=0, 0.25, 0.75, and 1.00; Catalyst Prep's L, M, N and O respectively) were carried out identically using the appropriate amounts of the metal precursors $Pt(NH_3)_4(NO_3)_2$ and $Sn(OAc)_2$. The catalysts were prepared by first adding $Sn(OAc)_2$ (tin acetate, $Sn(OAc)_2$ from Aldrich) (0.1421 g, 0.60 mmol) to a vial containing 6.75 ml of 1:1 diluted glacial acetic acid (Fisher). The mixture was stirred for 15 min at room temperature, and then, 0.2323 g (0.60 mmol) of solid $Pt(NH_3)_4(NO_3)_2$ (Aldrich) were added. The mixture was stirred for another 15 min at room temperature, and then added drop wise to 5.0 g of dry $SiO_2$ catalyst support (high purity silica catalyst support HSA SS #61138, SA=250 m²/g; SZ #61152, SA=156 m²/g; Saint-Gobain N or Pro), in a 100 ml round-bottomed flask. The metal solution was stirred continuously until all of the Pt/Sn mixture had been added to the $SiO_2$ catalyst support while rotating the flask after every addition of metal solution. After completing the addition of the metal solution, the flask containing the impregnated catalyst was left standing at room temperature for two hours. The flask was then attached to a rotor evaporator (bath temperature 80° C.), and evacuated til dried while slowly rotating the flask. The material was then dried further overnight at 120° C., and then calcined using the following temperature program: 25°→160° C./ramp 5.0 deg/min; hold for 2.0 hours; 160→500° C./ramp 2.0 deg/min; hold for 4 hours. Yield: 5.2 g of dark grey material.

Catalyst Preparation P
$SiO_2$—$CaSiO_3(5)$-Pt(3)-Sn(1.8). The material was prepared by first adding $CaSiO_3$ (Aldrich) to the $SiO_2$ catalyst support, followed by the addition of Pt/Sn as described previously. First, an aqueous suspension of $CaSiO_3$ (≤200 mesh) was prepared by adding 0.52 g of the solid to 13 ml of deionized $H_2O$, followed by the addition of 1.0 ml of colloidal $SiO_2$ (15 wt % solution, NALCO). The suspension was stirred for 2 h at room temperature and then added to 10.0 g of $SiO_2$ catalyst support (14/30 mesh) using incipient wetness technique. After standing for 2 hours, the material was evaporated to dryness, followed by drying at 120° C. overnight under circulating air and calcination at 500° C. for 6 hours. All of the $SiO_2$—$CaSiO_3$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described above for the $SiO_2$—$Pt_xSn_{1-x}$ materials. Yield: 11.21 g of dark grey material.

Catalyst Preparation Q
$CaSiO_3$—Pt(1)-Sn(1). To a 100 ml round-bottomed flask containing a Teflon-coated magnetic stir bar, 40 ml of 1.0 M $NHO_3$ was added, followed by the addition of 0.2025 g (0.52 mmol) of solid $Pt(NH_3)_4(NO_3)_2$. The Pt complex was dissolved with stirring and 0.2052 g (0.87 mmol) of solid $Sn(OAc)_2$ was then added. Next, 10.0 g of $CaSiO_3$ (≤200 mesh) was added with stirring; the mixture was then heated to 80° C. and stirred for two hours at this temperature. The suspension was then evacuated to dryness using a rotor evaporator (bath temperature 80° C.), the solid transferred into a porcelain dish, and dried at 120° C. overnight under circulation air. After calcination (25° C.→160° C./ramp @5.0 deg/min; hold for 2.0 hours; 160→500° C./ramp @2.0 deg/min; hold for 4 hours) the material was pressed, pelletized under pressure, our particular press applying a force of 40,000 lbs for 15 minutes, and crushed and sieved to a 14/30 mesh. Yield: 9.98 g of a tan colored material.

Catalyst Preparation R
$SiO_2$—$TiO_2(10)$-Pt(3)-Sn(1.8). The $TiO_2$-modified silica support was prepared as follows. A solution of 4.15 g (14.6 mmol) of $Ti\{OCH(CH_3)_2\}_4$ in 2-propanol (14 ml) was added dropwise to 10.0 g of $SiO_2$ catalyst support (¹⁄₁₆ inch extrudates) in a 100 ml round-bottomed flask. The flask was left standing for two hours at room temperature, and then evacuated to dryness using a rotor evaporator (bath temperature 80° C.). Next, 20 ml of deionized $H_2O$ was slowly added to the flask, and the material was left standing for 15 min. The resulting water/2-propanol was then removed by filtration, and the addition of $H_2O$ was repeated two more times. The final material was dried at 120° C. overnight under circulation air, followed by calcination at 500° C. for 6 hours. All of the $SiO_2$—$TiO_2$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described above for the $SiO_2$—$Pt_xSn_{1-x}$ materials. Yield: 11.98 g of dark grey ¹⁄₁₆ inch extrudates.

Catalyst Preparation S
$SiO_2$—$WO_3(10)$-Pt(3)-Sn(1.8). The $WO_3$-modified silica support was prepared as follows. A solution of 1.24 g (0.42 mmol) of $(NH_4)_6H_2W_{12}O_{40}\cdot nH_2O$, (AMT) in deionized $H_2O$ (14 ml) was added dropwise to 10.0 g of $SiO_2$ NPSGSS 61138 catalyst support (SA=250 m²/g, ¹⁄₁₆ inch extrudates) in a 100 ml round-bottomed flask. The flask was left standing for two hours at room temperature, and then evacuated to dryness using a rotor evaporator (bath temperature 80° C.). The resulting material was dried at 120° C. overnight under circulation air, followed by calcination at 500° C. for 6 hours. All of the (light yellow) $SiO_2$—$WO_3$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described above for the $SiO_2$—$Pt_xSn_{1-x}$ materials. Yield: 12.10 g of dark grey 1/16 inch extrudates.

Catalyst Preparation T (H-ZSM-5)-Pt(3)-Sn(1.8). The material was prepared by slurry impregnation of H-ZSM-5 (prepared from $NH_4$-ZSM-5 by calcination at 550° C. for 8 hours under air). An aqueous solution of 0.6711 g (1.73 mmol) of $Pt(NH_3)_4(NO_3)_2$ and 0.4104 g (1.73 mmol) of $Sn(OAc)_2$ was prepared by adding the components to 40 ml of 1:1 diluted acetic acid in a 100 ml round-bottomed flask and stirring the mixture for 15 min at room temperature. Next, 10.0 g of solid, finely powdered H-ZSM-5 was added to the solution with stirring, and the mixture was stirred for another two hours at room temperature. The flask was then evacuated to dryness using a rotor evaporator (bath temperature 80° C.), and the resulting material was dried at 120° C. overnight under circulation air. After calcination (250° C.→160° C./ramp 5.0 deg/min; hold for 2.0 hours; 160→500° C./ramp 2.0 deg/min; hold for 4 hours) the material was pressed, pelletized, crushed and sieved to a 14/30 mesh. Yield: 9.55 g of a grey colored material.

Catalyst Preparation U $SiO_2$—$Re_xPd_{1-x}$ (0<x<1). Five materials were prepared varying the mol fraction of Re while maintaining a total metal amount (Re+Pd) of 1.20 mmol. The following preparation describes the procedure for $SiO_2$—$Re_{0.5}Pd_{0.5}$ (i.e., x=0.5; equimolar ratio of both metals). The remaining preparations (i.e., x=0, 0.25, 0.75, and 1.00) were carried out identically using the appropriate amounts of the metal precursors $NH_4ReO_4$ and $Pd(NO_3)_2$. The metal solutions were prepared by first adding $NH_4ReO_4$ (0.1609 g, 0.60 mmol) to a vial containing 6.75 ml of deionized $H_2O$. The mixture was stirred for 15 min at room temperature, and 0.1154 g (0.60 mmol) of solid $Pd(NO_3)_2$ was then added. The mixture was stirred for another 15 min at room temperature, and then added drop wise to 5.0 g of dry $SiO_2$ catalyst support (14/30 mesh) in a 100 ml round-bottomed flask. After completing the addition of the metal solution, the flask containing the impregnated catalyst was left standing at room temperature for two hours. The flask was then attached to a rotor evaporator (bath temperature 80° C.), and evacuated to dryness. All other manipulations (drying, calcination) were carried out as described above for the $SiO_2$—$Pt_xSn_{1-x}$ materials, vide supra. Yield: 5.1 g of a brown material.

Catalyst Preparation V $SiO_2$—$CaSiO_3(5)$-Re(4.5)-Pd(1). The $SiO_2$—$CaSiO_3(5)$ modified catalyst support was prepared as described for $SiO_2$—$CaSiO_3(5)$-Pt(3)-Sn(1.8), vide supra. The Re/Pd catalyst was prepared then by impregnating the $SiO_2$—$CaSiO_3(5)$ (1/16 inch extrudates) with an aqueous solution containing $NH_4ReO_4$ and $Pd(NO_3)_2$. The metal solutions were prepared by first adding $NH_4ReO_4$ (0.7237 g, 2.70 mmol) to a vial containing 12.0 ml of deionized $H_2O$. The mixture was stirred for 15 min at room temperature, and 0.1756 g (0.76 mmol) of solid $Pd(NO_3)_2$ was then added. The mixture was stirred for another 15 min at room temperature, and then added drop wise to 10.0 g of dry $SiO_2$-(0.05)$CaSiO_3$ catalyst support in a 100 ml round-bottomed flask. After completing the addition of the metal solution, the flask containing the impregnated catalyst was left standing at room temperature for two hours. All other manipulations (drying, calcination) were carried out as described above for the $SiO_2$—$Re_xPd_{1-x}$ materials, vide supra. Yield: 10.9 g of brown material.

Catalyst Preparation W $CaSiO_3$—Re(5)-Pd(2.5). The material was prepared by slurry impregnation of $CaSiO_3$ (powder, ≤200 mesh). An aqueous solution of 0.6169 g (2.30 mmol) of $NH_4ReO_4$ and 0.5847 g (2.53 mmol) of $Pd(NO_3)_2$ was prepared by adding the components to 40 ml of deionized $H_2O$ in a 100 ml round-bottomed flask and stirring the mixture for 15 min at room temperature. Next, 10.0 g of solid, finely powdered $CaSiO_3$ was added to the solution with stirring, and the mixture was stirred for another two hours at room temperature. The flask was then evacuated to dryness using a rotor evaporator (bath temperature 80° C.), and the resulting material was dried at 120° C. overnight under circulation air. All other manipulations (drying, calcination) were carried out as described above for the $SiO_2$—$Re_xPd_{1-x}$ materials, vide supra. The final material was pressed, pelletized using a press that applies a force of 40,000 lbs for 15 minutes, crushed and sieved to a 14/30 mesh. Yield: 10.65 g of a brown colored material.

Catalyst Preparation X $SiO_2$—Co(10)-Pt(1). The material was prepared by impregnating HSA $SiO_2$ (14/30 mesh) with an aqueous solution containing $Co(NO_3)_2.6H_2O$ and $Pt(NH_3)_4(NO_3)_2$. The metal solutions were prepared by first adding $Co(NO_3)_2.6H_2O$ (5.56 g, 19.1 mmol) to a vial containing 12.0 ml of deionized $H_2O$. The mixture was stirred for 15 min at room temperature, and 0.2255 g (0.58 mmol) of solid $Pt(NH_3)_4(NO_3)_2$ was then added. The mixture was stirred for another 15 min at room temperature, and then added drop wise to 10.0 g of dry $SiO_2$ catalyst support (14/30 mesh) in a 100 ml round-bottomed flask. After completing the addition of the metal solution, the flask containing the impregnated catalyst was left standing at room temperature for two hours. All other manipulations (drying, calcination) were carried out as described above for the $SiO_2$—$Pt_xSn_{1-x}$ materials, vide supra. Yield: 11.35 g of a black material.

Catalyst Preparation Y $CaSiO_3$—Co(10)-Pt(1). The material was prepared by slurry impregnation of $CaSiO_3$ (powder, 200 mesh). An aqueous solution of 5.56 g (19.1 mmol) of $Co(NO_3)_2.6H_2O$ and 0.2255 g (0.58 mmol) of $Pt(NH_3)_4(NO_3)_2$ was prepared by adding the components to 40 ml of deionized $H_2O$ in a 100 ml round-bottomed flask and stirring the mixture for 15 min at room temperature. Next, 10.0 g of solid, finely powdered $CaSiO_3$ was added to the solution with stirring. The mixture was then heated to 65° C., and stirred for another two hours at this temperature. The flask was then evacuated to dryness using a rotor evaporator (bath temperature 80° C.), and the resulting material was dried at 120° C. overnight under circulation air. All other manipulations (drying, calcination) were carried out as described above for the $SiO_2$—Co(10)-Pt(1) material, vide supra. The final material was pressed, pelletized under pressure, crushed and sieved to a 14/30 mesh. Yield: 10.65 g of a black material.

Catalyst Preparation Z $ZrO_2$—Co(10)-Pt(1). The material was prepared by impregnating $ZrO_2$ (SZ 61152, Saint-Gobain N or Pro, 14/30 mesh) with an aqueous solution containing $Co(NO_3)_2.6H_2O$ and $Pt(NH_3)_4(NO_3)_2$. The metal solutions were prepared by first adding $Co(NO_3)_2.6H_2O$ (5.56 g, 19.1 mmol) to a vial containing 5.0 ml of deionized $H_2O$. The mixture was stirred for 15 min at room temperature, and 0.2255 g (0.58 mmol) of solid $Pt(NH_3)_4(NO_3)_2$ was then added. The mixture was stirred for another 15 min at room temperature, and then added drop wise to 10.0 g of the dry $ZrO_2$ catalyst support (14/30 mesh) in a 100 ml round-bottomed flask. After completing the addition of the metal solution, the flask containing the impregnated catalyst was left standing at room temperature for two hours. All other manipulations (drying, calcination) were carried out as described above for the $SiO_2$—Co(10)-Pt(1) material, vide supra. Yield: 11.35 g of a black material.

Catalyst Preparation AA $SiO_2$—$CaSiO_3$(2.5)-Pt(1.5)-Sn(0.9).

The material was prepared as described above for $SiO_2$—$CaSiO_3$(5)-Pt(3)-Sn(1.8) using 0.26 g of $CaSiO_3$, 0.5 ml of colloidal $SiO_2$ (15 wt % solution, NALCO), 0.3355 g (0.86 mmol) of $Pt(NH_3)_4(NO_3)_2$ and 0.2052 g (0.86 mmol) of $Sn(OAc)_2$. Yield: 10.90 g of dark grey material.

Catalyst Preparation BB $TiO_2$—$CaSiO_3$(5)-Pt(3)-Sn(1.8).

The material was prepared by first adding $CaSiO_3$ to the $TiO_2$ catalyst (Anatase, 14/30 mesh) support, followed by the addition of Pt/Sn as described previously. First, an aqueous suspension of $CaSiO_3$ (≤200 mesh) was prepared by adding 0.52 g of the solid to 7.0 ml of deionized $H_2O$, followed by the addition of 1.0 ml of colloidal $SiO_2$ (15 wt % solution, NALCO). The suspension was stirred for 2 h at room temperature and then added to 10.0 g of $TiO_2$ catalyst support (14/30 mesh) using incipient wetness technique. After standing for 2 hours, the material was evaporated to dryness, followed by drying at 120° C. overnight under circulating air and calcination at 500° C. for 6 hours. All of the $TiO_2$—$CaSiO_3$ material was then used for Pt/Sn metal impregnation using 0.6711 g (1.73 mmol) of $Pt(NH_3)_4(NO_3)_2$ and 0.4104 g (1.73 mmol) of $Sn(OAc)_2$ following the procedure described above for the $SiO_2$—$Pt_xSn_{1-x}$ materials. Yield: 11.5 g of light grey material.

Catalyst Preparation CC

KA160-Pt(3)-Sn(1.8).

The material was prepared by incipient wetness impregnation of KA160 catalyst support ($SiO_2$-(0.05)$Al_2O_3$, Sud Chemie, 14/30 mesh) as described previously for $SiO_2$—$Pt_xSn_{1-x}$, vide infra. The metal solutions were prepared by first adding $Sn(Oac)_2$ (0.2040 g, 0.86 mmol) to a vial containing 4.75 ml of 1:1 diluted glacial acetic acid. The mixture was stirred for 15 min at room temperature, and then, 0.3350 g (0.86 mmol) of solid $Pt(NH_3)_4(NO_3)_2$ were added. The mixture was stirred for another 15 min at room temperature, and then added drop wise to 5.0 g of dry KA160 catalyst support (14/30 mesh) in a 100 ml round-bottomed flask. All other manipulations, drying and calcination was carried out as described above for $SiO_2$—$Pt_xSn_{1-x}$. Yield: 5.23 g of tan-colored material.

Catalyst Preparation DD

KA160-$CaSiO_3$(8)-Pt(3)-Sn(1.8).

The material was prepared by first adding $CaSiO_3$ to the KA160 catalyst support, followed by the addition of Pt/Sn as described above for KA160-Pt(3)-Sn(1.8). First, an aqueous suspension of $CaSiO_3$ (≤200 mesh) was prepared by adding 0.42 g of the solid to 3.85 ml of deionized $H_2O$, followed by the addition of 0.8 ml of colloidal $SiO_2$ (15 wt % solution, NALCO). The suspension was stirred for 2 h at room temperature and then added to 5.0 g of KA160 catalyst support (14/30 mesh) using incipient wetness technique. After standing for 2 hours, the material was evaporated to dryness, followed by drying at 120° C. overnight under circulating air and calcinations at 500° C. for 6 hours. All of the KA160-$CaSiO_3$ material was then used for Pt/Sn metal impregnation using 0.3350 g (0.86 mmol) of $Pt(NH_3)_4(NO_3)_2$ and 0.2040 g (0.86 mmol) of $Sn(Oac)_2$ following the procedure described above for the $SiO_2$—$Pt_xSn_{1-x}$ materials. Yield: 5.19 g of tan-colored material.

TABLE 1

Catalyst Summary

| CP | PGM | Promoter | other | Support | Ex |
|---|---|---|---|---|---|
| A | 0.5 wt % Pt | 5 wt % Sn | — | HP LSA $SiO_2$ | 1 |
| B | 1 wt % Pt | 1 wt % Sn | — | HP LSA $SiO_2$ | 2 |
| C | 1 wt % Pt | 1 wt % Sn | — | $CaSiO_2$ | 4 |
| D | 0.5 wt % Pt | 0.5 wt % Sn | 0.2 wt % Co | HP LSA $SiO_2$ | — |
| E | — | 0.5 wt % Sn | — | HP LSA $SiO_2$ | CE1 |
| F | 2 wt % Pt | 2 wt % Sn | — | HSA $SiO_2$ | |
| G | 1 wt % Pt | 1 wt % Sn | 5 wt % ZnO | HSA $SiO_2$ | 4 |
| H | 1 wt % Pt | 1 wt % Zn | 5 $SnO_2$ | HSA $SiO_2$ | 4 |
| I | 1.5 wt % Pt | 0.5 wt % Sn | — | Ca $SiO_2$ | 4 |
| J | 1 wt % Pt | — | 10 wt % Co | HSA $SiO_2$ | 4 |
| K | $SiO_2$—$Pt_xSn_{(1-x)}$ (Σ [Pt] + [Sn] = 1.20 mmol X = 0.5 | | — | HSA $SiO_2$ | |
| L | $SiO_2$—$Pt_xSn_{(1-x)}$ (Σ [Pt] + [Sn] = 1.20 mmol X = 0 | | — | HSA $SiO_2$ | |
| M | $SiO_2$—$Pt_xSn_{(1-x)}$ (Σ [Pt] + [Sn] = 1.20 mmol X = 0.75 | | — | HSA $SiO_2$ | |
| N | $SiO_2$—$Pt_xSn_{(1-x)}$ (Σ [Pt] + [Sn] = 1.20 mmol X = 0.25 | | — | HSA $SiO_2$ | |
| O | $SiO_2$—$Pt_xSn_{(1-x)}$ (Σ [Pt] + [Sn] = 1.20 mmol X = 1 | | — | HSA $SiO_2$ | |
| P | 3 wt % Pt | 1.8 wt % Sn | 5 wt % $CaSiO_3$ | HSA $SiO_2$ | |
| Q | 1 wt % Pt | 1 wt % Sn | — | $CaSiO_3$ | |
| R | 3 wt % Pt | 1.8 wt % Sn | 10 wt % $TiO_2$ | HSA $SiO_2$? | |
| S | 3 wt % Pt | 1.8 wt % Sn | $WO_3$ | HSA $SiO_2$ | |
| T | 3 wt % Pt | 1.8 wt % Pt | | H-ZSM-5 | |
| U | $SiO_2$—$Re_xPd_{(1-x)}$ (Σ [Re] + [Pd] = 1.20 mmol X = 0.5 | | — | HSA $SiO_2$ | |
| V | $SiO_2$—$Re_xPd_{(1-x)}$ (Σ [Re] + [Pd] = 1.20 mmol X = 0 | | — | HSA $SiO_2$ | |
| W | $SiO_2$—$Re_xPd_{(1-x)}$ (Σ [Re] + [Pd] = 1.20 mmol X = 0.25 | | — | HSA $SiO_2$ | |
| X | $SiO_2$—$Re_xPd_{(1-x)}$ (Σ [Re] + [Pd] = 1.20 mmol X = 0.75 | | — | HSA $SiO_2$ | |

TABLE 1-continued

Catalyst Summary

| CP | PGM | Promoter | other | Support | Ex |
|---|---|---|---|---|---|
| Y | $SiO_2$—$Re_xPd_{(1-x)}$ ($\Sigma$ [Re] + [Pd] = 1.20 mmol X = 1) | | | HSA $SiO_2$ | |
| Z | 1 mol % Pd | 4.5 mol % Re | 5 wt % $CaSiO_3$ | HSA $SiO_2$? | |
| AA | 1.5% Pt | 0.9% Sn | 2.5% $CaSiO_3$ | $SiO_2$ | |
| BB | 3% Pt | 1.8% Sn | 5% $CaSiO_3$ | $TiO_2$ | |
| CC | 3%-Pt | 1.8% Sn | | KA160 | |
| DD | 3% Pt | 1.8% Sn | 8% $CaSiO_3$ | KA-160 | |
| AAA | 2.5 wt % Pd | 5 wt % Re | | $CaSiO_3$ | |
| BBB | 1 wt % Pt | 10 wt % Co | | HSA $SiO_2$ | |
| CCC | 1 wt % Pt | 10 wt % Co | | $CaSiO_3$ | |
| DDD | 1 wt % Pt | 10 wt % Co | | $ZrO_2$ | |

Gas Chromatographic (GC) Analysis of the Products

The analysis of the products was carried out by online GC. A three channel compact GC equipped with one flame ionization detector (FID) and 2 thermal conducting detectors (TCDs) was used to analyze the reactants and products.

The front channel was equipped with an FID and a CP-Sil 5 (20 m)+WaxFFap (5 m) column and was used to quantify: Acetaldehyde; Ethanol; Acetone; Methyl acetate; Vinyl acetate; Ethyl acetate; Acetic acid; Ethylene glycol diacetate; Ethylene glycol; Ethylidene diacetate; and Paraldehyde.

The middle channel was equipped with a TCD and Porabond Q column and was used to quantify: $CO_2$; ethylene; and ethane.

The back channel was equipped with a TCD and Molsieve 5A column and was used to quantify: Helium; Hydrogen; Nitrogen; Methane; and Carbon monoxide.

Prior to reactions, the retention time of the different components was determined by spiking with individual compounds and the GCs were calibrated either with a calibration gas of known composition or with liquid solutions of known compositions. This allowed the determination of the response factors for the various components.

EXAMPLE 1

In a tubular reactor made of stainless steel, having an internal diameter of 30 mm and capable of being raised to a controlled temperature, there are arranged 50 ml of catalyst prepared as described in catalyst preparation C above. The length of the combined catalyst bed after charging was approximately about 70 mm.

The feed liquid was comprised essentially of acetic acid. The reaction feed liquid was evaporated and charged to the reactor along with hydrogen and helium as a carrier gas with an average combined gas hourly space velocity (GHSV) of 2500 $hr^{-1}$ at a temperature of 250° C. and pressure of 100 psig. The feed stream contained a mole percent of acetic acid from about 6.1% to about 7.3% and mole percent of hydrogen from about 54.3% to about 61.5%. A portion of the vapor effluent from the reactor was passed through a gas chromatograph for analysis of the contents of the effluents. The selectivity to ethanol was 93.4% at a conversion of acetic acid 85%.

The catalyst utilized was 1 weight percent platinum and 1 weight percent tin on silica prepared in accordance with the procedure of Catalyst Preparation A.

EXAMPLE 2

The catalyst utilized was 1 weight percent platinum and 1 weight percent tin on calcium silicate prepared in accordance with the procedure of Example C.

The procedure as set forth in Example 1 is substantially repeated with an average combined gas hourly space velocity (GHSV) of 2,500 $hr^{-1}$ of the feed stream of the vaporized acetic acid and hydrogen at a temperature of 250° C. and pressure of 22 bar. A portion of the vapor effluent is passed through a gas chromatograph for analysis of the contents of the effluents. The acetic acid conversion is greater than 70% and ethanol selectivity is 99%.

COMPARATIVE EXAMPLE 1

The catalyst utilized was 1 weight percent tin on low surface area high purity silica prepared in accordance with the procedure of Example E.

The procedure as set forth in Example 1 is substantially repeated with an average combined gas hourly space velocity (GHSV) of 2,500 $hr^{-1}$ of the feed stream of the vaporized acetic acid and hydrogen at a temperature of 250° C. and pressure of 22 bar. A portion of the vapor effluent is passed through a gas chromatograph for analysis of the contents of the effluents. The acetic acid conversion is less than 10% and ethanol selectivity is less than 1%.

EXAMPLE 3

The procedure of Example 2 was repeated using a variety of catalysts at a temperature as set forth in Table 2 setting forth the percentages of carbon monoxide (CO), acetaldehyde (AcH) and ethane in the products as well as the selectivity for, and productivity of, ethyl acetate (EtOAc); ethanol (EtOH) as well as the percentage conversion of acetic acid (HOAc) (MCD p. 4). Throughout, the mole ratio of $H_2$ to acetic acid was maintained at 5:1. For convenience, the results of examples 1 and 2 and comparative example 1 are also included in Table 2. Generally speaking when it is desired to produce ethanol as the primary product, selectivities to ethanol above 80% or so are desirable; selectivities to ethyl acetate of less than 5% are desired, preferably less than 3%.

TABLE 2

| CP# | Catalyst | Reactor Temp (° C.) | CO | AcH % | Ethane % | EtOAc % | EtOH % | EtOAc g/kg/h | Et OH g/kg/h | HOAc Conv. % |
|---|---|---|---|---|---|---|---|---|---|---|
| K | $SiO_2$—$Pt_xSn_{1-x}$; x = 0 | 250 | — | — | — | — | — | — | — | — |
| L | $SiO_2$—$Pt_xSn_{1-x}$; x = 0.25 | 250 | — | — | — | 41 | 59 | 473 | 683 | 28 |
| M | $SiO_2$—$Pt_xSn_{1-x}$; x = 0.50 | 250 | — | — | — | 26 | 74 | 788 | 2217 | 73 |
| N | $SiO_2$—$Pt_xSn_{1-x}$; x = 0.75 | 250 | — | — | — | 72 | 28 | 482 | 186 | 17 |
| O | $SiO_2$—$Pt_xSn_{1-x}$; x = 1.00 | 250 | — | — | — | 100 | — | 125 | — | 3 |
| U | $SiO_2$—$Re_xPd_{1-x}$; x = 0 | | — | — | — | 62 | 38 | 126 | 77 | 5 |
| V | $SiO_2$—$Re_xPd_{1-x}$; x = 0.25 | | — | — | — | 80 | 20 | 305 | 75 | 9 |
| W | $SiO_2$—$Re_xPd_{1-x}$; x = 0.50 | | — | — | — | 77 | 23 | 344 | 102 | 11 |
| X | $SiO_2$—$Re_xPd_{1-x}$; x = 0.75 | | — | — | — | 44 | 56 | 170 | 218 | 9 |
| Y | $SiO_2$—$Re_xPd_{1-x}$; x = 1.00 | | — | — | — | 100 | — | 52 | 0 | 1 |
| S | $SiO_2$—$TiO_2$(10)—Pt(3)—Sn(1.8) | | — | — | — | 53 | 47 | 1648 | 1454 | 73 |
| T | (H-ZSM-5)—Pt(3)—Sn(1.8)[7] | | — | — | — | 4 | — | 107 | — | 78[7] |
| U | $SiO_2$—$Re_xPd_{1-x}$; x = 0 | | — | — | — | 62 | 38 | 126 | 77 | 5 |
| V | $SiO_2$—$Re_xPd_{1-x}$; x = 0.25 | | — | — | — | 80 | 20 | 305 | 75 | 9 |
| W | $SiO_2$—$Re_xPd_{1-x}$; x = 0.50 | | — | — | — | 77 | 23 | 344 | 102 | 11 |
| X | $SiO_2$—$Re_xPd_{1-x}$; x = 0.75 | | — | — | — | 44 | 56 | 170 | 218 | 9 |
| Y | $SiO_2$—$Re_xPd_{1-x}$; x = 1.00 | | — | — | — | 100 | — | 52 | 0 | 1 |
| CC | KA160-Pt(3)—Sn(1.8). | 250 | 3 | — | — | 50 | 47 | 1036 | 946 | 61 |
| DD | KA160-$CaSiO_3$(8)—Pt(3)—Sn(1.8). | 250 | 3 | — | — | 13 | 84 | 213 | 1151 | 43 |
| P | $SiO_2$—$CaSiO_3$(5)—Pt(3)—Sn(1.8) | 250 | — | 2 | — | 6 | 92 | 62 | 926 | 24 |

[1]The preparation of the individual catalysts is described in detail herein. The numbers in parentheses represent the amount of the actual component (metal, metal oxide) in wt %.
[2]Product selectivity (wt %) was calculated by from authentic sample calibrated GC analyses.
[3]The acetic acid conversion (%) was calculated by: [HOAc] Conversion, % = {[HOAc] (Feed, mmol/min) – [HOAc] (Effluent, mmol/min)/[HOAc] (Feed, mmol/min)} * 100.
[4]The STY (in g/kg/h) was calculated as: [Product] (g)/[catalyst] (kg)/hour.
[5]In addition, some $CH_4$ and CO (5 wt % each) were also observed.
[6]The data in the first row was obtained after 2 hrs of reaction time. The second row summarizes data obtained after 8 hrs. In addition, some $CH_4$ and CO were also observed: 2 h; $CH_4$, 4 wt %; CO, 4 wt %; 8 h; $CH_4$, 10 wt %, CO, 9 wt %.
[7]The main product obtained with this catalyst is diethyl ether, EtOEt, with a selectivity of 96%, and a productivity of 2646 g/kg/h.

EXAMPLE 4

Vaporized acetic acid and hydrogen were passed over a hydrogenation catalyst of the present invention comprising 2 wt % Pt; and 2 wt % Sn on high surface area silica (NPSG SS61138) having a surface area of approximately 250 m²/g at a ratio of hydrogen to acetic acid of about 160 sccm/min $H_2$: 0.09 g/min HOAc, the hydrogen being diluted with about 60 sccm/min $N_2$ at a space velocity of about 6570 hr$^{-1}$ and a pressure of 200 psig. The temperature was increased at about 50 hrs, 70 hrs and 90 hrs as indicated in FIGS. 1 and 2 wherein the productivity in grams of the indicated products (ethanol, acetaldehyde, and ethyl acetate) per kilogram of catalyst per hour are indicated in FIG. 1 and the selectivity of a catalyst for the various products are indicated in FIG. 2 with the upper line indicating productivity of or selectivity to ethyl acetate, the intermediate line indicating ethanol and the lower line indicating acetaldehyde. It is considered especially significant that production of, and selectivity for, acetaldehyde were low. The results are summarized in the Data Summary below.

Data Summary

|  | 225° C. | 250° C. | 280° C. | 296° C. |
|---|---|---|---|---|
| HOAc Conversion (%): | 11.15 | 26.49 | 36.65 | 33.77 |
| EtOH Productivity (g/kg/h): | 187.65 | 380.59 | 517.62 | 434.67 |
| EtOH Selectivity (wt %): | 41.96 | 35.83 | 35.67 | 33.07 |
| EtOAc Productivity (g/kg/h): | 244.04 | 638.20 | 882.55 | 835.50 |
| EtOAc Selectivity (wt %): | 57.08 | 62.79 | 62.36 | 63.56 |

EXAMPLE 5

The procedure as set forth in Example 1 was substantially repeated using a catalyst having 2 wt. % Pt; 2 wt. % Sn supported on a catalyst comprising pellets of high surface area silica SS61138 from Saint-Gobain N or Pro with an average combined gas hourly space velocity (GHSV) of 2500 hr$^{-1}$ of the feed stream of vaporized acetic acid, hydrogen and helium at the indicated temperature set forth in table 2 and pressure of 100 psig. The resulting feed stream contained a mole percent of acetic acid of about 7.3% and mole percent of hydrogen of about 54.3%. A portion of the vapor effluent was passed through a gas chromatograph for analysis of the contents of the effluents. Results are as presented in Table 1.

TABLE 3

Catalyst Stability
2 wt % Pt/2 wt % Sn Catalyst "F"? supported on HSA $SiO_2$
Reaction Temperature 225° C.-296° C.; total TOS = 115 h.

|  | 225° C. | 250° C. | 280° C. | 296° C. |
|---|---|---|---|---|
| HOAc conversion % | 11.15 | 26.49 | 36.65 | 33.77 |
| EtOH productivity g/kg/h. | 187.65 | 380.59 | 517.62 | 434.67 |
| EtOH selectivity wt. % | 41.96 | 35.83 | 35.67 | 33.07 |
| EtOAc productivity g/kg/h | 244.04 | 638.20 | 8082.55 | 835.50 |

TABLE 3-continued

Catalyst Stability
2 wt % Pt/2 wt % Sn Catalyst "F"? supported on HSA SiO$_2$
Reaction Temperature 225° C.-296° C.; total TOS = 115 h.

|  | 225° C. | 250° C. | 280° C. | 296° C. |
|---|---|---|---|---|
| EtOAc selectivity wt. % | 57.08 | 62.79 | 62.36 | 63.56 |

The results of Example 5 are summarized in FIG. 3, which demonstrates that the relatively insensitivity of the catalyst to changes in temperature makes this catalyst well-suited for use in a so-called adiabatic reactor in which the temperature may vary substantially over the catalyst bed due to the low and uneven rate of heat removal from the reactor.

EXAMPLE 6

The influence of the [Sn]/[Pt] molar ratio in SiO$_2$—Pt$_x$Sn$_{(1-x)}$ catalysts was studied by (i) varying the mol fraction of Pt at a constant metal loading ([Pt]+[Sn]=1.20 mmol), and (ii) as a function of the reduction temperature. A distinct maximum at a Pt mol fraction of 0.5 (i.e., [Sn]/[Pt]=1.0) was observed for both the acetic acid conversion, and the selectivity towards ethanol. The selectivity towards ethyl acetate sharply changes at [Sn]/[Pt]=1.0) in favor of ethanol. At a Pt mol fraction of either 25% or 75%, ethyl acetate is observed as the main product. The presence of an equimolar ratio of Pt and Sn appears to be preferable both for the increase in acetic acid conversion and the selectivity towards ethanol, c.f. FIGS. 4A-C.

Vaporized acetic acid (0.09 g/min HOAc) and hydrogen (160 sccm/min H$_2$; 60 sccm/min N$_2$) were passed over a hydrogenation catalyst of the present invention comprising Pt and Sn on high surface area silica having a surface area of approximately 250 m$^2$/g at a Temperature of =250° C.; GHSV=6570 h$^{-1}$; 12 h of reaction time. In this example 6, the amount of metal (Pt+Sn) was maintained constant and the mass fraction of platinum was varied between 0 and 1. FIGS. 4A-4C illustrate the selectivity, activity and productivity of the catalysts at each. From this example, it can be appreciated, that a maximum occurs in selectivity, activity and productivity when the mass fraction of platinum is approximately 0.5, i.e., the amount of platinum by weight is substantially equal to the amount of tin in the catalyst.

EXAMPLE 7

Figure 5B:
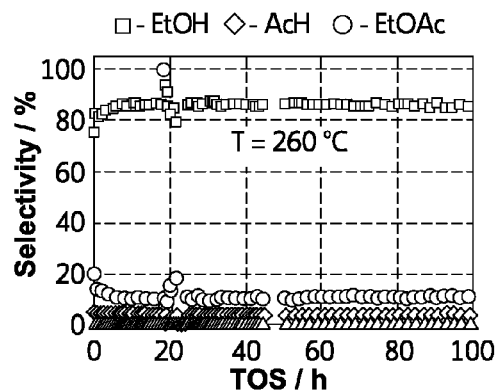

Vaporized acetic acid and hydrogen were passed over a hydrogenation catalyst of the present invention comprising 3 wt % Pt, 1.5 wt % Sn and 5 wt % CaSiO$_3$, as a promoter on high purity, high surface area silica having a surface area of approximately 250 m$^2$/g at a molar ratio of hydrogen to acetic acid of about 5:1 at a temperature of about 225° C. FIGS. 5A and 5B illustrate the selectivity, and productivity of the catalysts as a function of time on-stream during the initial portion of the catalysts life. From the results of this example as reported in FIGS. 6A and 6B, it can be appreciated, that it is possible to attain a selectivity activity of over 90% and productivity of over 500 g of ethanol per kilogram of catalyst per hour.

EXAMPLE 8

Figure 7B:
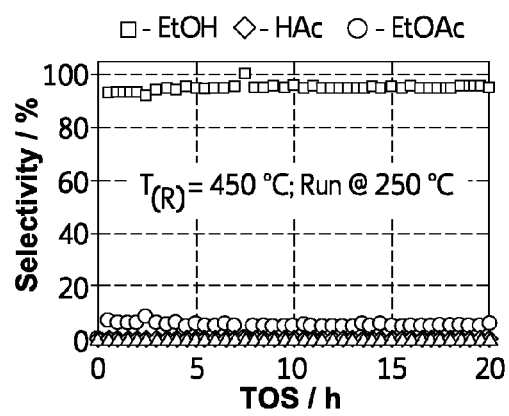

The procedure of Example 8 was repeated (same catalyst?) at a temperature of about 250° C. FIGS. 7A-7B illustrate the selectivity and productivity of the catalysts as a function of time on-stream during the initial portion of the catalysts life. From the results of this example, as reported in FIGS. 7A and 7B, it can be appreciated, that it is still possible to attain a selectivity activity of over 90% but with productivity of over 800 g of ethanol per kilogram of catalyst per hour at this temperature.

EXAMPLE 9

To investigate the sensitivity of the temperature used for reduction of the bimetallic platinum and tin precursors to the catalytic species, the influence of the reduction temperature was studied by activating the Pt/Sn optimized, SiO$_2$—(Pt$_{0.5}$Sn$_{0.5}$) catalyst, vide infra, in independent experiments from 225 to 500° C. In four experiments, the material was activated at 280, 350, 425, and 500° C. under flowing hydrogen for 4 hrs, followed by acetic acid reduction at a reaction temperature of 250° C. (Catalyst activation was carried out using a 10 mol % H$_2$/N$_2$ mixture (275 sccm/min) at ambient pressure using the following temperature program: RT→Reduction Temp. (225-500° C.), ramp 2 deg/min; hold for 4.0 hrs, then lowered (or raised as necessary) to 250° C. for HOAc reduction). In addition, the material activated at 225° C., was studied at a reaction temperature of both 225 and 250° C. in the HOAc hydrogenation. No significant change of the selectivity towards ethanol and ethyl acetate was observed across the whole temperature range, including for the catalyst activated at 225° C. for both reaction temperatures, 225 and 250° C. Interestingly, a significant increase in the conversion (and productivities) was observed for the catalysts activated at lower, 225 and 280° C. reduction temperatures. A decrease in conversion at higher reduction temperatures may be attributed to a sintering of metal particles. (See FIGS. 7A and 7B) Since no change in selectivity was observed, the composition of the metal particles (i.e., PtSn alloy) appears to remain unchanged. The results of this Example are illustrated in FIGS. 3 A-3C.

In these examples various other products including acetaldehyde, ethanol, ethyl acetate, ethane, carbon monoxide, carbon dioxide, methane, isopropanol, acetone and water were detected.

EXAMPLE 10

The catalytic performance of a variety of catalysts was evaluated in the catalytic hydrogenation of acetic acid using 2.5 ml solid catalyst of the catalysts indicated in Table 4. In each case the catalyst particles had a size of 14/30 mesh, and were diluted 1:1 v/v with 14/30 mesh quartz chips. In each run the operating pressure was 200 psig (14 bar) with a feed rate of 0.09 g/min acetic acid; 120 sccm/min of hydrogen; 60 sccm/min nitrogen at a gross hourly space velocity of 6570 h$^{-1}$ over s span of 24 hr of time on stream (TOS). The results are as indicated in Table 4.

TABLE 4

The catalytic activity of various supported-metal catalysts in the catalytic hydrogenation of HOAc. Reaction Conditions: 2.5 ml solid catalyst (14/30 mesh, diluted 1:1 (v/v, with quartz chips, 14/30 mesh); p = 200 psig (14 bar); 0.09 g/min HOAc; 120 sccm/min H$_2$; 60 sccm/min N$_2$; GHSV = 6570 h$^{-1}$; 24 h of time on stream (TOS).

| Entry No. | Catalyst[1] | Temp. (°C.) | Product Selectivities (%)[3] | | | | | Productivities (g/kg/h) | | HOAc[4] Conv. (%) |
|---|---|---|---|---|---|---|---|---|---|---|
| | | | CO | AcH | Ethane | EtOAc | EtOH | EtOAc | EtOH | |
| + | CuO—MnO$_2$(10)—Al$_2$O$_3$(34) | 275 | | | | 31 | 71 | 71 | 165 | 58 |
| 2 | (SA_250-SiO$_2$)—Pt(2.0)—Sn(2.0) | 275 | — | 5 | — | 57 | 38 | 286 | 194 | 81 |
| 3 | (SA_160-SiO$_2$)—Re(5.0)—Pd(2.5) | 248 | 31 | 4 | 8 | 6 | 51 | 14 | 126 | 20 |
| 4 | (SA_250-SiO$_2$)—Re(5.0)—Pd(2.5) | 225 | — | 11 | — | 43 | 46 | 52 | 55 | 10 |
| 5 | (SA_160-SiO$_2$)—Co(10.0)—Pt(1.0) | 275 | — | — | — | 17 | 82 | 31 | 154 | 13 |
| 6 | (SA_250-SiO$_2$)—Co(10.0)—Pt(1.0) | 275 | 4 | 5 | 2 | 6 | 79 | 41 | 534 | 50 |
| 7 | (SA_250-SiO$_2$)—ZnO—Pt(1.0)—Sn(1.0) | 275 | — | 3 | — | 21 | 76 | 84 | 116 | 22 |
| 8 | (SA_250-SiO$_2$—SnO$_2$)—Pt(1.0)—Zn(1.0) | 275 | — | 7 | — | 44 | 48 | 93 | 100 | 13 |
| 9 | CaSiO$_3$—Pt(1.0)—Sn(1.0) | 275 | — | 4 | — | 17 | 79 | 56 | 261 | 22 |
| 10 | (SA_250-SiO$_2$—MgSiO$_3$(5)—Pt(1.0)—(Sn1.0) | 250 | — | 2 | — | 10 | 88 | 35 | 192 | 22 |
| 11 | CaSiO$_3$—Pt(1.5)—Sn(0.5) | 275 | — | 1 | — | 11 | 87 | 12 | 94 | 8 |
| 12 | CaSiO$_3$—Co(10.0)—Pt(1.0) | 275 | — | 5 | — | 7 | 87 | 18 | 224 | 24 |
| 13 | CaSiO$_3$—Co(10.0)—Pt(1.0)—Sn(1.0) | 275 | 4 | 2 | 2 | 60 | 30 | 188 | 93 | 26 |
| 14 | CaSiO$_3$—Re(5.0)—Pd(2.5) | 225 | 5 | 2 | 3 | 5 | 79 | 16 | 259 | 29 |
| 15 | CaSiO$_3$—Pt(1.0)—Zn(1.0) | 275 | — | 3 | — | 56 | 41 | 58 | 11 | 7 |
| 16 | C-Pt(2.0)—Sn(1.0) | 275 | — | — | — | 43 | 57 | 66 | 88 | 12 |
| 17 | CuO(12)—ZnO(62)—Al$_2$O$_3$(25) | 225 | — | — | — | — | 100 | 6 | — | 1 |

[1]The numbers in parentheses refer to the actual catalyst components in wt %. All materials were reduced in situ under hydrogen prior to catalytic testing unless stated otherwise.
[2]T-4489 was obtained from Sud Chemie and used as received. Reaction Conditions: 5.0 mL solid catalyst (14/30 mesh, diluted 1:1 (v/v, with quartz chips, 14/30 mesh); p = 200 psig (14 bar); 0.038 g/min HOAc; 120 sccm/min H$_2$; 80 sccm/min N$_2$; GHSV = 2676 h$^{-1}$; 24 h of time on stream (TOS)
[3]Product analyses were obtained by authentic-sample calibrated GC analysis.
[4]HOAc conversion is defined as {([HOAc]$_{t=0}$ − [HOAc]$_t$)/[HOAc]$_0$} × 100%.

EXAMPLE 11

Catalyst Stability: SiO$_2$—CaSiO$_3$(5)-Pt(3)-Sn(1.8).

The catalytic performance and initial stability of SiO$_2$—CaSiO$_3$(5)-Pt(3)-Sn(1.8) was evaluated at constant temperature (260° C.) over 100 hrs of reaction time. Only small changes in catalyst performance and selectivity were observed over the 100 hrs of total reaction time. Acetaldehyde appears to be the only side product, its concentration (~3 wt %) remained largely unchanged over the course of the experiment. A summary of catalyst productivity and selectivity is provided in FIGS. 5A & 5B. The influence of the reaction temperature on product selectivity was studied in a separate experiment over a total reaction time of 125 hours, vide supra.

EXAMPLE 12

The Productivity and Selectivity of 3% Pt:1.5% Sn on High Purity High surface area SiO$_2$ stabilized with 5% CaSiO$_3$ in hydrogenation of acetic acid was studied in a run of 15 hours duration at 225° C. using a fixed bed continuous reactor system to produce mainly acetaldehyde, ethanol, ethyl acetate through hydrogenation and esterification reactions in a typical range of operating conditions employing 2.5 ml solid catalyst (14/30 mesh, diluted 1:1 (v/v, with quartz chips, 14/30 mesh); at a pressure of 200 psig; with a feed rate of 0.09 g/min HOAc; 160 sccm/min H$_2$; 60 sccm/min N$_2$; and GHSV=6570 h$^{-1}$. The results are set forth in FIGS. 6A and 6B.

EXAMPLE 13

Figure 8:
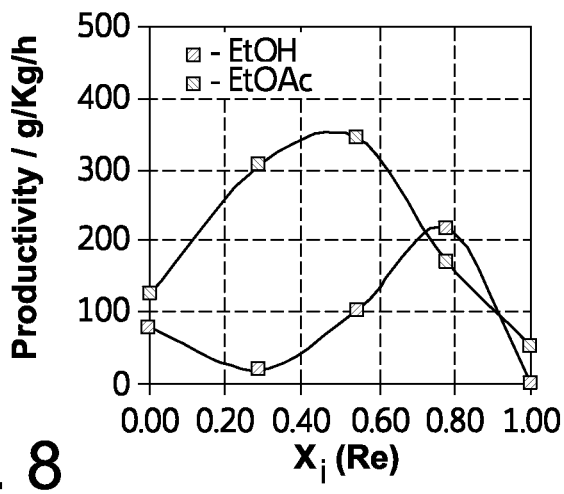
FIGS. 8, 9, and 10 illustrate the effect of the mass fraction of rhenium on hydrogenation of acetic acid using a palladium rhenium on silica catalyst of the present invention.
Figure 9:
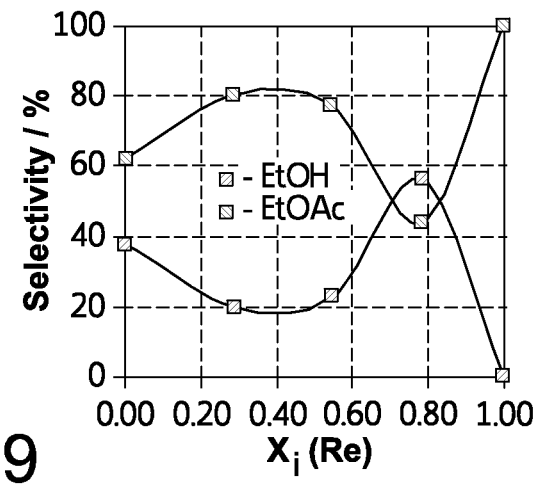
Figure 10:
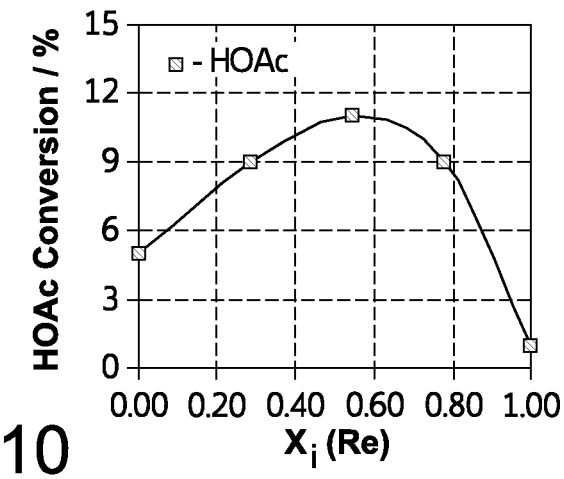
Figure 11:
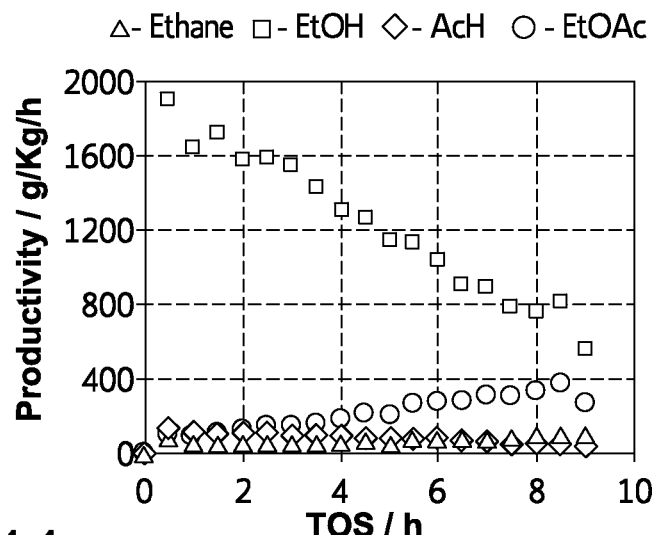
FIGS. 11 and 12 illustrate the performance of a platinum and cobalt catalyst supported on silica.
Figure 12:
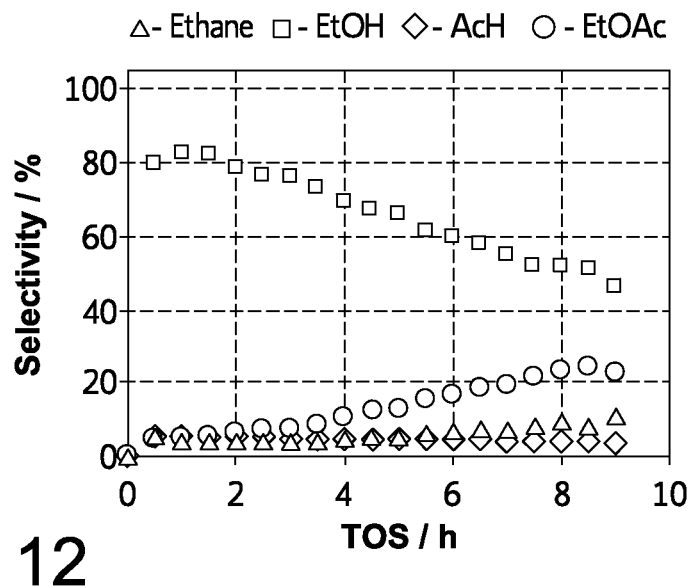

The Productivity and Selectivity of catalysts comprising Re and Pd in SiO$_2$ in which the molar ratio of Re$_x$Pd$_{(1-x)}$ was modified between catalysts was studied by varying the mol fraction of Re at a constant metal loading ([Pt]+[Sn]=1.20 mmol) using 2.5 mL solid catalyst (14/30 mesh, diluted 1:1 (v/v, with quartz chips, 14/30 mesh); at a pressure of 200 psig (14 bar); feeding 0.09 g/min acetic acid; accompanied by 160 sccm/min hydrogen and; 60 sccm/min nitrogen as a diulent; at a temperature of 250° C.; a GHSV=6570 h$^{-1}$; or 12 h of reaction time. While maximum conversion of acetic acid was observed at a Re mol fraction of approximately 0.6, ethanol only becomes the main product at a Re mole fraction of approximately 0.78. At this molar ratio between Re and Pd (indicating "Re$_7$Pd$_2$") selectivity towards ethyl acetate narrowly changes in favor of ethanol. Importantly, and as shown for the Pd/Sn series above, the presence of a specific ratio of the two metals appears to be a key structural requirement for specific product selectivity, i.e., the selectivity shift towards ethanol at [Re]/[Re+Pd]=0.78, c.f. FIGS. 8, 9, and 10 presented in the same format as FIGS. 4A-C except that X$_i$(Re) represents mass fraction of rhenium in the catalyst. In contrast to the Pt/Sn materials, however, maximum conversion of acetic acid and selectivity towards ethanol do not coincide with these materials, and favorable selectivity towards ethanol is only observed at low HOAc conversions. Consequently, maximum productivities are seen for ethyl acetate, rather than for ethanol, c.f., FIG. 8. In addition, the formation of hydrocarbons (methane and ethane; 5.3 and 2.4 wt %, respectively) were observed using a CaSiO$_3$—Re(5)-Pd(2.5) catalyst at an acetic acid conversion of about 30% and a reaction temperature of only 225° C. Although a higher conversion of acetic acid can most likely be obtained by increasing the reaction temperature, the amounts of hydrocarbons will likely increase as well, thus limiting the overall efficiency of a Re/Pd-based catalytic system.

EXAMPLE 14

Initial catalyst screening using a silica-supported platinum (1%) cobalt catalyst (Co loading 10 wt %) on SiO$_2$ resulted in high acetic acid conversion and about 80% selectivity towards ethanol. See FIGS. 11 and 12 in which selectivity and activity are as defined previously with the results for ethanol being represented by squares, results for ethyl acetate being represented by circles, acetaldehyde by diamonds and ethane by triangles. It appears, however, that the catalyst degrades as the acetic acid selectivity declined from about 80% to 42% over the course of nine hours of reaction time. In addition, significant changes in productivity are observed as well, and declining ethanol selectivity was accompanied with an increase in the selectivity towards ethyl acetate and acetaldehyde. Similar results are obtained with 10% cobalt supported on Silica.

EXAMPLE 15

Vaporized acetic acid (0.09 g/min HOAc) and hydrogen (160 sccm/min $H_2$; 60 sccm/min $N_2$) at a pressure of 200 psig were passed over a hydrogenation catalyst of the present invention comprising 3 wt % Pt and 1.8 wt % Sn on a support comprising hydrogen form ZSM-5 molecular sieve at a Temperature of =250° C.; GHSV=6570 $h^{-1}$; 12 h of reaction time. Diethyl ether was obtained at a selectivity of 96% and a productivity of 2646 g/kg/h accompanied by 4% ethyl acetate with 78% acetic acid remaining unreacted.

EXAMPLE 16

Vaporized acetic acid (0.09 g/min HOAc) and hydrogen (160 sccm/min $H_2$; 60 sccm/min $N_2$) at a pressure of 200 psig were passed over a hydrogenation catalyst of the present invention comprising 2 wt % Pt and 1 wt % Sn on a support comprising high surface area graphite at 275° C.; GHSV=6570 $h^{-1}$; 12 h of reaction time. The selectivity to ethyl acetate was 43%, the selectivity to ethanol 57%, the productivity of ethyl acetate was 66 g/kg/hr, the productivity of ethanol was 88 g/kg/hr and the conversion of acetic acid was 12%.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further exemplification is deemed unnecessary. In addition, it should be understood that aspects of the invention and portions of various embodiments and various features recited below and/or in the appended claims may be combined or interchanged either in whole or in part. Furthermore, those of ordinary skill in the art will appreciate that the foregoing description is by way of example only, and is not intended to limit the invention.

There is thus provided in accordance with the present invention, novel processes and catalysts for providing hydrogenated products based on acetic acid.

Embodiment #1, for example is a process for production of ethanol by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst comprising platinum and tin dispersed on a siliceous support wherein the amounts and oxidation states of the platinum and tin, as well as the ratio of platinum to tin, and the siliceous support are selected, composed and controlled such that: (i) at least 80% of the acetic acid converted is converted to ethanol; (ii) less than 4% of the acetic acid is converted to compounds other than compounds chosen from the group consisting of ethanol, acetaldehyde, ethyl acetate, ethylene and mixtures thereof; and the activity of the catalyst declines by less than 10% when exposed to a vaporous mixture of acetic acid and hydrogen at a molar ratio of 10:1 at a pressure of 2 atm and a temperature of 275° C. and a GHSV of 2500 $hr^{-1}$ for a period of 168 hours.

Embodiment #2 is the process of embodiment #1, wherein the hydrogenation catalyst consists essentially of platinum and tin dispersed on the siliceous support and the siliceous support is a modified siliceous support, said modified siliceous support including an effective amount of a support modifier selected from the group consisting of: (i) alkaline earth oxides, (ii) alkali metal oxides, (iii) alkaline earth metasilicates, (iv) alkali metal metasilicates, (v) zinc oxide, (vi) zinc metasilicate and (vii) precursors for any of (i)-(vi), and mixtures of any of (i)-(vii).

Embodiment #3, is a process of embodiment #2, wherein the support modifier is chosen from the group consisting of oxides and metasilicates of sodium, potassium, magnesium, calcium, and zinc as well as precursors therefor and mixtures of any of the foregoing.

Embodiment #4 is a process of embodiment #2, wherein (a) platinum is present in an amount of 0.5% to 5% of the weight of the catalyst; and (b) tin is present in an amount of at least 0.5 to 10%.

Embodiment #5 is a process of embodiment #3, wherein the molar ratio of platinum to tin is between 4:5 and 5:4.

Embodiment #6 is a process of embodiment #2, wherein the support modifier is chosen from the group consisting of metasilicates of sodium, potassium, magnesium, calcium, and zinc as well as precursors therefor and mixtures of any of the foregoing.

Embodiment #7 is a process of embodiment #5, wherein (a) platinum is present in an amount of 0.5% to 5% of the weight of the catalyst; and (b) tin is present in an amount of at least 0.5 to 10%.

Embodiment #8 is a process of embodiment #6, wherein the molar ratio of platinum to tin is between 4:5 and 5:4.

Embodiment #9 is a process of embodiment #2, wherein the support modifier is chosen from the group consisting of oxides and metasilicates of magnesium, calcium, and zinc as well as precursors therefor and mixtures of any of the foregoing.

Embodiment #10 is a process of embodiment #9, wherein: (a) platinum is present in an amount of 0.5% to 5% of the weight of the catalyst; and (b) tin is present in an amount of at least 0.5 to 10%.

Embodiment #11 is a process of embodiment #10, wherein the molar ratio of platinum to tin is between 4:5 and 5:4.

Embodiment #12 is a process of embodiment #2, wherein the support modifier is chosen from the group consisting of metasilicates of magnesium, calcium, and zinc as well as precursors therefor and mixtures of any of the foregoing.

Embodiment #13 is a process of embodiment #12, wherein (a) platinum is present in an amount of 0.5% to 5% of the weight of the catalyst; and (b) tin is present in an amount of at least 0.5 to 10%.

Embodiment #14 is a process of embodiment #12, wherein the molar ratio of platinum to tin is between 4:5 and 5:4.

Embodiment #15 is a process of embodiment #2, wherein the support modifier is chosen from the group consisting of calcium metasilicate, precursors for calcium metasilicate and mixtures of calcium metasilicate and precursors therefor.

Embodiment #16 is a process of embodiment #15, wherein (a) platinum is present in an amount of 0.5% to 5% of the weight of the catalyst; and (b) tin is present in an amount of at least 0.5 to 10%.

Embodiment #17 is a process of embodiment #16, wherein the molar ratio of platinum to tin is between 4:5 and 5:4.

Embodiment #18 s a process of embodiment #2, wherein (a) platinum is present in an amount of 0.5% to 5% of the weight of the catalyst; and (b) tin is present in an amount of at least 0.5 to 10%.

Embodiment #19 is a process of embodiment #16, wherein the molar ratio of platinum to tin is between 4:5 and 5:4.

Embodiment #20 is a process of embodiment #18, wherein the surface area of the support is at least about 100 m²/g.

Embodiment #21 is a process of embodiment #20 wherein the mole ratio of tin to platinum group metal is from about 1:2 to about 2:1.

Embodiment #22 is a process of embodiment #20 wherein the mole ratio of tin to platinum is from about 2:3 to about 3:2.

Embodiment #23 is a process of embodiment #20 wherein the weight ratio of tin to platinum is from about 5:4 to about 4:5.

Embodiment #24 is a process of embodiment #2, wherein the surface area of the support is at least about 150 m²/g.

Embodiment #25 is a process of embodiment #24, wherein (a) platinum is present in an amount of 0.5% to 5% of the weight of the catalyst; and (b) tin is present in an amount of at least 0.5 to 5%.

Embodiment #26 is a process of embodiment #24, wherein the support comprises from at least about 1% to about 10% by weight of calcium silicate.

Embodiment #27 is a process of embodiment #24, wherein the mole ratio of tin to platinum is from about 1:2 to about 2:1.

Embodiment #28 is a process of embodiment #24, wherein the mole ratio of tin to platinum is from about 2:3 to about 3:2.

Embodiment #29 is a process of embodiment #24, wherein the weight ratio of tin to platinum is from about 5:4 to about 4:5.

Embodiment #30 is a process of embodiment #2, wherein the surface area of the support is at least about 200 m²/g.

Embodiment #31 is a process of embodiment #30, wherein the mole ratio of tin to platinum is from about 2:3 to about 3:2.

Embodiment #32 is a process of embodiment #30, wherein the mole ratio of tin to platinum is from about 5:4 to about 4:5.

Embodiment #33 is a process of embodiment #30, wherein the mole ratio of tin to platinum is from about 9:10 to about 10:9.

Embodiment #34 is a process of embodiment #33, wherein the surface area of the modified silicaceous support is at least about 250 m²/g.

Embodiment #35 is a process of embodiment #2, conducted at a temperature of between about 250° C. and 300° C., wherein (a) the surface area of the modified silicaceous support is at least about 250 m²/g; (b) platinum is present in the hydrogenation catalyst in an amount of at least about 0.75% by weight; (c) the mole ratio of tin to platinum is from about 5:4 to about 4:5; and (d) the modified silicaceous support comprises silica having a purity of at least about 95% modified with from at least about 2.5% to about 10% by weight of calcium metasilicate.

Embodiment #36 is a process of embodiment #35, wherein the amount of platinum present is at least 1% by weight.

Embodiment #37 is a process of embodiment #2, conducted at a temperature of between about 250° C. and 300° C., wherein (a) the surface area of the modified silicaceous support is at least about 100 g/m; (b) wherein the mole ratio of tin to platinum is from about 2:3 to about 3:2; and (c) the modified silicaceous support comprises silica having a purity of at least about 95% modified with from at least about 2.5% to about 10% by weight of calcium metasilicate.

Embodiment #38 is a process of embodiment #37, wherein the amount of platinum present is at least 0.75% by weight.

Embodiment #39 is a process of embodiment #38, wherein the catalyst occupies a reactor volume and the gaseous stream comprising hydrogen and acetic acid in the vapor phase is passed through said reactor volume at a space velocity of at least about 1000 hr$^{-1}$.

Embodiment #40 is a process of embodiment #38, wherein the catalyst occupies a reactor volume and the gaseous stream comprising hydrogen and acetic acid in the vapor phase is passed through said reactor volume at a space velocity of at least about 2500 hr$^{-1}$.

Embodiment #41 is a process of embodiment #40, wherein the amounts and oxidation states of the platinum and tin, as well as the ratio of platinum to tin and the modified silicaceous support are controlled such that: (i) at least 90% of the acetic acid converted is converted to ethanol: (ii) less than 2% of the acetic acid is converted to compounds other than compounds chosen from the group consisting of ethanol, acetaldehyde, ethyl acetate, and ethylene and mixtures thereof; and (III) and the activity of the catalyst declines by less than 10% when exposed to a vaporous mixture of acetic acid and hydrogen at a molar ratio of 10:1 at a pressure of 2 atm and a temperature of 275° C. and a GHSV of 2500 hr$^{-1}$ for a period of 336 hours.

Embodiment #42 is a process of embodiment #38, wherein the catalyst occupies a reactor volume and the gaseous stream comprising hydrogen and acetic acid in the vapor phase is passed through said reactor volume at a space velocity of at least about 5000 hr$^{-1}$.

Embodiment #43 is a process of embodiment #42, wherein the amounts and oxidation states of the platinum and tin, as well as the ratio of platinum to tin and the modified silicaceous support are controlled such that: (i) at least 90% of the acetic acid converted is converted to ethanol; (ii) less than 2% of the acetic acid is converted to alkanes; (iii) the activity of the catalyst declines by less than 10% when exposed to a vaporous mixture of acetic acid and hydrogen at a molar ratio of 10:1 at a pressure of 2 atm and a temperature of 275° C. at a GHSV of 2500 hr$^{-1}$ for a period of 168 hours.

Embodiment #44 is a process of embodiment #43, conducted at a temperature of between about 250° C. and 300° C., wherein (a) the surface area of the modified silicaceous support is at least about 200 m²/g; (b) the mole ratio of tin to platinum is from about 5:4 to about 4:5; (c) the modified silicaceous support comprises silica having a purity of at least about 95% and the modifier comprises from at least about 2.5% to about 10% by weight of calcium silicate.

Embodiment #45 is a process for production of ethanol by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst comprising platinum and tin dispersed on an oxidic support wherein the amounts and oxidation states of the platinum and tin, as well as the ratio of platinum to tin, and the oxidic support are selected, composed and controlled such that: (i) at least 80% of the acetic acid converted is converted to ethanol; (ii) less than 4% of the acetic acid is converted to compounds other than compounds chosen from the group consisting of ethanol, acetaldehyde, ethyl acetate, ethylene and mixtures thereof; and the activity of the catalyst declines by less than 10% when exposed to a vaporous mixture of acetic acid and hydrogen at a molar ratio of 10:1 at a pressure of 2 atm and a temperature of 275° C. and a GHSV of 2500 hr$^{-1}$ for a period of 500 hours.

Embodiment #46 is a process of embodiment #45, wherein the hydrogenation catalyst consists essentially of platinum and tin dispersed on the oxidic support and the oxidic support is a modified oxidic support, said modified oxidic support including an effective amount of a support modifier selected from the group consisting of: (i) alkaline earth oxides, (ii) alkali metal oxides, (iii) alkaline earth metasilicates, (iv) alkali metal metasilicates, (v) zinc oxide, (vi) zinc metasilicate and (vii) precursors for any of (i)-(vi), and mixtures of any of (i)-(vii).

Embodiment #47 is a process of embodiment #46, wherein the support modifier is chosen from the group consisting of oxides and metasilicates of sodium, potassium, magnesium, calcium, and zinc as well as precursors therefor and mixtures of any of the foregoing.

Embodiment #48 is a process of embodiment #47, wherein (a) platinum is present in an amount of 0.5% to 5% of the weight of the catalyst; and (b) tin is present in an amount of at least 0.5 to 10%.

Embodiment #49 is a process of embodiment #47, wherein the molar ratio of platinum to tin is between 4:5 and 5:4.

Embodiment #50 is a process of embodiment #46, wherein the support modifier is chosen from the group consisting of metasilicates of sodium, potassium, magnesium, calcium, and zinc as well as precursors therefor and mixtures of any of the foregoing.

Embodiment #51 is a process of embodiment #50, wherein (a) platinum is present in an amount of 0.5% to 5% of the weight of the catalyst; and (b) tin is present in an amount of at least 0.5 to 10%.

Embodiment #52 is a process of embodiment #51 wherein the molar ratio of platinum to tin is between 4:5 and 5:4.

Embodiment #53 is a process of embodiment #46, wherein the support modifier is chosen from the group consisting of oxides and metasilicates of magnesium, calcium, and zinc as well as precursors therefor and mixtures of any of the foregoing.

Embodiment #54 is a process of embodiment #53, wherein (a) platinum is present in an amount of 0.5% to 5% of the weight of the catalyst; and (b) tin is present in an amount of at least 0.5 to 10%.

Embodiment #55 is a process of embodiment #54, wherein the molar ratio of platinum to tin is between 4:5 and 5:4.

Embodiment #56 is a process of embodiment #46, wherein the support modifier is chosen from the group consisting of metasilicates of magnesium, calcium, and zinc as well as precursors therefor and mixtures of any of the foregoing.

Embodiment #57 is a process of embodiment #56, wherein (a) platinum is present in an amount of 0.5% to 5% of the weight of the catalyst; and (b) tin is present in an amount of at least 0.5 to 10%.

Embodiment #58 is a process of embodiment #57, wherein the molar ratio of platinum to tin is between 4:5 and 5:4.

Embodiment #59 is a process of embodiment #46, wherein the support modifier is chosen from the group consisting of calcium metasilicate, precursors for calcium metasilicate and mixtures of calcium metasilicate and precursors therefor.

Embodiment #60 is a process of embodiment #59, wherein (a) platinum is present in an amount of 0.5% to 5% of the weight of the catalyst; and (b) tin is present in an amount of at least 0.5 to 10%.

Embodiment #61 is a process of embodiment #60, wherein the molar ratio of platinum to tin is between 4:5 and 5:4.

Embodiment #62 is a process of embodiment #46, wherein (a) platinum is present in an amount of 0.5% to 5% of the weight of the catalyst; and (b) tin is present in an amount of at least 0.5 to 10%.

Embodiment #63 is a process of embodiment #62, wherein the molar ratio of platinum to tin is between 4:5 and 5:4.

Embodiment #64 is a process of embodiment #62, wherein the surface area of the support is at least about 100 $m^2/g$.

Embodiment #65 is a process of embodiment #64, wherein the mole ratio of tin to platinum group metal is from about 1:2 to about 2:1.

Embodiment #66 is a process of embodiment #64 wherein the mole ratio of tin to platinum is from about 2:3 to about 3:2.

Embodiment #67 is a process of embodiment #64 wherein the weight ratio of tin to platinum is from about 5:4 to about 4:5.

Embodiment #68 is a process of embodiment #46, wherein the surface area of the support is at least about 150 $m^2/g$.

Embodiment #69 is a process of embodiment #68, wherein (a) platinum is present in an amount of 0.5% to 5% of the weight of the catalyst; and (b) tin is present in an amount of at least 0.5 to 5%.

Embodiment #70 is a process of embodiment #68, wherein the support comprises from at least about 1% to about 10% by weight of calcium silicate.

Embodiment #71 is a process of embodiment #68, wherein the mole ratio of tin to platinum is from about 1:2 to about 2:1.

Embodiment #72 is a process of embodiment #68, wherein the mole ratio of tin to platinum is from about 2:3 to about 3:2.

Embodiment #73 is a process of embodiment #68, wherein the weight ratio of tin to platinum is from about 5:4 to about 4:5.

Embodiment #74 is a process of embodiment #46, wherein the surface area of the support is at least about 200 $m^2/g$.

Embodiment #75 is a process of embodiment #74, wherein the mole ratio of tin to platinum is from about 2:3 to about 3:2.

Embodiment #76 is a process of embodiment #74, wherein the mole ratio of tin to platinum is from about 5:4 to about 4:5.

Embodiment #77 is a process of embodiment #74, wherein the mole ratio of tin to platinum is from about 9:10 to about 10:9.

Embodiment #78 is a process for production of ethanol by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of platinum and tin dispersed on a modified stabilized silicaceous support, the modified stabilized silicaceous support comprising silica having a purity of at least about 95% by weight modified with an stabilizer-modifier chosen from the group consisting of (i) alkaline earth oxides, (ii) alkali metal oxides, (iii) alkaline earth metasilicates, (iv) alkali metal metasilicates, (v) zinc oxide, (vi) zinc metasilicate and (vii) precursors for any of (i)-(vi), and mixtures of any of (i)-(vii), wherein the amounts and oxidation states of the platinum and tin, the ratio of platinum to tin and the relative proportions of stabilizer-modifier to silica in the modified stabilized silicaceous support as well as the purity of the silica in the modified stabilized silicaceous support are controlled such that at least 80% of the acetic acid converted is converted to ethanol and less than 4% of the acetic acid is converted to compounds other than compounds chosen from the group consisting of ethanol, acetaldehyde, ethyl acetate, ethylene and mixtures thereof.

Embodiment #79 is a process of embodiment #78, wherein (a) platinum is present in an amount of 0.5% to 5% of the weight of the catalyst; and (b) tin is present in an amount of at least 0.5 to 10%.

Embodiment #80 is a process of embodiment #79, wherein the surface area of the modified stabilized silicaceous support is at least about 100 $m^2/g$.

Embodiment #81 is a process of embodiment #80, wherein the mole ratio of tin to platinum group metal is from about 1:2 to about 2:1.

Embodiment #82 is a process of embodiment #80, wherein the mole ratio of tin to platinum is from about 2:3 to about 3:2.

Embodiment #83 is a process of embodiment #79, wherein the weight ratio of tin to platinum is from about 5:4 to about 4:5.

Embodiment #84 is a process of embodiment #78, wherein the surface area of the modified stabilized silicaceous support is at least about 150 m$^2$/g.

Embodiment #85 is a process of embodiment #84, wherein (a) platinum is present in an amount of 0.5% to 5% of the weight of the catalyst; and (b) tin is present in an amount of at least 0.5 to 5%.

Embodiment #86 is a process of embodiment #84, wherein the modified stabilized silicaceous support comprises from at least about 1% to about 10% by weight of calcium silicate.

Embodiment #87 is a process of embodiment #84, wherein the mole ratio of tin to platinum is from about 1:2 to about 2:1.

Embodiment #88 is a process of embodiment #84, wherein the mole ratio of tin to platinum is from about 2:3 to about 3:2.

Embodiment #89 is a process of embodiment #84, wherein the weight ratio of tin to platinum is from about 5:4 to about 4:5.

Embodiment #90 is a process of embodiment #87, wherein the surface area of the modified stabilized silicaceous support is at least about 200 m$^2$/g.

Embodiment #91 is a process of embodiment #90, wherein the mole ratio of tin to platinum is from about 9:10 to about 10:9.

Embodiment #92 is a process of embodiment #90, wherein the mole ratio of tin to platinum is from about 2:3 to about 3:2.

Embodiment #93 is a process of embodiment #90, wherein the mole ratio of tin to platinum is from about 5:4 to about 4:5.

Embodiment #94 is a process of embodiment #90, wherein the surface area of the modified stabilized silicaceous support is at least about 250 m$^2$/g.

Embodiment #95 is a process of embodiment #78, conducted at a temperature of between about 250° C. and 300° C., wherein (a) the surface area of the modified stabilized silicaceous support is at least about 250 m$^2$/g; (b) platinum is present in the hydrogenation catalyst in an amount of at least about 0.75% by weight; (c) the mole ratio of tin to platinum is from about 5:4 to about 4:5; and (d) the modified stabilized silicaceous support comprises from at least about 2.5% to about 10% by weight of calcium silicate.

Embodiment #96 is a process of embodiment #95, wherein the amount of platinum present is at least 1% by weight.

Embodiment #97 is a process of embodiment #78 conducted at a temperature of between about 250° C. and 300° C., wherein (a) the surface area of the modified stabilized silicaceous support is at least about 100 g/m; (b) wherein the mole ratio of tin to platinum is from about 2:3 to about 3:2; and (c) the modified stabilized silicaceous support comprises from at least about 2.5% to about 10% by weight of calcium silicate.

Embodiment #98 is a process of embodiment #97, wherein the amount of platinum present is at least 0.75% by weight.

Embodiment #99 is a process of embodiment #98, wherein the catalyst occupies a reactor volume and the gaseous stream comprising hydrogen and acetic acid in the vapor phase is passed through said reactor volume at a space velocity of at least about 1000 hr$^{-1}$.

Embodiment #100 is a process of embodiment #98, wherein the catalyst occupies a reactor volume and the gaseous stream comprising hydrogen and acetic acid in the vapor phase is passed through said reactor volume at a space velocity of at least about 2500 hr$^{-1}$.

Embodiment #101 is a process of embodiment #100, wherein the amounts and oxidation states of the platinum and tin, as well as the ratio of platinum to tin and the composition of the modified stabilized silicaceous support are controlled such that at least 90% of the acetic acid converted is converted to ethanol and less than 2% of the acetic acid is converted to compounds other than compounds chosen from the group consisting of ethanol, acetaldehyde, ethyl acetate, and ethylene and mixtures thereof.

Embodiment #102 is a process of embodiment #98, wherein the catalyst occupies a reactor volume and the gaseous stream comprising hydrogen and acetic acid in the vapor phase is passed through said reactor volume at a space velocity of at least about 5000 hr$^{-1}$.

Embodiment #103 is a process of embodiment #79, wherein the amounts and oxidation states of the platinum and tin, as well as the ratio of platinum to tin and the composition of the modified stabilized silicaceous support are controlled such that at least 90% of the acetic acid converted is converted to ethanol and less than 2% of the acetic acid is converted to alkanes.

Embodiment #104 is a process of embodiment #79, conducted at a temperature of between about 250° C. and 300° C., wherein (a) wherein the amounts and oxidation states of the platinum and tin, as well as the ratio of platinum to tin and the acidity of the modified stabilized silicaceous support are controlled such that at least 90% of the acetic acid converted is converted to ethanol and less than 1% of the acetic acid is converted to alkanes; (b) the surface area of the modified stabilized silicaceous support is at least about 200 m$^2$/g; (c) the mole ratio of tin to platinum is from about 5:4 to about 4:5; (d) the modified stabilized silicaceous support comprises from at least about 2.5% to about 10% by weight of calcium silicate.

Embodiment #105 is a process for production of ethanol by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of: a catalytic metal chosen from the group consisting of: Fe, Co, Cu, Ni, Ru, Rh, Pd, Ir, Pt, Sn, Re, Os, Ti, Zn, Cr, Mo and W as well as mixtures thereof in an amount of from about 0.1% to about 10% by weight; and an optional promoter, dispersed on a suitable support wherein the amounts and oxidation states of the catalytic metal(s) and the compositions of the support and optional promoter as well as reaction conditions are controlled such that: (i) at least 80% of the acetic acid converted is converted to ethanol; (ii) less than 4% of the acetic acid is converted to compounds other than compounds chosen from the group consisting of ethanol, acetaldehyde, ethyl acetate, ethylene, diethyl ether and mixtures thereof; and the activity of the catalyst declines by less than 10% when exposed to a vaporous mixture of acetic acid and hydrogen at a molar ratio of 10:1 at a pressure of 2 atm and a temperature of 275° C. and a GHSV of 2500 hr$^{-1}$ for a period of 500 hours.

Embodiment #106 is a process of embodiment #105, wherein the support is an oxidic support modified with a modifier selected from the group consisting of oxides and metasilicates of sodium, potassium, magnesium, calcium, scandium, yttrium and zinc as well as precursors therefor and mixtures of any of the foregoing.

Embodiment #107 is a process of embodiment #105, wherein the support is a carbon support and the catalytic metals include platinum and tin.

Embodiment #108 is a process of embodiment #107, wherein the carbon support is modified with a reducible metal oxide.

Embodiment #109 is a process for production of ethanol by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of metallic components dispersed on an oxidic support, said hydrogenation catalyst having the composition:

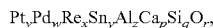

wherein v and y are between 3:2 and 2:3; w and x are between 1:3 and 1:5, wherein p and z and the relative locations of aluminum and calcium atoms present are controlled such that Bronsted acid sites present upon the surface thereof are counteracted by calcium silicate; p and q are selected such that p:q is from 1:20 to 1:200 with r being selected to satisfy valence requirements and v and w are selected such that $$0.005 \leq \frac{(3.25v + 1.75w)}{q} \leq 0.05.$$

Embodiment #110 is a process of embodiment #109, wherein the hydrogenation catalyst has a surface area of at least about 100 m²/g and wherein z and p are controlled such that p≥z.

Embodiment #111 is a process of embodiment #110, wherein p is selected, in view of any minor impurities present, to ensure that the surface of the support is essentially free of Bronsted acid sites.

Embodiment #112 is a process for hydrogenating acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of: a catalytic metal chosen from the group consisting of: Fe, Co, Cu, Ni, Ru, Rh, Pd, Ir, Pt, Sn, Re, Os, Ti, Zn, Cr, Mo and W as well as mixtures thereof in an amount of from about 0.1% to about 10% by weight; and an optional promoter, dispersed on a suitable support wherein the amounts and oxidation states of the catalytic metal(s) and the compositions of the support and optional promoter as well as reaction conditions are controlled such that less than 4% of the acetic acid is converted to compounds other than compounds chosen from the group consisting of ethanol, acetaldehyde, ethyl acetate, ethylene, diethyl ether and mixtures thereof; and the activity of the catalyst declines by less than 10% when exposed to a vaporous mixture of acetic acid and hydrogen at a molar ratio of 10:1 at a pressure of 2 atm and a temperature of 275° C. and a GHSV of 2500 hr⁻¹ for a period of 500 hours, with the further provisos: (i) wherein the support is an oxidic support modified with a modifier selected from the group consisting of oxides and metasilicates of sodium, potassium, magnesium, calcium, scandium, yttrium and zinc as well as precursors therefor and mixtures of any of the foregoing; (ii) the support is a carbon support and the catalytic metals include platinum and tin or (iii) the support is a carbon support modified with a reducible metal oxide.

Embodiment #113 is a process for hydrogenating alkanoic acids comprising passing a gaseous stream comprising hydrogen and an alkanoic acid in the vapor phase in a mole ratio of hydrogen to alkanoic acid of at least about 2:1 at a temperature of between about 125° C. and 350° C. over a hydrogenation catalyst comprising: a platinum group metal chosen from the group consisting of platinum, palladium, rhenium and mixtures thereof on a silicaceous support chosen from the group consisting of silica, calcium metasilicate and calcium metasilicate promoted silica; and a promoter chosen the group consisting of tin, rhenium and mixtures thereof, the silicaceous support being optionally promoted with a promoter chosen from the group consisting of (a) a promoter chosen from the group consisting of alkali metals; alkaline earth elements and zinc in an amount of 1 to 5% by weight of the catalyst; (b) a redox promoter chosen from the group consisting of: $WO_3$; $MoO_3$; $Fe_2O_3$ and $Cr_2O_3$ in an amount of 1 to 50% by weight of the catalyst; and (c) an acidic modifier chosen from the group consisting of $TiO_2$; $ZrO_2$; $Nb_2O_5$; $Ta_2O_5$; and $Al_2O_3$ in an amount of 1 to 50% by weight of the catalyst.

Embodiment #114 is a process of embodiment #113, wherein said alkanoic acid is acetic acid, and wherein (a) at least one of platinum and palladium is present in an amount of 0.25% to 5% of the weight of the catalyst; (b) the combined amount of platinum and palladium present is at least 0.5% by weight of catalyst; and (c) the combined amount of rhenium and tin present is at least 0.5 to 10% by weight.

Embodiment #115 is a process of embodiment #114, wherein the surface area of the silicaceous support is at least about 150 m²/g.

Embodiment #116 is a process of embodiment #115, wherein (a) the amounts and oxidation states of the platinum group metals, the rhenium and tin promoters, as well as (b) the mole ratio of platinum group metal to combined moles of rhenium and tin present; and (c) the number of Bronsted acid sites on the silicaceous support are controlled such that at least 80% of the acetic acid converted is converted to a compound chosen from the group consisting of ethanol and ethyl acetate while less than 4% of the acetic acid is converted to compounds other than compounds chosen from the group consisting of ethanol, acetaldehyde, ethyl acetate, ethylene and mixtures thereof.

Embodiment #117 is a process of embodiment #115, wherein (a) at least one of platinum and palladium is present in an amount of 0.5% to 5% of the weight of the catalyst; (b) the combined amount of platinum and palladium present is at least 0.75% to 5% of the weight of the catalyst; and (c) the combined amount of tin and rhenium present is at least 1.0% by weight of catalyst.

Embodiment #118 is a process of embodiment #117, wherein (a) the amounts and oxidation states of (i) the platinum group metals, (ii) the rhenium and tin promoters, as well as (iii) the ratio of platinum group metal to rhenium and tin promoters; and (iv) the acidity of the silicaceous support are controlled such that at least 80% of the acetic acid converted is converted to ethanol and less than 4% of the acetic acid is converted to compounds other than compounds chosen from the group consisting of ethanol, acetaldehyde, ethyl acetate, ethylene and mixtures thereof.

Embodiment #119 is a process of embodiment #118, wherein the combined weight of rhenium and tin present is from about 1 to 10% by weight of the catalyst.

Embodiment #120 is a process of embodiment #119, wherein the mole ratio of platinum group metal to moles of rhenium and tin combined is from about 1:2 to about 2:1.

Embodiment #121 is a process for hydrogenation of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of metallic components dispersed on an oxidic support, said hydrogenation catalyst having the composition:

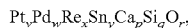

wherein the ratio of v:y is between 3:2 and 2:3; the ratio of w:x is between 1:3 and 1:5, p and q are selected such that p:q is from 1:20 to 1:200 with r being selected to satisfy valence requirements and v and w being selected such that $$0.005 \leq \frac{(3.25v + 1.75w)}{q} \leq 0.05.$$

Embodiment #122 is a process of embodiment #121, wherein the process conditions and values of v, w, x, y, p, q, and r are chosen such that at least 90% of the acetic acid converted is converted to a compound chosen from the group consisting of ethanol and ethyl acetate while less than 4% of the acetic acid is converted to alkanes.

Embodiment #123 is a process of embodiment #122, wherein the process conditions and values of v, w, x, y, p, q, and r are chosen such that at least 90% of the acetic acid converted is converted to ethanol and less than 2% of the acetic acid is converted to alkanes.

Embodiment #124 is a process of embodiment #122, wherein p is selected, in view of any minor impurities present, to ensure that the surface of the support is essentially basic.

Embodiment #125 is a process for hydrogenation of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of metallic components dispersed on an oxidic support, said hydrogenation catalyst having the composition:

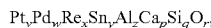

wherein v and y are between 3:2 and 2:3; w and x are between 1:3 and 1:5, wherein p and z and the relative locations of aluminum and calcium atoms present are controlled such that Bronsted acid sites present upon the surface thereof are counteracted by calcium silicate; p and q are selected such that p:q is from 1:20 to 1:200 with r being selected to satisfy valence requirements and v and w are selected such that $$0.005 \leq \frac{(3.25v + 1.75w)}{q} \leq 0.05.$$

Embodiment #126 is a process of embodiment #125, wherein the hydrogenation catalyst has a surface area of at least about 100 m²/g and wherein z and p are controlled such that p≥z.

Embodiment #127 is a process of embodiment #125, wherein p is selected, in view of any minor impurities present, to ensure that the surface of the support is essentially free of Bronsted acid sites.

Embodiment #128 is a process for hydrogenating alkanoic acids comprising passing a gaseous stream comprising hydrogen and an alkanoic acid in the vapor phase in a mole ratio of hydrogen to alkanoic acid of at least about 5:1 at a temperature of between about 125° C. and 350° C. at a GHSV of at least about 1000 hr$^{-1}$ at a pressure of at least 2 atm over a hydrogenation catalyst, said hydrogenation catalyst comprising (a) a platinum group metal chosen from the group consisting of platinum, palladium and mixtures thereof on a silicaceous support chosen from the group consisting of silica, calcium metasilicate and calcium metasilicate promoted silica; and (b) a metallic promoter chosen the group consisting of tin and rhenium and mixtures thereof, (c) the silicaceous support being optionally promoted with a second promoter chosen from the group consisting of: (i) a donor promoter chosen from the group consisting of alkali metals; alkaline earth elements and zinc in an amount of 1 to 5% by weight of the catalyst; (ii) a redox promoter chosen from the group consisting of: $WO_3$; $MoO_3$; $Fe_2O_3$ and $Cr_2O_3$ in an amount of 1 to 50% by weight of the catalyst; (iii) an acidic modifier chosen from the group consisting of $TiO_2$; $ZrO_2$; $Nb_2O_5$; $Ta_2O_5$; and $Al_2O_3$ in an amount of 1 to 50% by weight of the catalyst; and (iv) combinations of i, ii, and iii.

Embodiment #129 is a process of embodiment #128, wherein said alkanoic acid is acetic acid, and wherein (a) platinum, if present, is present in an amount of 0.5% to 5% of the weight of the catalyst; (b) palladium, if present, is present in an amount of 0.5% to 5% of the weight of the catalyst; and (c) the metallic promoter is present in an amount of at least 0.5 to 10%.

Embodiment #130 is a process of embodiment #129, wherein the surface area of the silicaceous support is at least about 150 m²/g.

Embodiment #131 is a process of embodiment #130, wherein (a) platinum is present in an amount of 1% to 5% of the weight of the catalyst; (b) palladium, if present, is present in an amount of 0.25% to 5% of the weight of the catalyst; and (c) the combined amount of platinum and palladium present is at least 1.25% by weight of catalyst.

Embodiment #132 is a process of embodiment #131, wherein tin is present in an amount of 1 to 3% by weight of the catalyst.

Embodiment #133 is a process of embodiment #132, wherein the mole ratio of tin to platinum group metal is from about 1:2 to about 2:1.

Embodiment #134 is a process of embodiment #132, wherein the molar ratio of tin to platinum is from about 5:4 to about 4:5.

Embodiment #135 is a process of embodiment #132, wherein the silicaceous support is essentially free of Bronsted acid sites not counteracted with calcium metasilicate and the surface area thereof is at least about 200 m²/g.

Embodiment #136 is a process of embodiment #132, wherein the weight ratio of tin to platinum group metal is from about 2:3 to about 3:2.

Embodiment #137 is a process of embodiment #128, wherein the mole ratio of tin to platinum is from about 2:3 to about 3:2.

Embodiment #138 is a process for hydrogenating acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of: a catalytic metal chosen from the group consisting of: Fe, Co, Cu, Ni, Ru, Rh, Pd, Ir, Pt, Sn, Os, Ti, Zn, Cr, Mo and W as well as mixtures thereof in an amount of from about 0.1% to about 10% by weight; and an optional promoter, dispersed on a suitable support wherein the amounts and oxidation states of the catalytic metal(s) and the compositions of the support and optional promoter as well as reaction conditions are controlled such that less than 4% of the acetic acid is converted to compounds other than compounds chosen from the group consisting of ethanol, acetaldehyde, ethyl acetate, ethylene, diethyl ether and mixtures thereof; and the activity of the catalyst declines by less than 10% when exposed to a vaporous mixture of acetic acid and hydrogen at a molar ratio of 10:1 at a pressure of 2 atm and a temperature of 275° C. and a GHSV of 2500 hr$^{-1}$ for a period of 500 hours.

Embodiment #139 is a process of embodiment #138, wherein the support is selected from: molecular sieve supports; modified siliceous supports modified with a modifier selected from the group consisting of oxides and metasilicates of sodium, potassium, magnesium, calcium, scandium, yttrium and zinc as well as precursors therefor and mixtures of any of the foregoing, and carbon supports.

Embodiment #140 is a process of embodiment #139, wherein the catalytic metals include platinum and tin and the selectivity to diethyl ether is over 80%.

Embodiment #141 is a process of embodiment #107, wherein support is a zeolite support, and the selectivity to diethyl ether is over 90%.

Embodiment #142 is a process for production of ethanol and ethyl acetate by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst comprising: (a) a platinum group metal chosen from the group consisting of platinum, and mixtures of platinum and palladium on a siliceous support chosen from the group consisting of silica, and silica promoted with up to about 7.5 calcium metasilicate, the amount of platinum group metal present being at least about 2.0%, the amount of platinum present being at least about 1.5%; and (b) a metallic promoter chosen from the group consisting from the group consisting of rhenium and tin an amount of between about 1% and 2% by weight of the catalyst, the mole ratio of platinum to metallic promoter being between about 3:1 and 1:2; (c) the siliceous support being optionally promoted with a second promoter chosen from the group consisting of (i) a donor promoter chosen from the group consisting of alkali metals; alkaline earth elements and zinc in an amount of 1 to 5% by weight of the catalyst; (ii) a redox promoter chosen from the group consisting of: $WO_3$; $MoO_3$; $Fe_2O_3$ and $Cr_2O_3$ in an amount of 1 to 50% by weight of the catalyst; (iii) an acidic modifier chosen from the group consisting of $TiO_2$; $ZrO_2$; $Nb_2O_5$; $Ta_2O5$; and $Al_2O_3$ in an amount of 1 to 50% by weight of the catalyst; and (iv) combinations of i, ii, and iii.

Embodiment #143 is a process of embodiment #142, wherein the mole ratio of metallic promoter to platinum group metal is from about 2:3 to about 3:2.

Embodiment #144 is a process of embodiment #142, wherein the mole ratio of metallic promoter to platinum group metal is from about 5:4 to about 4:5.

Embodiment #145 is a process of embodiment #142, wherein the surface area of the siliceous support is at least about 200 m$^2$/g and the amount of calcium metasilicate is sufficient to render the surface of the siliceous support essentially free of Bronsted Acidity.

Embodiment #146 is a process of embodiment #145, wherein the mole ratio of metallic promoter to platinum group metal is from about 2:3 to about 3:2.

Embodiment #147 is a process of embodiment #146, wherein the surface area of the siliceous support is at least about 200 m$^2$/g and the mole number of Bronsted Acid sites present on the surface thereof is no more than the mole number of Bronsted Acid sites present on the surface of Saint-Gobain N or Pro SS61138 silica.

Embodiment #148 is a process of embodiment #142, wherein the surface area of the siliceous support is at least about 250 m$^2$/g and the mole number of Bronsted Acid sites present on the surface thereof is no more than one half the mole number of Bronsted Acid sites present on the surface of Saint-Gobain N or Pro HSA SS61138 silica.

Embodiment #149 is a process of embodiment #142, conducted at a temperature of between about 250° C. and 300° C., wherein (a) the hydrogenation catalyst comprises palladium on a siliceous support chosen from the group consisting of silica, and silica promoted with up to about 7.5 calcium metasilicate, the amount of palladium present being at least about 1.5%; and (b) the metallic promoter is rhenium in an amount of between about 1% and 10% by weight of the catalyst, the mole ratio of rhenium to palladium being between about 3:1 and 5:1.

Embodiment #150 is a process for reduction of acetic acid of embodiment #142, wherein the hydrogenation catalyst consists essentially of platinum, thereof on a siliceous support consisting essentially of silica promoted with from about 3 up to about 7.5% calcium silicate, the amount of platinum present being at least about 1.0%, and a tin promoter in an amount of between about 1% and 5% by weight of the catalyst, the mole ratio of platinum to tin being between about 9:10 and 10:9.

Embodiment #151 is a process for reduction of acetic acid of embodiment #142, wherein the amount of platinum group metal present is at least about 2.0%, the amount of platinum present being at least about 1.5%, and a tin promoter in an amount of between about 1% and 5% by weight of the catalyst, the mole ratio of platinum to tin being between about 9:10 and 10:9.

Embodiment #152 is a process of embodiment #151, conducted at a temperature of between about 250° C. and 300° C., wherein said hydrogenation catalyst comprises: between 2.5 and 3.5 weight percent platinum, between 2 weight % and 5 weight % tin dispersed on high surface area silica having a surface area of at least 200 m$^2$ per gram, said high surface area silica being promoted with between 4 and 7.5% calcium metasilicate.

Embodiment #153 is a process for production of a stream comprising ethanol and at least about 40% ethyl acetate by reduction of acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of metallic components dispersed on an oxidic support, said hydrogenation catalyst having the composition:

wherein the ratio of v and y is between 3:2 and 2:3; the ratio of w and x is between 1:3 and 1:5, wherein p and z and p, q and n are selected such that $$0.005 \leq \frac{2p}{q + 1.33n + 1.77z} \leq 0.2$$

with r being selected to satisfy valence requirements and v and w are selected such that $$0.005 \leq \frac{(3.25v + 1.75w)}{q + 1.33n + 1.77z} \leq 0.05.$$

Embodiment #154 is a process of embodiment #153, wherein the hydrogenation catalyst has a surface area of at least about 100 m$^2$/g.

Embodiment #155 is a process for hydrogenating acetic acid comprising passing a gaseous stream comprising hydrogen and acetic acid in the vapor phase in a mole ratio of hydrogen to acetic acid of at least about 4:1 at a temperature of between about 225° C. and 300° C. over a hydrogenation catalyst consisting essentially of: a catalytic metal chosen from the group consisting of: Fe, Co, Cu, Ni, Ru, Rh, Pd, Ir, Pt, Sn, Os, Ti, Zn, Cr, Mo and W as well as mixtures thereof in an amount of from about 0.1% to about 10% by weight; and an optional promoter, dispersed on a suitable support wherein the amounts and oxidation states of the catalytic metal(s) and the compositions of the support and optional promoter as well as reaction conditions are controlled such that: i) more more than 50% of the acetic acid converted is converted to ethyl acetate; (ii) less than 4% of the acetic acid is converted to compounds other than compounds chosen from the group consisting of ethanol, acetaldehyde, ethyl acetate, ethylene, diethyl ether and mixtures thereof; and the activity of the catalyst declines by less than 10% when exposed to a vaporous mixture of acetic acid and hydrogen at a molar ratio of 10:1 at a pressure of 2 atm and a temperature of 275° C. and a GHSV of 2500 $hr^{-1}$ for a period of 500 hours.

Embodiment #156 is a particulate catalyst for hydrogenation of alkanoic acids to the corresponding alkanol, comprising: (a) a platinum group metal chosen from the group consisting of platinum, palladium and mixtures thereof on a siliceous support chosen from the group consisting of silica, and silica promoted with from about 3.0 up to about 7.5 calcium metasilicate, the surface area of the siliceous support being at least about 150 $m^2/g$; and (b) a tin promoter in an amount of between about 1% and 3% by weight of the catalyst, the mole ratio of platinum to tin being between about 4:3 and 3:4; (c) the composition and structure of the siliceous support being chosen such that the surface thereof is essentially free of Bronsted acid sites not counteracted with calcium metasilicate.

Embodiment #157 is a hydrogenation catalyst of embodiment #156, wherein the total weight of platinum group metals present is between 2 and 4%, the amount of platinum present is at least 2%, the weight ratio of platinum to tin being between 4:5 and 5:4, and the amount of calcium silicate present is between 3 and 7.5%.

Embodiment #158 is a particulate hydrogenation catalyst consisting essentially of: a siliceous support having dispersed thereupon a platinum group metal chosen the group consisting of platinum, palladium, and mixtures thereof with a promoter chosen from the group consisting of tin, cobalt and rhenium, the siliceous support having a surface area of at least about 175 $m^2/g$ and being chosen from the group consisting of silica, calcium metasilicate and calcium metasilicate promoted silica having calcium metasilicate being disposed on the surface thereof, the surface of the siliceous support being essentially free of Bronsted acid sites due to alumina unbalanced by calcium.

Embodiment #159 is a hydrogenation catalyst of embodiment #158, wherein the total weight of platinum group metals present is between 0.5% and 2%, the amount of palladium present is at least 0.5%, the promoter is rhenium, the weight ratio of rhenium to palladium being between 10:1 and 2:1, and the amount of calcium meta-silicate is between 3 and 90%.

Embodiment #160 is a hydrogenation catalyst of embodiment #159, wherein the total weight of platinum group metals present is between 0.5 and 2%, the amount of platinum present is at least 0.5%, the promoter is cobalt, the weight ratio of cobalt to platinum being between 20:1 and 3:1, and the amount of calcium silicate is between 3 and 90%.

Embodiment #161 is a hydrogenation catalyst of embodiment #158, wherein the total weight of platinum group metals present is between 0.5 and 2%, the amount of palladium present is at least 0.5%, the promoter is cobalt, the weight ratio of cobalt to palladium being between 20:1 and 3:1, and the amount of calcium silicate is between 3 and 90%.

Embodiment #162 is a hydrogenation catalyst comprising: between 2.5 and 3.5 weight percent platinum, between 3 weight % and 5 weight % tin dispersed on high surface area pyrogenic silica having a surface area of at least 200 $m^2$ per gram, said high surface area silica being promoted with between 4 and 6% calcium metasilicate, the molar ratio of platinum to tin being between 4:5 and 5:4.

Embodiment #163 is a hydrogenation catalyst comprising: between 0.5 and 2.5 weight percent palladium, between 2 weight % and 7 weight % rhenium, the weight ratio of rhenium to palladium being at least 1.5:1.0, said rhenium and palladium being dispersed on a siliceous support, said siliceous support comprising at least 80% calcium metasilicate.

Embodiment #164 is a particulate catalyst for hydrogenation of alkanoic acids to the corresponding alkanol, comprising: (a) a platinum group metal chosen from the group consisting of platinum, palladium and mixtures thereof on a siliceous support chosen from the group consisting of modified stabilized siliceous support, said siliceous support being modified and stabilized with a stabilizer-modifier chosen from the group consisting of (i) alkaline earth oxides, (ii) alkali metal oxides, (iii) alkaline earth metasilicates, (iv) alkali metal metasilicates, (v) zinc oxide, (vi) zinc metasilicate and (vii) precursors for any of (i)-(vi), and mixtures of any of (i)-(vii), the surface area of the modified stabilized siliceous support being at least about 150 $m^2/g$; and (b) a tin promoter in an amount of between about 1% and 3% by weight of the catalyst, the mole ratio of platinum to tin being between about 4:3 and 3:4.

Embodiment #165 is a hydrogenation catalyst of embodiment #164, wherein the total weight of platinum group metals present is between 2 and 4%, the amount of platinum present is at least 2%, the weight ratio of platinum to tin being between 4:5 and 5:4, and the amount of stabilizer-modifier present is between 3 and 7.5%.

Embodiment #166 is a hydrogenation catalyst of embodiment #165, wherein the support modifier is chosen from the group consisting of oxides and metasilicates of sodium, potassium, magnesium, calcium, and zinc as well as precursors therefor and mixtures of any of the foregoing.

Embodiment #167 is a hydrogenation catalyst of embodiment #165, wherein the support modifier is chosen from the group consisting of oxides and metasilicates of sodium, potassium, magnesium, calcium, and zinc as well as precursors therefor and mixtures of any of the foregoing.

Embodiment #168 is a hydrogenation catalyst of embodiment #165, wherein the support modifier is chosen from the group consisting of oxides and metasilicates of magnesium, calcium, and zinc as well as precursors therefor and mixtures of any of the foregoing.

Embodiment #169 is a hydrogenation catalyst of embodiment #165, wherein the support modifier is chosen from the group consisting of oxides and metasilicates of magnesium, calcium, and zinc as well as precursors therefor and mixtures of any of the foregoing.

Embodiment #170 is a hydrogenation catalyst of embodiment #165, wherein the support modifier is chosen from the group consisting of calcium metasilicate, precursors for calcium metasilicate and mixtures of calcium metasilicate and precursors therefor.

Embodiment #171 is a hydrogenation catalyst of embodiment #164, wherein the support modifier is chosen from the group consisting of oxides and metasilicates of sodium, potassium, magnesium, calcium, and zinc as well as precursors therefor and mixtures of any of the foregoing.

Embodiment #172 is a hydrogenation catalyst of embodiment #164, wherein the support modifier is chosen from the group consisting of oxides and metasilicates of sodium, potassium, magnesium, calcium, and zinc as well as precursors therefor and mixtures of any of the foregoing.

Embodiment #173 is a hydrogenation catalyst of embodiment #164, wherein the support modifier is chosen from the group consisting of oxides and metasilicates of magnesium, calcium, and zinc as well as precursors therefor and mixtures of any of the foregoing.

Embodiment #174 is a hydrogenation catalyst of embodiment #164, wherein the support modifier is chosen from the group consisting of oxides and metasilicates of magnesium, calcium, and zinc as well as precursors therefor and mixtures of any of the foregoing.

Embodiment #175 is a hydrogenation catalyst of embodiment #164, wherein the support modifier is chosen from the group consisting of calcium metasilicate, precursors for calcium metasilicate and mixtures of calcium metasilicate and precursors therefor.

Embodiment #176 is a particulate hydrogenation catalyst consisting essentially of: a modified stabilized silicaceous support having dispersed thereupon a platinum group metal chosen the group consisting of platinum, palladium, and mixtures thereof with a promoter chosen from the group consisting of tin, cobalt and rhenium, the silicaceous support comprising silica having a purity of at least 95% and having a surface area of at least about 175 $m^2/g$ modified and stabilized with a stabilizer-modifier chosen from the group consisting of (i) alkaline earth oxides, (ii) alkali metal oxides, (iii) alkaline earth metasilicates, (iv) alkali metal metasilicates, (v) zinc oxide, (vi) zinc metasilicate and (vii) precursors for any of (i)-(vi), and mixtures of any of (i)-(vii), the surface of the silicaceous support being essentially free of Bronsted acid sites due to alumina unbalanced by stabilizer-modifier.

Embodiment #177 is a hydrogenation catalyst of embodiment #176, wherein the total weight of platinum group metals present is between 0.5% and 2%, the amount of palladium present is at least 0.5%, the promoter is rhenium, the weight ratio of rhenium to palladium being between 10:1 and 2:1, and the amount of support-modifier is between 3 and 90%.

Embodiment #178 is a hydrogenation catalyst of embodiment #177, wherein the support modifier is chosen from the group consisting of oxides and metasilicates of sodium, potassium, magnesium, calcium, and zinc as well as precursors therefor and mixtures of any of the foregoing.

Embodiment #179 is a hydrogenation catalyst of embodiment #177, wherein the support modifier is chosen from the group consisting of oxides and metasilicates of sodium, potassium, magnesium, calcium, and zinc as well as precursors therefor and mixtures of any of the foregoing.

Embodiment #180 is a hydrogenation catalyst of embodiment #177, wherein the support modifier is chosen from the group consisting of oxides and metasilicates of magnesium, calcium, and zinc as well as precursors therefor and mixtures of any of the foregoing.

Embodiment #181 is a hydrogenation catalyst of embodiment #177, wherein the support modifier is chosen from the group consisting of oxides and metasilicates of magnesium, calcium, and zinc as well as precursors therefor and mixtures of any of the foregoing.

Embodiment #182 is a hydrogenation catalyst of embodiment #177, wherein the support modifier is chosen from the group consisting of calcium metasilicate, precursors for calcium metasilicate and mixtures of calcium metasilicate and precursors therefor.

Embodiment #183 is a hydrogenation catalyst of embodiment #176, wherein the support modifier is chosen from the group consisting of oxides and metasilicates of sodium, potassium, magnesium, calcium, and zinc as well as precursors therefor and mixtures of any of the foregoing.

Embodiment #184 is a hydrogenation catalyst of embodiment #176, wherein the support modifier is chosen from the group consisting of oxides and metasilicates of sodium, potassium, magnesium, calcium, and zinc as well as precursors therefor and mixtures of any of the foregoing.

Embodiment #185 is a hydrogenation catalyst of embodiment #176, wherein the support modifier is chosen from the group consisting of oxides and metasilicates of magnesium, calcium, and zinc as well as precursors therefor and mixtures of any of the foregoing.

Embodiment #186 is a hydrogenation catalyst of embodiment #176, wherein the support modifier is chosen from the group consisting of oxides and metasilicates of magnesium, calcium, and zinc as well as precursors therefor and mixtures of any of the foregoing.

Embodiment #187 is a hydrogenation catalyst of embodiment #176, wherein the support modifier is chosen from the group consisting of calcium metasilicate, precursors for calcium metasilicate and mixtures of calcium metasilicate and precursors therefor.

Embodiment #188 is a hydrogenation catalyst of embodiment #176, wherein the total weight of platinum group metals present is between 0.5 and 2%, the amount of platinum present is at least 0.5%, the promoter is cobalt, the weight ratio of cobalt to platinum being between 20:1 and 3:1, and the amount of support modifier is between 3 and 90%.

Embodiment #189 is a hydrogenation catalyst of embodiment #188, wherein the support modifier is chosen from the group consisting of oxides and metasilicates of sodium, potassium, magnesium, calcium, and zinc as well as precursors therefor and mixtures of any of the foregoing.

Embodiment #190 is a hydrogenation catalyst of embodiment #188, wherein the support modifier is chosen from the group consisting of oxides and metasilicates of sodium, potassium, magnesium, calcium, and zinc as well as precursors therefor and mixtures of any of the foregoing.

Embodiment #191 is a hydrogenation catalyst of embodiment #188, wherein the support modifier is chosen from the group consisting of oxides and metasilicates of magnesium, calcium, and zinc as well as precursors therefor and mixtures of any of the foregoing.

Embodiment #192 is a hydrogenation catalyst of embodiment #188, wherein the support modifier is chosen from the group consisting of oxides and metasilicates of magnesium, calcium, and zinc as well as precursors therefor and mixtures of any of the foregoing.

Embodiment #193 is a hydrogenation catalyst of embodiment #188, wherein the support modifier is chosen from the group consisting of calcium metasilicate, precursors for calcium metasilicate and mixtures of calcium metasilicate and precursors therefor.

Embodiment #194 is a hydrogenation catalyst of embodiment #176, wherein the total weight of platinum group metals present is between 0.5 and 2%, the amount of palladium present is at least 0.5%, the promoter is cobalt, the weight ratio of cobalt to palladium being between 20:1 and 3:1, and the amount of support modifier is between 3 and 90%.

Embodiment #195 is a hydrogenation catalyst of embodiment #194, wherein the support modifier is chosen from the group consisting of oxides and metasilicates of sodium, potassium, magnesium, calcium, and zinc as well as precursors therefor and mixtures of any of the foregoing.

Embodiment #196 is a hydrogenation catalyst of embodiment #194, wherein the support modifier is chosen from the group consisting of oxides and metasilicates of sodium, potassium, magnesium, calcium, and zinc as well as precursors therefor and mixtures of any of the foregoing.

Embodiment #197 is a hydrogenation catalyst of embodiment #194, wherein the support modifier is chosen from the group consisting of oxides and metasilicates of magnesium, calcium, and zinc as well as precursors therefor and mixtures of any of the foregoing.

Embodiment #198 is a hydrogenation catalyst of embodiment #194, wherein the support modifier is chosen from the group consisting of oxides and metasilicates of magnesium, calcium, and zinc as well as precursors therefor and mixtures of any of the foregoing.

Embodiment #199 is a hydrogenation catalyst of embodiment #194, wherein the support modifier is chosen from the group consisting of calcium metasilicate, precursors for calcium metasilicate and mixtures of calcium metasilicate and precursors therefor.

Embodiment #200 is a hydrogenation catalyst comprising: between 2.5 and 3.5 weight percent platinum, between 3 weight % and 5 weight % tin dispersed on high surface area pyrogenic silica having a surface area of at least 200 m$^2$ per gram, said high surface area silica being promoted with between 4 and 6% calcium metasilicate, the molar ratio of platinum to tin being between 4:5 and 5:4.

Embodiment #201 is a hydrogenation catalyst comprising: between 0.5 and 2.5 weight percent palladium, between 2 weight % and 7 weight % rhenium, the weight ratio of rhenium to palladium being at least 1.5:1.0, said rhenium and palladium being dispersed on a silicaceous support, said silicaceous support comprising at least 80% calcium metasilicate.

Embodiment #202 is a hydrogenation catalyst incorporating catalytic metals chosen from the group consisting of: Fe, Co, Ni, Ru, Rh, Pd, Ir, Pt, Os, Ti, Zn, Cr, Mo and W in an amount of from about 0.1% to about 10% by weight on a stabilized-modified oxidic support incorporating basic non-volatile stabilizer-modifiers in the form of oxides and metasilicates of alkaline earth metals, alkali metals, zinc, scandium and yttrium precursors for the oxides and metasilicates, as well as mixtures thereof in amounts sufficient to counteract acidic sites present on the surface thereof, impart resistance to shape change (primarily due to inter alia sintering, grain growth, gain boundary migration, migration of defects and dislocations, plastic deformation and/or other temperature induced changes in microstructure) at temperatures encountered in hydrogenation of acetic acid or both.

Embodiment #203 is a hydrogenation catalyst of embodiment #202 wherein the amount and location of basic modifier-stabilizer is sufficient to reduce the number of acid sites present per square meter on the surface of the oxidic support below the number of acid sites found per square meter on the surface of pyrogenic silica having a purity of at least about 99.7% by weight.

Embodiment #204 is a hydrogenation catalyst of embodiment #202 wherein the amount and location of basic modifier-stabilizer is sufficient to reduce the number of acid sites present per square meter on the surface of the oxidic support below the number of acid sites found per square meter on the surface of Saint-Gobain N or Pro HSA SS 61138 having a purity of at least about 99.7% by weight.

Embodiment #205 is a hydrogenation catalyst of embodiment #202 wherein the amount and location of basic modifier-stabilizer is sufficient to reduce the number of acid sites present per square meter on the surface of the oxidic support below half the number of acid sites found per square meter on the surface of pyrogenic silica having a purity of about 99.7% by weight.

Embodiment #206 is a hydrogenation catalyst of embodiment #202 wherein the amount and location of basic modifier-stabilizer is sufficient to reduce the number of acid sites present per square meter on the surface of the oxidic support below half the number of acid sites found per square meter on the surface of Saint-Gobain N or Pro HSA SS 61138 having a purity of at least about 99.7% by weight.

Embodiment #207 is a hydrogenation catalyst of embodiment #202 wherein the amount and location of basic modifier-stabilizer is sufficient to reduce the number of acid sites present per square meter on the surface of the oxidic support below twenty five percent of the number of acid sites found per square meter on the surface of pyrogenic silica having a purity of about 99.7% by weight.

Embodiment #208 is a hydrogenation catalyst of embodiment #202 wherein the amount and location of basic modifier-stabilizer is sufficient to reduce the number of acid sites present per square meter on the surface of the oxidic support below twenty five percent of the number of acid sites found per square meter on the surface of Saint-Gobain N or Pro HSA SS 61138 having a purity of at least about 99.7% by weight.

Embodiment #209 is a hydrogenation catalyst of embodiment #202 wherein the amount and location of basic modifier-stabilizer is sufficient to reduce the number of acid sites present per square meter on the surface of the oxidic support below ten percent of the number of acid sites found per square meter on the surface of pyrogenic silica having a purity of about 99.7% by weight.

Embodiment #210 is a hydrogenation catalyst of embodiment #202 wherein the amount and location of basic modifier-stabilizer is sufficient to reduce the number of acid sites present per square meter on the surface of the oxidic support below ten percent of the number of acid sites found per square meter on the surface of Saint-Gobain N or Pro HSA SS 61138 having a purity of at least about 99.7% by weight.

In the foregoing descriptions of the various embodiments, those embodiments which refer to another embodiment may be appropriately combined with other embodiments as will be appreciated by one of skill in the art.

As our invention, we claim:

1. A process for hydrogenating alkanoic acids comprising passing a gaseous stream comprising hydrogen and an alkanoic acid in the vapor phase over a hydrogenation catalyst comprising:
   a main metal selected from the group consisting of platinum, palladium, rhenium and mixtures thereof on a support selected from the group consisting of iron oxide, alumina, titania, zirconia, magnesium oxide, carbon, graphite and mixtures thereof; and
   a metallic promoter selected the group consisting of tin, rhenium and mixtures thereof, the support being promoted with a redox promoter selected from the group consisting of: $WO_3$; $MoO_3$; $Fe_2O_3$ and $Cr_2O_3$.

2. The process of claim 1, wherein the main metal is rhenium.

3. The process of claim 1, wherein at least 80% of the acetic acid converted is converted to ethanol and wherein less than 4% of the acetic acid is converted to compounds other than compounds selected from the group consisting of ethanol, ethyl acetate, acetaldehyde, ethylene, diethyl ether and mixtures thereof.

4. The process of claim 1, wherein the main metal may be present from 0.1 to 10% by weight.

5. The process of claim 1, wherein the process is conducted at a temperature from 225° C. and 300° C. and wherein the molar ratio of hydrogen to acetic acid is at least 4:1.

6. The process of claim 1, wherein the process is conducted in a reactor selected from the group consisting of a fixed bed reactor, a fluid bed reactor and an ebullient bed reactor.

* * * * *